United States Patent
Bergstrom et al.

(10) Patent No.: US 10,947,317 B2
(45) Date of Patent: Mar. 16, 2021

(54) NAPI2B-TARGETED ANTIBODY-DRUG CONJUGATES AND METHODS OF USE THEREOF

(71) Applicant: Mersana Therapeutics, Inc., Cambridge, MA (US)

(72) Inventors: Donald A. Bergstrom, Winchester, MA (US); Natalya D. Bodyak, Brookline, MA (US); Timothy B. Lowinger, Carlisle, MA (US); Peter U. Park, Lincoln, MA (US); Laura L. Poling, Boston, MA (US); Aleksandr V. Yurkovetskiy, Littleton, MA (US)

(73) Assignee: Mersana Therapeutics, Inc., Cambridge, MA (US)

( * ) Notice: Subject to any disclaimer, the term of this patent is extended or adjusted under 35 U.S.C. 154(b) by 129 days.

(21) Appl. No.: 15/457,574

(22) Filed: Mar. 13, 2017

(65) Prior Publication Data
US 2017/0266311 A1    Sep. 21, 2017

Related U.S. Application Data

(60) Provisional application No. 62/308,567, filed on Mar. 15, 2016, provisional application No. 62/323,068, filed on Apr. 15, 2016, provisional application No. 62/383,324, filed on Sep. 2, 2016.

(51) Int. Cl.
| C07K 16/30 | (2006.01) |
| A61K 47/68 | (2017.01) |
| C07K 16/32 | (2006.01) |

(52) U.S. Cl.
CPC ...... *C07K 16/3023* (2013.01); *A61K 47/6805* (2017.08); *A61K 47/6811* (2017.08); *A61K 47/6851* (2017.08); *A61K 47/6857* (2017.08); *A61K 47/6869* (2017.08); *A61K 47/6883* (2017.08); *C07K 16/3069* (2013.01); *C07K 16/32* (2013.01); *C07K 2317/21* (2013.01); *C07K 2317/24* (2013.01); *C07K 2317/565* (2013.01)

(58) Field of Classification Search
CPC ............ A61K 47/6851; A61K 47/6811; A61K 47/6883; A61K 47/6803
See application file for complete search history.

(56) References Cited

U.S. PATENT DOCUMENTS

| 7,803,562 | B2 | 9/2010 | Cannon et al. |
| 8,383,799 | B2 | 2/2013 | Guo et al. |
| 8,535,675 | B2 | 9/2013 | Dennis et al. |
| 8,603,474 | B2 | 12/2013 | Ritter et al. |
| 8,703,714 | B2 | 4/2014 | Doronina et al. |
| 8,742,076 | B2 | 6/2014 | Cohen et al. |
| 8,802,094 | B2 | 8/2014 | Cook et al. |
| 8,809,339 | B2 | 8/2014 | Lewis et al. |
| 8,815,908 | B2 | 8/2014 | Lewis et al. |
| 8,815,910 | B2 | 8/2014 | Lewis et al. |
| 8,900,589 | B2 | 12/2014 | Beria et al. |
| 8,916,569 | B2 | 12/2014 | Lewis et al. |
| 9,045,533 | B2 | 6/2015 | Ritter et al. |
| 2012/0321583 | A1* | 12/2012 | Yurkovetskiy ........... C07K 7/02 424/78.17 |

FOREIGN PATENT DOCUMENTS

| WO | WO 2003/060086 | 7/2003 |
| WO | WO 2009/097128 A1 | 8/2009 |
| WO | WO 2011/066503 | 6/2011 |
| WO | WO 2012/171020 A1 | 12/2012 |
| WO | WO 2015/054669 A1 | 4/2015 |

OTHER PUBLICATIONS

Abstract of Gordon et al (Journal of Clinical Oncology, 2013, vol. 31, No. 15, suppl., Abstract No. 2507) (Year: 2013).*
Carter et al (The Cancer Journal, 2008, vol. 14, pp. 154-169) (Year: 2008).*
Grill and Martin Reviews in Endocrine & Metabolic Disorders, 2000, vol. 1, pp. 253-263 (Year: 2000).*
Ikezoe, Journal of Hematology, 2014, vol. 100, pp. 27-37 (Year: 2014).*
Yin, B. W.T. et al. "Monoclonal antibody MX35 detects the membrane transporter NaPi2b (SLC34A2) in human carcinomas", Cancer Immunity, vol. 8, 2008, 9 pages.
Burris, H. et al. "A phase I study of DNIB0600A, an antibody-drug conjugate (ADC) targeting NaPi2b, in patients (pts) with non-small cell lung cancer (NSCLC) or platinum-resistant ovarian cancer (OC)", J Clin Oncol 32, Abstract 2504, 2014, 4 pages.
Forster, I. et al. "Phosphate transporters of the SLC20 and SLC34 families", Molecular Aspects of Medicine, 34, 2013, p. 386-395.
Kiyamova, R. et al. "Immunohistochemical Analysis of NAPI2B Protein (MX35 Antigen) Expression and Subcellular Localization in Human Normal and Cancer Tissues", Experimental Oncology, vol. 33, No. 3, p. 157-161, 2011.
Lin, K. et al. "Preclinical Development of an Anti-NaPi2b (SLC34A2) Antibody—Drug Conjugate as a Therapeutic for Non-Small Cell Lung and Ovarian Cancers", Clinical Cancer Research, 21, 2015, p. 5139-5150.
Lindegren, S. et al. "Binding Affinity, Specificity and Comparative Biodistribution of the Parental Murine Monoclonal Antibody MX35 (Anti-NaPi2b) and Its Humanized Version Rebmab200", PLoS One, 2015, p. 1-16.

(Continued)

*Primary Examiner* — Karen A. Canella
(74) *Attorney, Agent, or Firm* — Cooley LLP; Cynthia A. Kozakiewicz; Andrew Henderson

(57) ABSTRACT

This disclosure provides NaPi2b-targeted antibody-drug conjugates (e.g., NaPi2b-targeted antibody-polymer-drug conjugates) that specifically bind to the extracellular region of SLC34A2, and to methods of using such conjugates in a variety of therapeutic, diagnostic, and prophylactic indications.

15 Claims, 7 Drawing Sheets

Specification includes a Sequence Listing.

(56) References Cited

OTHER PUBLICATIONS

Dos Santos, M. L. et al. "Rebmab200, a Humanized Monoclonal Antibody Targeting the Sodium Phosphate Transporter NaPi2b Displays Strong Immune Mediated Cytotoxicity against Cancer: A Novel Reagent for Targeted Antibody Therapy of Cancer", PLoS One, vol. 8, Issue 7, 2013, e70332 (10 pages).

Mattes, M. Jules et al. "Mouse Monoclonal Antibodies to Human Epithelial Differentiation Antigens Expressed on the Surface of Ovarian Carcinoma Ascites Cells", Cancer Research, 47, 1987, p. 6741-6750.

Rangel, L. et al. "Characterization of novel human ovarian cancer-specific transcripts (HOSTs) identified by serial analysis of gene expression", Oncogene (2003) 22, p. 7225-7232.

Wagner, C. et al. "The SLC34 family of sodium-dependent phosphate transporters", Eur J Physiol, 466, (2014), p. 139-153.

Dos Santos, M. L. et al. "Generation of a Stable Cell Line for Rebmab 200 MAB" 22nd ESACT Meeting Vienna, Austria, May 15-18, 2011.

Dos Santos, M. L. et al. "Flow cytometry characteristics of Rebmab 200" 9th PEAC Conference, Jackson Hole, Wyoming, USA, Sep. 19-23, 2009.

Degaki, T. L. et al. "Generation of Humanized Rebmab 200" 9th PEAC Conference, Jackson Hole, Wyoming, USA, Sep. 19-23, 2009.

Dos Santos, M. L. et al. "Stability of Humanized Rebmab 100 monoclonal antibody" 9th PEAC Conference, Jackson Hole, Wyoming, USA, Sep. 19-23, 2009.

Doronina et al., "Development of potent monoclonal antibody auristatin conjugates for cancer therapy", *Nature Biotechnology* 21(7):778-784 (2003).

Banerjee S. et al. "A Randomized, Open-Label, Phase II Study of Anti-NaPi2b Antibody-Drug Conjugate Lifastuzumab Vedotin (DNIB0600A) Compared to Pegylated Liposomal Doxorubicin in Patients with Platinum-Resistant Ovarian Cancer", ASCO Annual Meeting, Jun. 3-7, 2016, slide 5569, 1 page.

Bodyak, N. et al. "Abstract 1194: Discovery and preclinical development of a highly potent NaPi2b-targeted antibody-drug conjugate (ADC) with significant activity in patient-derived non-small cell lung cancer (NSCLC) xenograft models", Mersana Therapeutics (poster), Experimental and Molecular Therapeutics, AACR Journals, 107th Annual Meeting Apr. 16-20, 2016, published 2016, vol. 76, Issue 14, 3 pages.

D'Arcangelo, M. et al. "Prevalence and prognostic significance of sodium-dependent phosphate transporter 2b (NaPi2b) protein expression in non-small cell lung cancer", Biomarkers, Annals of Oncology, vol. 25 (Supplement), iv58-iv84, 2014, 1 page.

Gerber, D. et al. "Safety, Pharmacokinetics, and Activity of the Anti-NaPi2b Antibody-Drug Conjugate DNIB0600A: A Phase I Study in Patients with Non-Small Cell Lung Cancer and Platinum-Resistant Ovarian Cancer", IASLC World Lung, Sydney, Australia, Oct. 27-30, 2013, (poster), 1 page.

\* cited by examiner

SEQUENCE LISTING

```
<160> NUMBER OF SEQ ID NOS: 24

<210> SEQ ID NO 1
<211> LENGTH: 449
<212> TYPE: PRT
<213> ORGANISM: Homo sapiens

<400> SEQUENCE: 1

Gln Val Gln Leu Val Gln Ser Gly Ala Glu Val Val Lys Pro Gly Ala
1               5                   10                  15

Ser Val Lys Met Ser Cys Lys Ala Ser Gly Tyr Thr Phe Thr Gly Tyr
            20                  25                  30

Asn Ile His Trp Val Lys Gln Ala Pro Gly Gln Gly Leu Glu Trp Ile
        35                  40                  45

Gly Ala Ile Tyr Pro Gly Asn Gly Asp Thr Ser Tyr Lys Gln Lys Phe
    50                  55                  60

Arg Gly Arg Ala Thr Leu Thr Ala Asp Thr Ser Thr Ser Thr Val Tyr
65                  70                  75                  80

Met Glu Leu Ser Ser Leu Arg Ser Glu Asp Ser Ala Val Tyr Tyr Cys
```

```
            85                  90                  95
Ala Arg Gly Glu Thr Ala Arg Ala Thr Phe Ala Tyr Trp Gly Gln Gly
            100                 105                 110

Thr Leu Val Thr Val Ser Ser Gly Ala Ser Thr Lys Gly Pro Ser Val
        115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly

<210> SEQ ID NO 2
<211> LENGTH: 215
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
```

```
1               5                   10                  15
Asp Arg Val Thr Ile Thr Cys Ser Ala Ser Gln Asp Ile Gly Asn Phe
                    20                  25                  30

Leu Asn Trp Tyr Gln Gln Lys Pro Gly Lys Thr Val Lys Val Leu Ile
                35                  40                  45

Tyr Tyr Thr Ser Ser Leu Tyr Ser Gly Val Pro Ser Arg Phe Ser Gly
            50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Lys Leu Pro Leu
                85                  90                  95

Thr Phe Gly Gln Gly Thr Lys Leu Glu Leu Lys Arg Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
                210                 215

<210> SEQ ID NO 3
<211> LENGTH: 120
<212> TYPE: PRT
<213> ORGANISM: Homo sapiens

<400> SEQUENCE: 3

Gln Val Gln Leu Val Gln Ser Gly Ala Glu Val Val Lys Pro Gly Ala
1               5                   10                  15

Ser Val Lys Met Ser Cys Lys Ala Ser Gly Tyr Thr Phe Thr Gly Tyr
                20                  25                  30

Asn Ile His Trp Val Lys Gln Ala Pro Gly Gln Gly Leu Glu Trp Ile
                35                  40                  45

Gly Ala Ile Tyr Pro Gly Asn Gly Asp Thr Ser Tyr Lys Gln Lys Phe
            50                  55                  60

Arg Gly Arg Ala Thr Leu Thr Ala Asp Thr Ser Thr Ser Thr Val Tyr
65                  70                  75                  80

Met Glu Leu Ser Ser Leu Arg Ser Glu Asp Ser Ala Val Tyr Tyr Cys
                85                  90                  95

Ala Arg Gly Glu Thr Ala Arg Ala Thr Phe Ala Tyr Trp Gly Gln Gly
                100                 105                 110

Thr Leu Val Thr Val Ser Ser Gly
            115                 120

<210> SEQ ID NO 4
<211> LENGTH: 108
<212> TYPE: PRT
<213> ORGANISM: Homo sapiens
```

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Gly Asn Phe
            20                  25                  30

Leu Asn Trp Tyr Gln Gln Lys Pro Gly Lys Thr Val Lys Val Leu Ile
        35                  40                  45

Tyr Tyr Thr Ser Ser Leu Tyr Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Lys Leu Pro Leu
                85                  90                  95

Thr Phe Gly Gln Gly Thr Lys Leu Glu Leu Lys Arg
            100                 105

<210> SEQ ID NO 5
<211> LENGTH: 10
<212> TYPE: PRT
<213> ORGANISM: Homo sapiens

<400> SEQUENCE: 5

Gly Tyr Thr Phe Thr Gly Tyr Asn Ile His
1               5                   10

<210> SEQ ID NO 6
<211> LENGTH: 17
<212> TYPE: PRT
<213> ORGANISM: Homo sapiens

<400> SEQUENCE: 6

Ala Ile Tyr Pro Gly Asn Gly Asp Thr Ser Tyr Lys Gln Lys Phe Arg
1               5                   10                  15

Gly

<210> SEQ ID NO 7
<211> LENGTH: 10
<212> TYPE: PRT
<213> ORGANISM: Homo sapiens

<400> SEQUENCE: 7

Gly Glu Thr Ala Arg Ala Thr Phe Ala Tyr
1               5                   10

<210> SEQ ID NO 8
<211> LENGTH: 11
<212> TYPE: PRT
<213> ORGANISM: Homo sapiens

<400> SEQUENCE: 8

Ser Ala Ser Gln Asp Ile Gly Asn Phe Leu Asn
1               5                   10

<210> SEQ ID NO 9
<211> LENGTH: 7
<212> TYPE: PRT
<213> ORGANISM: Homo sapiens

<400> SEQUENCE: 9

Tyr Thr Ser Ser Leu Tyr Ser
1               5

```
<210> SEQ ID NO 10
<211> LENGTH: 9
<212> TYPE: PRT
<213> ORGANISM: Homo sapiens

<400> SEQUENCE: 10

Gln Gln Tyr Ser Lys Leu Pro Leu Thr
1               5

<210> SEQ ID NO 11
<211> LENGTH: 329
<212> TYPE: PRT
<213> ORGANISM: Homo sapiens

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

Gln Lys Ser Leu Ser Leu Ser Pro Gly
            325

<210> SEQ ID NO 12
<211> LENGTH: 107
<212> TYPE: PRT
<213> ORGANISM: Homo sapiens

<400> SEQUENCE: 12

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 13
<211> LENGTH: 329
<212> TYPE: PRT
<213> ORGANISM: Homo sapiens

<400> SEQUENCE: 13

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

```
Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 14
<211> LENGTH: 449
<212> TYPE: PRT
<213> ORGANISM: Homo sapiens

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Phe
            20                  25                  30

Ala Met Ser Trp Val Arg Gln Ala Pro Gly Lys Gly Leu Glu Trp Val
        35                  40                  45

Ala Thr Ile Gly Arg Val Ala Phe His Thr Tyr Tyr Pro Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Phe Asp Val Gly His Phe Asp Phe Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
```

```
                    245                 250                 255
Ser Arg Thr Pro Glu Val Thr Cys Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 15
<211> LENGTH: 219
<212> TYPE: PRT
<213> ORGANISM: Homo sapiens

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ser Ser Glu Thr Leu Val His Ser
            20                  25                  30

Ser Gly Asn Thr Tyr Leu Glu Trp Tyr Gln Gln Lys Pro Gly Lys Ala
        35                  40                  45

Pro Lys Leu Leu Ile Tyr Arg Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Phe Asn Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
```

```
                165                 170                 175
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 16
<211> LENGTH: 120
<212> TYPE: PRT
<213> ORGANISM: Homo sapiens

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Phe
            20                  25                  30

Ala Met Ser Trp Val Arg Gln Ala Pro Gly Lys Gly Leu Glu Trp Val
        35                  40                  45

Ala Thr Ile Gly Arg Val Ala Phe His Thr Tyr Tyr Pro Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Phe Asp Val Gly His Phe Asp Phe Trp Gly Gln
            100                 105                 110

Gly Thr Leu Val Thr Val Ser Ser
        115                 120

<210> SEQ ID NO 17
<211> LENGTH: 112
<212> TYPE: PRT
<213> ORGANISM: Homo sapiens

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ser Ser Glu Thr Leu Val His Ser
            20                  25                  30

Ser Gly Asn Thr Tyr Leu Glu Trp Tyr Gln Gln Lys Pro Gly Lys Ala
        35                  40                  45

Pro Lys Leu Leu Ile Tyr Arg Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Phe Asn Pro Leu Thr Phe Gly Gln Gly Thr Lys Val Glu Ile Lys
            100                 105                 110

<210> SEQ ID NO 18
<211> LENGTH: 10
<212> TYPE: PRT
<213> ORGANISM: Homo sapiens

<400> SEQUENCE: 18
```

```
Gly Phe Ser Phe Ser Asp Phe Ala Met Ser
1               5                   10
```

<210> SEQ ID NO 19
<211> LENGTH: 18
<212> TYPE: PRT
<213> ORGANISM: Homo sapiens

<400> SEQUENCE: 19

```
Ala Thr Ile Gly Arg Val Ala Phe His Thr Tyr Tyr Pro Asp Ser Met
1               5                   10                  15

Lys Gly
```

<210> SEQ ID NO 20
<211> LENGTH: 13
<212> TYPE: PRT
<213> ORGANISM: Homo sapiens

<400> SEQUENCE: 20

```
Ala Arg His Arg Gly Phe Asp Val Gly His Phe Asp Phe
1               5                   10
```

<210> SEQ ID NO 21
<211> LENGTH: 16
<212> TYPE: PRT
<213> ORGANISM: Homo sapiens

<400> SEQUENCE: 21

```
Arg Ser Ser Glu Thr Leu Val His Ser Ser Gly Asn Thr Tyr Leu Glu
1               5                   10                  15
```

<210> SEQ ID NO 22
<211> LENGTH: 7
<212> TYPE: PRT
<213> ORGANISM: Homo sapiens

<400> SEQUENCE: 22

```
Arg Val Ser Asn Arg Phe Ser
1               5
```

<210> SEQ ID NO 23
<211> LENGTH: 9
<212> TYPE: PRT
<213> ORGANISM: Homo sapiens

<400> SEQUENCE: 23

```
Phe Gln Gly Ser Phe Asn Pro Leu Thr
1               5
```

<210> SEQ ID NO 24
<211> LENGTH: 690
<212> TYPE: PRT
<213> ORGANISM: Homo sapiens

<400> SEQUENCE: 24

```
Met Ala Pro Trp Pro Glu Leu Gly Asp Ala Gln Pro Asn Pro Asp Lys
1               5                   10                  15

Tyr Leu Glu Gly Ala Ala Gly Gln Gln Pro Thr Ala Pro Asp Lys Ser
            20                  25                  30

Lys Glu Thr Asn Lys Thr Asp Asn Thr Glu Ala Pro Val Thr Lys Ile
        35                  40                  45

Glu Leu Leu Pro Ser Tyr Ser Thr Ala Thr Leu Ile Asp Glu Pro Thr
    50                  55                  60

Glu Val Asp Asp Pro Trp Asn Leu Pro Thr Leu Gln Asp Ser Gly Ile
65                  70                  75                  80

Lys Trp Ser Glu Arg Asp Thr Lys Gly Lys Ile Leu Cys Phe Phe Gln
                85                  90                  95

Gly Ile Gly Arg Leu Ile Leu Leu Gly Phe Leu Tyr Phe Phe Val
            100                 105                 110

Cys Ser Leu Asp Ile Leu Ser Ser Ala Phe Gln Leu Val Gly Gly Lys
            115                 120                 125

Met Ala Gly Gln Phe Phe Ser Asn Ser Ser Ile Met Ser Asn Pro Leu
    130                 135                 140

Leu Gly Leu Val Ile Gly Val Leu Val Thr Val Leu Val Gln Ser Ser
145                 150                 155                 160

Ser Thr Ser Thr Ser Ile Val Val Ser Met Val Ser Ser Ser Leu Leu
                165                 170                 175

Thr Val Arg Ala Ala Ile Pro Ile Ile Met Gly Ala Asn Ile Gly Thr
            180                 185                 190

Ser Ile Thr Asn Thr Ile Val Ala Leu Met Gln Val Gly Asp Arg Ser
        195                 200                 205

Glu Phe Arg Arg Ala Phe Ala Gly Ala Thr Val His Asp Phe Phe Asn
    210                 215                 220

Trp Leu Ser Val Leu Val Leu Leu Pro Val Glu Val Ala Thr His Tyr
225                 230                 235                 240

Leu Glu Ile Ile Thr Gln Leu Ile Val Glu Ser Phe His Phe Lys Asn
                245                 250                 255

Gly Glu Asp Ala Pro Asp Leu Leu Lys Val Ile Thr Lys Pro Phe Thr
            260                 265                 270

Lys Leu Ile Val Gln Leu Asp Lys Lys Val Ile Ser Gln Ile Ala Met
        275                 280                 285

Asn Asp Glu Lys Ala Lys Asn Lys Ser Leu Val Lys Ile Trp Cys Lys
    290                 295                 300

Thr Phe Thr Asn Lys Thr Gln Ile Asn Val Thr Val Pro Ser Thr Ala
305                 310                 315                 320

Asn Cys Thr Ser Pro Ser Leu Cys Trp Thr Asp Gly Ile Gln Asn Trp
                325                 330                 335

Thr Met Lys Asn Val Thr Tyr Lys Glu Asn Ile Ala Lys Cys Gln His
            340                 345                 350

Ile Phe Val Asn Phe His Leu Pro Asp Leu Ala Val Gly Thr Ile Leu
        355                 360                 365
```

```
Leu Ile Leu Ser Leu Leu Val Leu Cys Gly Cys Leu Ile Met Ile Val
        370                 375                 380

Lys Ile Leu Gly Ser Val Leu Lys Gly Gln Val Ala Thr Val Ile Lys
385                 390                 395                 400

Lys Thr Ile Asn Thr Asp Phe Pro Phe Pro Phe Ala Trp Leu Thr Gly
                405                 410                 415

Tyr Leu Ala Ile Leu Val Gly Ala Gly Met Thr Phe Ile Val Gln Ser
                420                 425                 430

Ser Ser Val Phe Thr Ser Ala Leu Thr Pro Leu Ile Gly Ile Gly Val
            435                 440                 445

Ile Thr Ile Glu Arg Ala Tyr Pro Leu Thr Leu Gly Ser Asn Ile Gly
450                 455                 460

Thr Thr Thr Thr Ala Ile Leu Ala Ala Leu Ala Ser Pro Gly Asn Ala
465                 470                 475                 480

Leu Arg Ser Ser Leu Gln Ile Ala Leu Cys His Phe Phe Asn Ile
                485                 490                 495

Ser Gly Ile Leu Leu Trp Tyr Pro Ile Pro Phe Thr Arg Leu Pro Ile
                500                 505                 510

Arg Met Ala Lys Gly Leu Gly Asn Ile Ser Ala Lys Tyr Arg Trp Phe
                515                 520                 525

Ala Val Phe Tyr Leu Ile Ile Phe Phe Phe Leu Ile Pro Leu Thr Val
            530                 535                 540

Phe Gly Leu Ser Leu Ala Gly Trp Arg Val Leu Val Gly Val Gly Val
545                 550                 555                 560

Pro Val Val Phe Ile Ile Ile Leu Val Leu Cys Leu Arg Leu Leu Gln
                565                 570                 575

Ser Arg Cys Pro Arg Val Leu Pro Lys Lys Leu Gln Asn Trp Asn Phe
            580                 585                 590

Leu Pro Leu Trp Met Arg Ser Leu Lys Pro Trp Asp Ala Val Val Ser
                595                 600                 605

Lys Phe Thr Gly Cys Phe Gln Met Arg Cys Cys Cys Cys Cys Arg Val
                610                 615                 620

Cys Cys Arg Ala Cys Cys Leu Leu Cys Asp Cys Pro Lys Cys Cys Arg
625                 630                 635                 640

Cys Ser Lys Cys Cys Glu Asp Leu Glu Glu Ala Gln Glu Gly Gln Asp
                645                 650                 655

Val Pro Val Lys Ala Pro Glu Thr Phe Asp Asn Ile Thr Ile Ser Arg
                660                 665                 670

Glu Ala Gln Gly Glu Val Pro Ala Ser Asp Ser Lys Thr Glu Cys Thr
                675                 680                 685

Ala Leu
    690
```

NAPI2B-TARGETED ANTIBODY-DRUG CONJUGATES AND METHODS OF USE THEREOF

RELATED APPLICATIONS

This application claims priority to, and the benefit of, U.S. provisional application Nos. 62/308,567, filed Mar. 15, 2016; 62/323,068 filed Apr. 15, 2016 and 62/383,324 filed Sep. 2, 2016, under 35 USC § 119(e). The contents of each of these applications are hereby incorporated by reference in their entireties.

INCORPORATION-BY-REFERENCE OF SEQUENCE LISTING

The contents of the text file named "MRSNO16001US ST25.txt", which was created on Mar. 27, 2017 and is 30 KB in size, are hereby incorporated by reference in their entireties.

FIELD OF THE DISCLOSURE

This disclosure relates generally to NaPi2b-targeted antibody-drug conjugates (such as NaPi2b-targeted antibody-polymer-drug conjugates) that specifically bind to the extracellular region of SLC34A2, and to methods of using these conjugates as therapeutics and/or diagnostics.

BACKGROUND

NaPi2b (SLC34A2, NaPiIIb, Npt2), a multi-transmembrane, sodium-dependent phosphate transporter (Xu et al. Genomics 62:281-284 (1999)), is normally expressed at the brush border membrane of mammalian small intestine and participates in the transcellular inorganic phosphate (Pi) absorption, contributing to the maintenance of phosphate homeostasis in the body. The expression of NaPi2b at the protein level has been detected in the liver, at the apical surface of epithelial cells of mammary, salivary glands, and in the lungs, testis, salivary gland, thyroid gland, small intestine, and uterus. Mutations in NaPi2b have been associated with clinical syndromes of alveolar and testicular microlithiasis. NaPi2b is highly expressed in non-squamous non-small cell lung cancer (NSCLC), non-mucinous ovarian cancer and papillary thyroid cancer. NaPi2b-positive tissue immunoreactivity is present in 61% of NSCLC, and 92% ovarian cancer specimens.

Ovarian cancer is one of the most common gynecologic malignancies and the fifth most frequent cause of cancer death in women. The high mortality rate results in part from the frequent diagnosis of ovarian cancer at advanced stages and the mortality rate is approximately 65% of the incidence rate. Epithelial tumors of ovary comprise 58% of all ovarian neoplasms and more than 90% of malignant tumors of ovary. Debulking surgery and platinum-based combination chemotherapy (including taxanes) are current treatment modalities; however, the majority of patients with relapsed epithelial ovarian cancer eventually succumb to the disease. There is a need for novel treatment modalities in ovarian cancer, including targeted therapies such as immunotherapy with monoclonal antibodies or cancer vaccine-based approaches.

NSCLC is any type of epithelial lung cancer other than small cell lung carcinoma (SCLC). NSCLC accounts for about 85% of all lung cancers. As a class, NSCLCs are relatively insensitive to chemotherapy, compared to small cell carcinoma. When possible, they are primarily treated by surgical resection with curative intent, although chemotherapy is increasingly being used both pre-operatively (neoadjuvant chemotherapy) and post-operatively (adjuvant chemotherapy). In the metastatic or inoperative setting, chemotherapy and/or immunotherapy is used, although the disease at this stage is largely incurable and survival times remains short. There is a need for novel treatment modalities in NSCLC, including targeted therapies such as immunotherapy with monoclonal antibodies or cancer vaccine-based approaches.

Accordingly, there exists a need for therapies that target the biological activities of NaPi2b.

SUMMARY

The present disclosure provides a NaPi2b-targeted antibody-drug conjugate (such as a NaPi2b-targeted antibody-polymer-drug conjugate) that is biodegradable, biocompatible and exhibits high drug load as well as specific binding to the extracellular region of SLC34A2. The NaPi2b-targeted antibody-drug conjugates (e.g., NaPi2b-targeted antibody-polymer-drug conjugates) provided herein include an antibody that specifically recognizes NaPi2b, also known as sodium-dependent phosphate transport protein 2B. The antibodies used in the NaPi2b-targeted antibody-drug conjugates disclosed herein can or may also include those that are capable of and useful for modulating, blocking, inhibiting, reducing, antagonizing, neutralizing or otherwise interfering with at least one biological activity of NaPi2b. Antibodies disclosed herein also include antibodies that bind soluble NaPi2b.

In some embodiments, the NaPi2b-targeted antibody disclosed herein can be connected with an agent to form a conjugate. In some embodiments, the agent is a therapeutic agent. In some embodiments, the agent is an antineoplastic agent. In some embodiments, the agent is a toxin or fragment thereof. In some embodiments, the agent is (a) an auristatin compound; (b) a calicheamicin compound; (c) a duocarmycin compound; (d) SN38, (e) a pyrrolobenzodiazepine; (f) a vinca compound; (g) a tubulysin compound; (h) a non-natural camptothecin compound; (i) a maytansinoid compound; (j) a DNA binding drug; (k) a kinase inhibitor; (l) a MEK inhibitor; (m) a KSP inhibitor; (n) a topoisomerase inhibitor; (o) a DNA-alkylating drug; (p) a RNA polymerase inhibitor; or analogues thereof. In some embodiments, the agent is conjugated to the NaPi2b-targeted antibody via a linker. In some embodiments, the linker is a cleavable linker. In some embodiments, the linker is a non-cleavable linker. In some embodiments, the agent is any of the toxins described herein.

In one aspect, the NaPi2b-targeted antibody conjugate described herein includes an isolated NaPi2b-targeted antibody, connected directly or indirectly to one or more therapeutic or diagnostic agents ("D"). In some embodiments, the NaPi2b-targeted antibody conjugate also includes one or more polymeric scaffolds connected to the antibody, wherein each of the one or more D is independently connected to the antibody via the one or more polymeric scaffolds.

In some embodiments, each of the one or more polymeric scaffolds that are connected to the isolated NaPi2b-targeted antibody, independently, comprises poly(1-hydroxymethylethylene hydroxymethyl-formal) (PHF), e.g., PHF having a molecular weight ranging from about 2 kDa to about 40 kDa.

In some embodiments, each of the one or more polymeric scaffolds independently is of Formula (Ic):

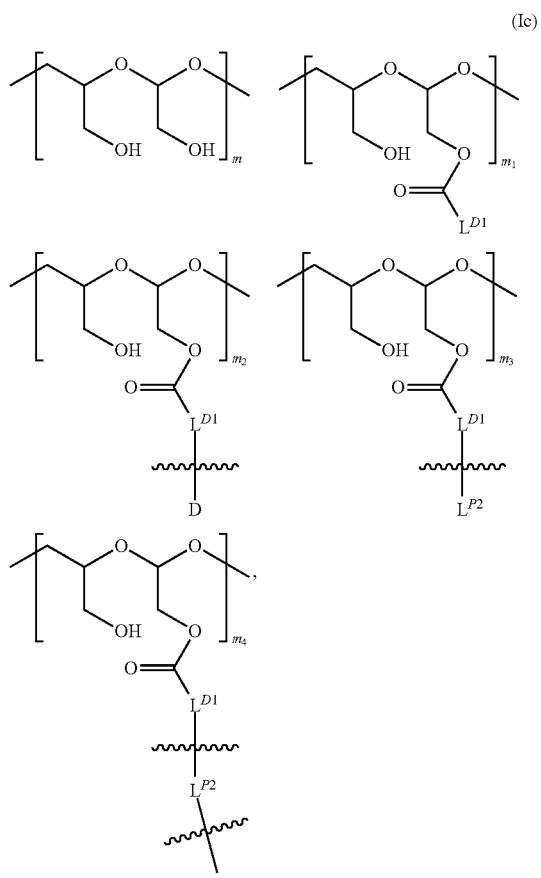

wherein:

$L^{D1}$ is a carbonyl-containing moiety;

each occurrence of

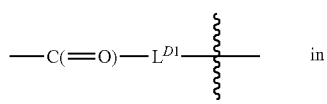 in

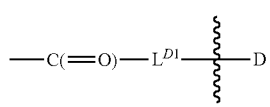

is independently a first linker that contains a biodegradable bond so that when the bond is broken, D is released in an active form for its intended therapeutic effect; and the

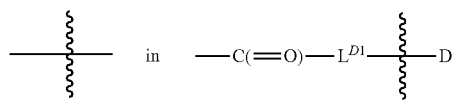

between $L^{D1}$ and D denotes direct or indirect attachment of D to $L^{D1}$;

each occurrence of

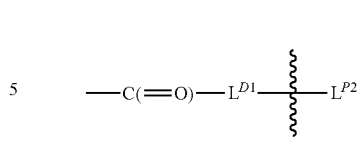

is independently a second linker not yet connected to the isolated antibody, in which $L^{P2}$ is a moiety containing a functional group that is yet to form a covalent bond with a functional group of the isolated antibody and the

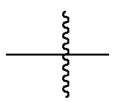

between $L^{D1}$ and $L^{P2}$ denotes direct or indirect attachment of $L^{P2}$ to $L^{D1}$, and each occurrence of the second linker is distinct from each occurrence of the first linker;

each occurrence of

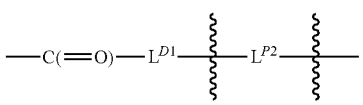

is independently a third linker that connects each D-carrying polymeric scaffold to the isolated antibody in which the terminal

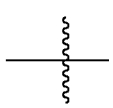

attached to $L^{P2}$ denotes direct or indirect attachment of $L^{P2}$ to the isolated antibody upon formation of a covalent bond between a functional group of $L^{P2}$ and a functional group of the isolated antibody; and each occurrence of the third linker is distinct from each occurrence of the first linker;

m is an integer from 1 to about 300,
$m_1$ is an integer from 1 to about 140,
$m_2$ is an integer from 1 to about 40,
$m_3$ is an integer from 0 to about 18,
$m_4$ is an integer from 1 to about 10;
the sum of m, $m_1$, $m_2$, $m_3$, and $m_4$ ranges from about 15 to about 300; and the total number of $L^{P2}$ connected to the isolated antibody is 10 or less.

The conjugate described herein can include one or more of the following features:

For example, in Formula (Ic), the isolated NaPi2b-targeted antibody has a molecular weight of 40 kDa or greater (e.g., 60 kDa or greater, 80 kDa or greater, 100 kDa or greater, 120 kDa or greater, 140 kDa or greater, 160 kDa or greater, 180 kDa or greater, or 200 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, 100-140 kDa, or 140-150 kDa).

In some embodiments, the isolated NaPi2b-targeted antibody or any antibody of the disclosure, including, by way of non-limiting example, the XMT 1535 antibody and the 10H1.11.4B antibody described herein.

For example, in Formula (Ic), the isolated NaPi2b-targeted antibody specifically binds to an epitope of human NaPi2b. In some embodiments, the isolated antibody specifically binds to an epitope on the extracellular domain of human NaPi2b.

For example, in Formula (Ic), the isolated NaPi2b-targeted antibody is the XMT 1535 antibody and/or the 10H1.11.4B antibody described herein, as well as biosimilars thereof. Alternatively, the monoclonal antibody is an antibody that binds to the same epitope and/or cross blocks an antibody of the disclosure or biosimilars thereof. These antibodies are respectively referred to herein as "NaPi2b antibodies" or "NaPi2b-targeted antibodies". NaPi2b antibodies include fully human monoclonal antibodies, as well as humanized monoclonal antibodies and chimeric antibodies. These antibodies show specificity for human NaPi2b, and they can or may modulate, block, inhibit, reduce, antagonize, neutralize or otherwise interfere with at least one NaPi2b activity.

For example, in Formula (Ic), the isolated NaPi2b-targeted antibody is a monoclonal antibody.

For example, in Formula (Ic), the isolated NaPi2b-targeted antibody is a rabbit, mouse, chimeric, humanized or fully human monoclonal antibody.

For example, in Formula (Ic), the isolated NaPi2b-targeted antibody is an IgG isotype. In some embodiments, the isolated NaPi2b-targeted antibody is an IgG1 isotype.

For example, in Formula (Ic), the isolated NaPi2b-targeted antibody includes a variable heavy chain complementarity determining region 1 (CDRH1) comprising an amino acid sequence at least 90%, 91%, 92%, 93%, 94%, 95%, 96%, 97% 98%, 99% or more identical to the amino acid sequence GYTFTGYNIH (SEQ ID NO: 5); a variable heavy chain complementarity determining region 2 (CDRH2) comprising an amino acid sequence at least 90%, 91%, 92%, 93%, 94%, 95%, 96%, 97% 98%, 99% or more identical to the amino acid sequence AIYPGNGDTSYKQKFRG (SEQ ID NO: 6); and a variable heavy chain complementarity determining region 3 (CDRH3) comprising an amino acid sequence at least 90%, 91%, 92%, 93%, 94%, 95%, 96%, 97% 98%, 99% or more identical to the amino acid sequence GETARATFAY (SEQ ID NO: 7). For example, in Formula (Ic), the isolated NaPi2b-targeted antibody includes a variable light chain complementarity determining region 1 (CDRL1) comprising an amino acid sequence at least 90%, 91%, 92%, 93%, 94%, 95%, 96%, 97% 98%, 99% or more identical to the amino acid sequence SASQDIGNFLN (SEQ ID NO: 8); a variable light chain complementarity determining region 2 (CDRL2) comprising an amino acid sequence at least 90%, 91%, 92%, 93%, 94%, 95%, 96%, 97% 98%, 99% or more identical to the amino acid sequence YTSSLYS (SEQ ID NO: 9); and a variable light chain complementarity determining region 3 (CDRL3) comprising an amino acid sequence at least 90%, 91%, 92%, 93%, 94%, 95%, 96%, 97% 98%, 99% or more identical to the amino acid sequence QQYSKLPLT (SEQ ID NO: 10).

For example, in Formula (Ic), the isolated NaPi2b-targeted antibody includes a CDRH1 comprising an amino acid sequence at least 90%, 91%, 92%, 93%, 94%, 95%, 96%, 97% 98%, 99% or more identical to the amino acid sequence GYTFTGYNIH (SEQ ID NO: 5); a CDRH2 comprising an amino acid sequence at least 90%, 91%, 92%, 93%, 94%, 95%, 96%, 97% 98%, 99% or more identical to the amino acid sequence AIYPGNGDTSYKQKFRG (SEQ ID NO: 6); a CDRH3 comprising an amino acid sequence at least 90%, 91%, 92%, 93%, 94%, 95%, 96%, 97% 98%, 99% or more identical to the amino acid sequence GETARATFAY (SEQ ID NO: 7); a CDRL1 comprising an amino acid sequence at least 90%, 91%, 92%, 93%, 94%, 95%, 96%, 97% 98%, 99% or more identical to the amino acid sequence SASQDIGNFLN (SEQ ID NO: 8); a CDRL2 comprising an amino acid sequence at least 90%, 91%, 92%, 93%, 94%, 95%, 96%, 97% 98%, 99% or more identical to the amino acid sequence YTSSLYS (SEQ ID NO: 9); and a CDRL3 comprising an amino acid sequence at least 90%, 91%, 92%, 93%, 94%, 95%, 96%, 97% 98%, 99% or more identical to the amino acid sequence QQYSKLPLT (SEQ ID NO: 10).

For example, in Formula (Ic), the isolated NaPi2b-targeted antibody includes a variable heavy chain complementarity determining region 1 (CDRH1) comprising the amino acid sequence GYTFTGYNIH (SEQ ID NO: 5); a variable heavy chain complementarity determining region 2 (CDRH2) comprising the amino acid sequence AIYPGNGDTSYKQKFRG (SEQ ID NO: 6); and a variable heavy chain complementarity determining region 3 (CDRH3) comprising the amino acid sequence GETARATFAY (SEQ ID NO: 7). For example, in Formula (Ic), the isolated NaPi2b-targeted antibody includes a variable light chain complementarity determining region 1 (CDRL1) comprising the amino acid sequence SASQDIGNFLN (SEQ ID NO: 8); a variable light chain complementarity determining region 2 (CDRL2) comprising the amino acid sequence YTSSLYS (SEQ ID NO: 9); and a variable light chain complementarity determining region 3 (CDRL3) comprising the amino acid sequence QQYSKLPLT (SEQ ID NO: 10).

For example, in Formula (Ic), the isolated NaPi2b-targeted antibody includes a CDRH1 comprising the amino acid sequence GYTFTGYNIH (SEQ ID NO: 5); a CDRH2 comprising the amino acid sequence AIYPGNGDTSYKQKFRG (SEQ ID NO: 6); a variable CDRH3 comprising the amino acid sequence GETARATFAY (SEQ ID NO: 7); a CDRL1 comprising the amino acid sequence SASQDIGNFLN (SEQ ID NO: 8); a CDRL2 comprising the amino acid sequence YTSSLYS (SEQ ID NO: 9); and a CDRL3 comprising the amino acid sequence QQYSKLPLT (SEQ ID NO: 10).

For example, in Formula (Ic), the isolated NaPi2b-targeted antibody includes a variable heavy chain (VH) region comprising an amino acid sequence at least 90%, 91%, 92%, 93%, 94%, 95%, 96%, 97% 98%, 99% or more identical to the amino acid sequence of SEQ ID NO: 3. For example, in Formula (Ic), the isolated NaPi2b-targeted antibody includes a variable light chain (VL) region comprising an amino acid sequence at least 90%, 91%, 92%, 93%, 94%, 95%, 96%, 97% 98%, 99% or more identical to the amino acid sequence of SEQ ID NO: 4.

For example, in Formula (Ic), the isolated NaPi2b-targeted antibody includes a VH region comprising an amino acid sequence at least 90%, 91%, 92%, 93%, 94%, 95%, 96%, 97% 98%, 99% or more identical to the amino acid sequence of SEQ ID NO: 3, and a VL region comprising an amino acid sequence at least 90%, 91%, 92%, 93%, 94%, 95%, 96%, 97% 98%, 99% or more identical to the amino acid sequence of SEQ ID NO: 4.

For example, in Formula (Ic), the isolated NaPi2b-targeted antibody includes a variable heavy chain (VH) region comprising the amino acid sequence of SEQ ID NO: 3. In some embodiments, the antibodies used in the antibody-drug conjugates disclosed herein thereof used in the antibody-drug conjugates disclosed herein include a variable light chain (VL) region comprising the amino acid sequence of SEQ ID NO: 4.

For example, in Formula (Ic), the isolated NaPi2b-targeted antibody includes a VH region comprising the amino acid sequence of SEQ ID NO: 3, and a VL region comprising the amino acid sequence of SEQ ID NO: 4.

For example, in Formula (Ic), the isolated NaPi2b-targeted antibody includes a heavy chain comprising an amino acid sequence at least 90%, 91%, 92%, 93%, 94%, 95%, 96%, 97% 98%, 99% or more identical to the amino acid sequence of SEQ ID NO: 1. For example, in Formula (Ic), the isolated NaPi2b-targeted antibody includes a light chain comprising an amino acid sequence at least 90%, 91%, 92%, 93%, 94%, 95%, 96%, 97% 98%, 99% or more identical to the amino acid sequence of SEQ ID NO: 2.

For example, in Formula (Ic), the isolated NaPi2b-targeted antibody includes a heavy chain comprising an amino acid sequence at least 90%, 91%, 92%, 93%, 94%, 95%, 96%, 97% 98%, 99% or more identical to the amino acid sequence of SEQ ID NO: 1, and a light chain comprising an amino acid sequence at least 90%, 91%, 92%, 93%, 94%, 95%, 96%, 97% 98%, 99% or more identical to the amino acid sequence of SEQ ID NO: 2.

For example, in Formula (Ic), the isolated NaPi2b-targeted antibody includes a heavy chain comprising the amino acid sequence of SEQ ID NO: 1. For example, in Formula (Ic), the isolated NaPi2b-targeted antibody includes a light chain comprising the amino acid sequence of SEQ ID NO: 2.

For example, in Formula (Ic), the isolated NaPi2b-targeted antibody includes a heavy chain comprising the amino acid sequence of SEQ ID NO: 1, and a light chain comprising the amino acid sequence of SEQ ID NO: 2.

For example, in Formula (Ic), the isolated NaPi2b-targeted antibody includes a variable heavy chain complementarity determining region 1 (CDRH1) comprising an amino acid sequence at least 90%, 91%, 92%, 93%, 94%, 95%, 96%, 97% 98%, 99% or more identical to the amino acid sequence GFSFSDFAMS (SEQ ID NO: 18); a variable heavy chain complementarity determining region 2 (CDRH2) comprising an amino acid sequence at least 90%, 91%, 92%, 93%, 94%, 95%, 96%, 97% 98%, 99% or more identical to the amino acid sequence ATIGRVAFHTYYPDSMKG (SEQ ID NO: 19); and a variable heavy chain complementarity determining region 3 (CDRH3) comprising an amino acid sequence at least 90%, 91%, 92%, 93%, 94%, 95%, 96%, 97% 98%, 99% or more identical to the amino acid sequence ARHRGFDVGHFDF (SEQ ID NO: 20). For example, in Formula (Ic), the isolated NaPi2b-targeted antibody includes a variable light chain complementarity determining region 1 (CDRL1) comprising an amino acid sequence at least 90%, 91%, 92%, 93%, 94%, 95%, 96%, 97% 98%, 99% or more identical to the amino acid sequence RSSETLVHSSGNTYLE (SEQ ID NO: 21); a variable light chain complementarity determining region 2 (CDRL2) comprising an amino acid sequence at least 90%, 91%, 92%, 93%, 94%, 95%, 96%, 97% 98%, 99% or more identical to the amino acid sequence RVSNRFS (SEQ ID NO: 22); and a variable light chain complementarity determining region 3 (CDRL3) comprising an amino acid sequence at least 90%, 91%, 92%, 93%, 94%, 95%, 96%, 97% 98%, 99% or more identical to the amino acid sequence FQGSFNPLT (SEQ ID NO: 23).

For example, in Formula (Ic), the isolated NaPi2b-targeted antibody includes a CDRH1 comprising an amino acid sequence at least 90%, 91%, 92%, 93%, 94%, 95%, 96%, 97% 98%, 99% or more identical to the amino acid sequence GFSFSDFAMS (SEQ ID NO: 18); a CDRH2 comprising an amino acid sequence at least 90%, 91%, 92%, 93%, 94%, 95%, 96%, 97% 98%, 99% or more identical to the amino acid sequence ATIGRVAFHTYYPDSMKG (SEQ ID NO: 19); a CDRH3 comprising an amino acid sequence at least 90%, 91%, 92%, 93%, 94%, 95%, 96%, 97% 98%, 99% or more identical to the amino acid sequence ARHRGFDVGHFDF (SEQ ID NO: 20); a CDRL1 comprising an amino acid sequence at least 90%, 91%, 92%, 93%, 94%, 95%, 96%, 97% 98%, 99% or more identical to the amino acid sequence RSSETLVHSSGNTYLE (SEQ ID NO: 21); a CDRL2 comprising an amino acid sequence at least 90%, 91%, 92%, 93%, 94%, 95%, 96%, 97% 98%, 99% or more identical to the amino acid sequence RVSNRFS (SEQ ID NO: 22); and a CDRL3 comprising an amino acid sequence at least 90%, 91%, 92%, 93%, 94%, 95%, 96%, 97% 98%, 99% or more identical to the amino acid sequence FQGSFNPLT (SEQ ID NO: 23).

For example, in Formula (Ic), the isolated NaPi2b-targeted antibody includes a variable heavy chain complementarity determining region 1 (CDRH1) comprising the amino acid sequence GFSFSDFAMS (SEQ ID NO: 18); a variable heavy chain complementarity determining region 2 (CDRH2) comprising the amino acid sequence ATIGRVAFHTYYPDSMKG (SEQ ID NO: 19); and a variable heavy chain complementarity determining region 3 (CDRH3) comprising the amino acid sequence ARHRGFDVGHFDF (SEQ ID NO: 20). For example, in Formula (Ic), the isolated NaPi2b-targeted antibody includes a variable light chain complementarity determining region 1 (CDRL1) comprising the amino acid sequence RSSETLVHSSGNTYLE (SEQ ID NO: 21); a variable light chain complementarity determining region 2 (CDRL2) comprising the amino acid sequence RVSNRFS (SEQ ID NO: 22); and a variable light chain complementarity determining region 3 (CDRL3) comprising the amino acid sequence FQGSFNPLT (SEQ ID NO: 23).

For example, in Formula (Ic), the isolated NaPi2b-targeted antibody includes a CDRH1 comprising the amino acid sequence GFSFSDFAMS (SEQ ID NO: 18); a CDRH2 comprising the amino acid sequence ATIGRVAFHTYYPDSMKG (SEQ ID NO: 19); a CDRH3 comprising the amino acid sequence ARHRGFDVGHFDF (SEQ ID NO: 20); a CDRL1 comprising the amino acid sequence RSSETLVHSSGNTYLE (SEQ ID NO: 21); a CDRL2 comprising the amino acid sequence RVSNRFS (SEQ ID NO: 22); and a CDRL3 comprising the amino acid sequence FQGSFNPLT (SEQ ID NO: 23).

For example, in Formula (Ic), the isolated NaPi2b-targeted antibody includes a variable heavy chain (VH) region comprising an amino acid sequence at least 90%, 91%, 92%, 93%, 94%, 95%, 96%, 97% 98%, 99% or more identical to the amino acid sequence of SEQ ID NO: 16. For example, in Formula (Ic), the isolated NaPi2b-targeted antibody includes a variable light chain (VL) region comprising an amino acid sequence at least 90%, 91%, 92%, 93%, 94%, 95%, 96%, 97% 98%, 99% or more identical to the amino acid sequence of SEQ ID NO: 17.

For example, in Formula (Ic), the isolated NaPi2b-targeted antibody includes a VH region comprising an amino acid sequence at least 90%, 91%, 92%, 93%, 94%, 95%, 96%, 97% 98%, 99% or more identical to the amino acid sequence of SEQ ID NO: 16, and a VL region comprising an amino acid sequence at least 90%, 91%, 92%, 93%, 94%, 95%, 96%, 97% 98%, 99% or more identical to the amino acid sequence of SEQ ID NO: 17.

For example, in Formula (Ic), the isolated NaPi2b-targeted antibody includes a variable heavy chain (VH) region comprising the amino acid sequence of SEQ ID NO: 16. For example, in Formula (Ic), the isolated NaPi2b-targeted antibody includes a variable light chain (VL) region comprising the amino acid sequence of SEQ ID NO: 17.

For example, in Formula (Ic), the isolated NaPi2b-targeted antibody includes a VH region comprising the amino acid sequence of SEQ ID NO: 16, and a VL region comprising the amino acid sequence of SEQ ID NO: 17.

For example, in Formula (Ic), the isolated NaPi2b-targeted antibody includes a heavy chain comprising an amino acid sequence at least 90%, 91%, 92%, 93%, 94%, 95%, 96%, 97% 98%, 99% or more identical to the amino acid sequence of SEQ ID NO: 14. For example, in Formula (Ic), the isolated NaPi2b-targeted antibody includes a light chain comprising an amino acid sequence at least 90%, 91%, 92%, 93%, 94%, 95%, 96%, 97% 98%, 99% or more identical to the amino acid sequence of SEQ ID NO: 15.

For example, in Formula (Ic), the isolated NaPi2b-targeted antibody includes a heavy chain comprising an amino acid sequence at least 90%, 91%, 92%, 93%, 94%, 95%, 96%, 97% 98%, 99% or more identical to the amino acid sequence of SEQ ID NO: 14, and a light chain comprising an amino acid sequence at least 90%, 91%, 92%, 93%, 94%, 95%, 96%, 97% 98%, 99% or more identical to the amino acid sequence of SEQ ID NO: 15.

For example, in Formula (Ic), the isolated NaPi2b-targeted antibody includes a heavy chain comprising the amino acid sequence of SEQ ID NO: 14. For example, in Formula (Ic), the isolated NaPi2b-targeted antibody includes a light chain comprising the amino acid sequence of SEQ ID NO: 15.

For example, in Formula (Ic), the isolated NaPi2b-targeted antibody includes a heavy chain comprising the amino acid sequence of SEQ ID NO: 14, and a light chain comprising the amino acid sequence of SEQ ID NO: 15.

For example, in Formula (Ic), the isolated NaPi2b-targeted antibody is an isolated antibody that competes for specific binding to human NaPi2b with an isolated antibody that includes (i) a variable heavy chain complementarity determining region 1 (CDRH1) comprising the amino acid sequence GYTFTGYNIH (SEQ ID NO: 5); a variable heavy chain complementarity determining region 2 (CDRH2) comprising the amino acid sequence AIYPGNGDTSYKQKFRG (SEQ ID NO: 6); a variable heavy chain complementarity determining region 3 (CDRH3) comprising the amino acid sequence GETARATFAY (SEQ ID NO: 7); a variable light chain complementarity determining region 1 (CDRL1) comprising the amino acid sequence SASQDIGNFLN (SEQ ID NO: 8); a variable light chain complementarity determining region 2 (CDRL2) comprising the amino acid sequence YTSSLYS (SEQ ID NO: 9); and a variable light chain complementarity determining region 3 (CDRL3) comprising the amino acid sequence QQYSKLPLT (SEQ ID NO: 10) or (ii) a CDRH1 comprising the amino acid sequence GFSFSDFAMS (SEQ ID NO: 18); a CDRH2 comprising the amino acid sequence ATIGRVAFHTYYPDSMKG (SEQ ID NO: 19); a CDRH3 comprising the amino acid sequence ARHRGFDVGHFDF (SEQ ID NO: 20); a CDRL1 comprising the amino acid sequence RSSETLVHSSGNTYLE (SEQ ID NO: 21); a CDRL2 comprising the amino acid sequence RVSNRFS (SEQ ID NO: 22); and a CDRL3 comprising the amino acid sequence FQGSFNPLT (SEQ ID NO: 23).

For example, in Formula (Ic), $m_1$ is an integer from 1 to about 120 (e.g., about 1-90) and/or $m_3$ is an integer from 1 to about 10 (e.g., about 1-8).

For example, when the PHF in Formula (Ic) has a molecular weight ranging from about 6 kDa to about 20 kDa (i.e., the sum of m, $m_1$, $m_2$, $m_3$, and $m_4$ ranging from about 45 to about 150), $m_2$ is an integer from 2 to about 20, $m_3$ is an integer from 0 to about 9, $m_4$ is an integer from 1 to about 10, and/or $m_1$ is an integer from 1 to about 75 (e.g., $m_1$ being about 4-45).

For example, when the PHF in Formula (Ic) has a molecular weight ranging from about 8 kDa to about 15 kDa (i.e., the sum of m, $m_1$, $m_2$, $m_3$, and $m_4$ ranging from about 60 to about 110), $m_2$ is an integer from 2 to about 15, $m_3$ is an integer from 0 to about 7, $m_4$ is an integer from 1 to about 10, and/or $m_1$ is an integer from 1 to about 55 (e.g., $m_1$ being about 4-30).

For example, when the PHF in Formula (Ic) has a molecular weight ranging from about 2 kDa to about 20 kDa (i.e., the sum of m, $m_1$, $m_2$, $m_3$, and $m_4$ ranging from about 15 to about 150), $m_2$ is an integer from 1 to about 20, $m_3$ is an integer from 0 to about 10 (e.g., $m_3$ ranging from 0 to about 9), $m_4$ is an integer from 1 to about 8, and/or $m_1$ is an integer from 1 to about 70, and the total number of $L^{P2}$ connected to the isolated antibody ranges from about 2 to about 8 (e.g., about 2, 3, 4, 5, 6, 7, or 8).

For example, when the PHF in Formula (Ic) has a molecular weight ranging from about 3 kDa to about 15 kDa (i.e., the sum of m, $m_1$, $m_2$, $m_3$, and $m_4$ ranging from about 20 to about 110), $m_2$ is an integer from 2 to about 15, $m_3$ is an integer from 0 to about 8 (e.g., $m_3$ ranging from 0 to about 7), $m_4$ is an integer from 1 to about 8, and/or $m_1$ is an integer from 2 to about 50, and the total number of $L^{P2}$ connected to the isolated antibody ranges from about 2 to about 8 (e.g., about 2, 3, 4, 5, 6, 7, or 8).

For example, when the PHF in Formula (Ic) has a molecular weight ranging from about 5 kDa to about 10 kDa, (i.e., the sum of m, $m_1$, $m_2$, $m_3$ and $m_4$ ranges from about 40 to about 75), $m_2$ is an integer from about 2 to about 10 (e.g., $m_2$ being about 3-10), $m_3$ is an integer from 0 to about 5 (e.g., $m_3$ ranging from 0 to about 4), $m_4$ is an integer from 1 to about 8 (e.g., $m_4$ ranging from 1 to about 5), and/or $m_1$ is an integer from about 2 to about 35 (e.g., $m_1$ being about 5-35), and the total number of $L^{P2}$ connected to the isolated antibody ranges from about 2 to about 8 (e.g., about 2, 3, 4, 5, 6, 7, or 8).

For example, each occurrence of D independently is a therapeutic agent, e.g., having a molecular weight of ≤5 kDa.

For example, each occurrence of D independently is a diagnostic agent or a label.

For example, some occurrences of D independently are therapeutic agents (e.g., having a molecular weight of ≤5 kDa) and the other occurrences of D are diagnostic agents or labels.

For example, each occurrence of D independently is an anti-cancer drug, for example, selected from vinca alkaloids, auristatins, tubulysins, duocarmycins, non-natural camptothecin compounds, maytansinoids, calicheamicin compounds, topoisomerase inhibitors, pyrrolobenzodiazepines, DNA binding drugs, DNA-alkylating drugs, RNA polymerase inhibitors, kinase inhibitors, MEK inhibitors, KSP inhibitors, and analogs thereof.

For example, each occurrence of the auristatin compound is auristatin, dolastatin (e.g., dolastatin 10 or dolastatin 15), monomethylauristatin E (MMAE), monomethylauristatin F (MMAF), auristatin F hydroxypropyl amide (AF HPA), monomethylauristatin F hydroxypropyl amide (AF HPA), or auristatin F phenylenediamine (AFP).

For example, each occurrence of the duocarmycin or analog thereof is duocarmycin A, duocarmycin B1, duocarmycin B2, duocarmycin C1, duocarmycin C2, duocarmycin D, duocarmycin SA, CC-1065, adozelesin, bizelesin, or carzelesin.

For example, each occurrence of the camptothecin compound is camptothecin, CPT-11 (irinotecan), SN-38, or topotecan.

For example, each occurrence of the pyrrolobenzodiazepine compound is a pyrrolobenzodiazepine monomer, a symmetrical pyrrolobenzodiazepine dimer or an unsymmetrical pyrrolobenzodiazepine dimer.

For example, each

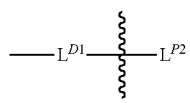

when not connected to the isolated antibody, independently comprises a terminal group $W^P$, in which each $W^P$ independently is:

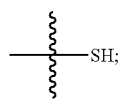
(1)

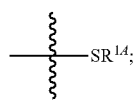
(2)

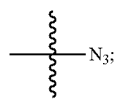
(3)

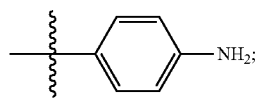
(4)

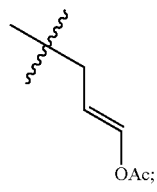
(5)

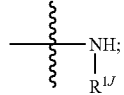
(6)

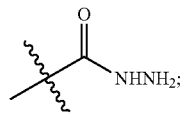
(7)

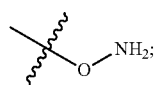
(8)

-continued

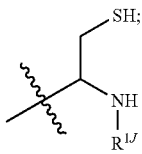
(9)

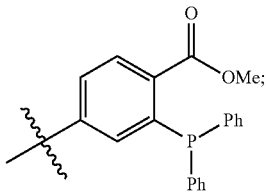
(10)

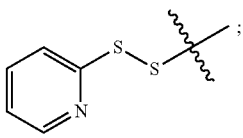
(11)

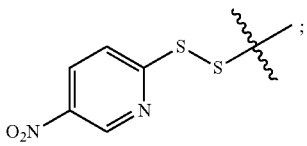
(12)

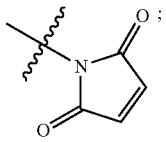
(13)

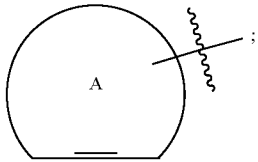
(14)

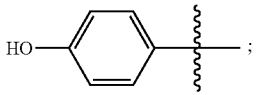
(15)

(16)

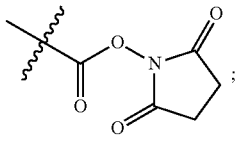
(17)

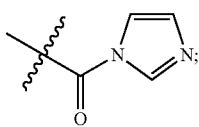
(18)

-continued

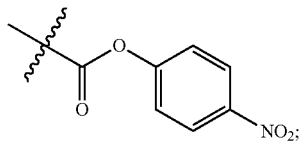
(19)

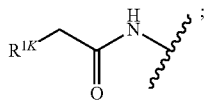
(20)

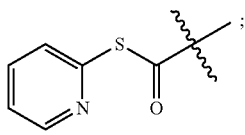
(21)

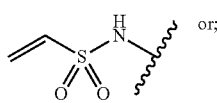
(22)

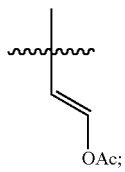
(23)

in which $R^{1K}$ is a leaving group (e.g., halide or RC(O)O— in which R is hydrogen, an aliphatic, heteroaliphatic, carbocyclic, or heterocycloalkyl moiety), $R^{1A}$ is a sulfur protecting group, and ring A is cycloalkyl or heterocycloalkyl, and $R^{1J}$ is hydrogen, an aliphatic, heteroaliphatic, carbocyclic, or heterocycloalkyl moiety.

For example, each $R^{1A}$ independently is

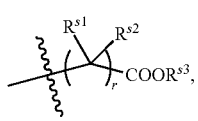 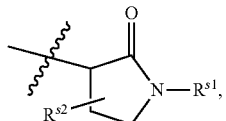

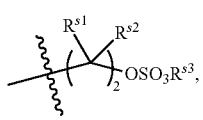 or 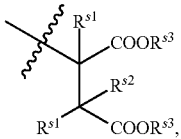

in which r is 1 or 2 and each of $R^{s1}$, $R^{s2}$, and $R^{s3}$ is hydrogen, an aliphatic, heteroaliphatic, carbocyclic, or heterocycloalkyl moiety.

For example, the functional group of $L^{P2}$ that is yet to form a covalent bond with a functional group of the isolated antibody (such as a functional group or a reactive moiety on an amino acid residue of the antibody, for example, a functional group on a cysteine residue or a lysine residue of the antibody), is selected from —$SR^P$, —S—S-LG,

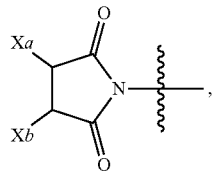

and halo, in which LG is a leaving group, $R^P$ is H or a sulfur protecting group, and one of $X_a$ and $X_b$ is H and the other is a water-soluble maleimido blocking moiety, or $X_a$ and $X_b$, together with the carbon atoms to which they are attached for a carbon-carbon double bond. For example, the functional group of $L^{P2}$ that is yet to form a covalent bond is a functional group that is not reacted with a functional group of the isolated antibody, e.g.,

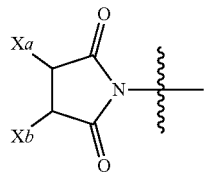

as the functional group of $L^{P2}$, in which one of $X_a$ and $X_b$ is H and the other is a water-soluble maleimido blocking moiety, or $X_a$ and $X_b$.

For example, $L^{D1}$ comprises —X—$(CH_2)_v$—C(=O)— with X directly connected to the carbonyl group of

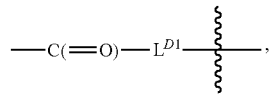

in which X is $CH_2$, O, or NH, and v is an integer from 1 to 6.

For example, each occurrence of

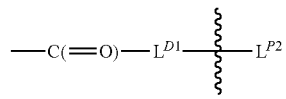

is independently —C(=O)—X—$(CH_2)_v$—C(=O)—NH—$(CH_2)_u$—NH—C(=O)—$(CH_2)_w$—$(OCH_2)_x$—NHC(=O)—$(CH_2)_y$-M, in which X is $CH_2$, O, or NH, each of v, u, w, x and y independently is an integer from 1 to 6, and M is

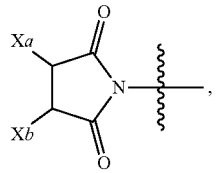

wherein one of $X_a$ and $X_b$ is H and the other is a water-soluble maleimido blocking moiety, or $X_a$ and $X_b$, together with the carbon atoms to which they are attached for a carbon-carbon double bond.

For example, each of v, u, w, x and y is 2.

For example, the ratio between D and the isolated NaPi2b-targeted antibody is about 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6; 1, 5:1, 4:1, 3:1, 2:1 or 1:1.

For example, the ratio between D and the isolated NaPi2b-targeted antibody is about 20:1, 15:1, 10:1, 5:1, 2:1 or 1:1.

For example, the ratio between D and the isolated NaPi2b-targeted antibody is about 16:1, 15:1, 14:1, 13:1, 12:1, 11:1 or 10:1.

For example, the ratio between D and the isolated NaPi2b-targeted antibody is about 15:1, 14:1, 13:1, 12:1 or 11:1.

For example, the ratio between D and the isolated NaPi2b-targeted antibody is about 15:1, 14:1, 13:1 or 12:1.

For example, the ratio between the D and the isolated NaPi2b-targeted antibody is about 6:1, 5:1, 4:1, 3:1, 2:1 or 1:1.

For example, each of the one or more D-carrying polymeric scaffolds independently is of Formula (Id):

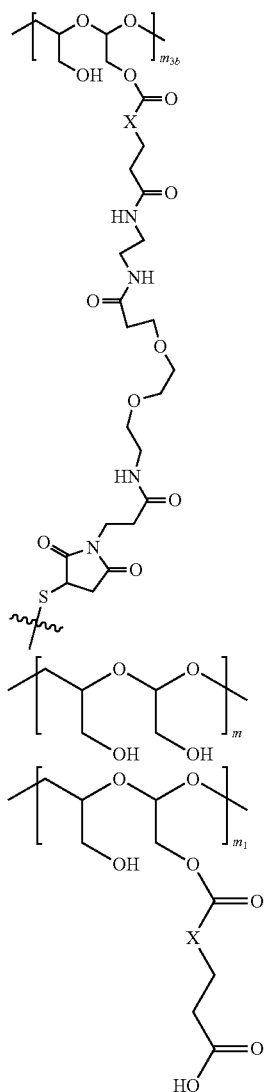

(Id)

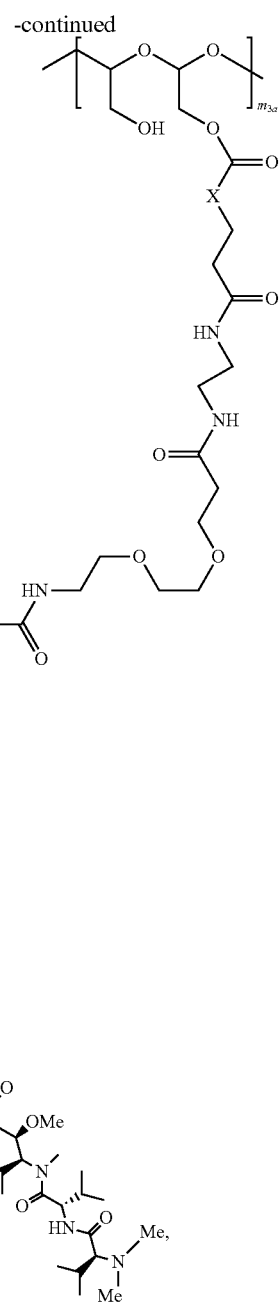

-continued wherein:
$m_{3a}$ is an integer from 0 to about 17,
$m_{3b}$ is an integer from 1 to about 8, and
the terminal

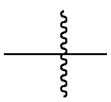

denotes the direct attachment of the one or more polymeric scaffolds to the isolated NaPi2b-targeted antibody having a molecular weight of 40 kDa or greater and (i) a variable heavy chain complementarity determining region 1 (CDRH1) comprising the amino acid sequence GYTFTGY-NIH (SEQ ID NO: 5); a variable heavy chain complementarity determining region 2 (CDRH2) comprising the amino acid sequence AIYPGNGDTSYKQKFRG (SEQ ID NO: 6); a variable heavy chain complementarity determining region 3 (CDRH3) comprising the amino acid sequence GETARATFAY (SEQ ID NO: 7); a variable light chain complementarity determining region 1 (CDRL1) comprising the amino acid sequence SASQDIGNFLN (SEQ ID NO: 8); a variable light chain complementarity determining region 2 (CDRL2) comprising the amino acid sequence YTSSLYS (SEQ ID NO: 9); and a variable light chain complementarity determining region 3 (CDRL3) comprising the amino acid sequence QQYSKLPLT (SEQ ID NO: 10) or (ii) a CDRH1 comprising the amino acid sequence GFSFSDFAMS (SEQ ID NO: 18); a CDRH2 comprising the amino acid sequence ATIGRVAFHTYYPDSMKG (SEQ ID NO: 19); a CDRH3 comprising the amino acid sequence ARHRGFDVGHFDF (SEQ ID NO: 20); a CDRL1 comprising the amino acid sequence RSSETLVHSSGNTYLE (SEQ ID NO: 21); a CDRL2 comprising the amino acid sequence RVSNRFS (SEQ ID NO: 22); and a CDRL3 comprising the amino acid sequence FQGSFNPLT (SEQ ID NO: 23).

In some embodiments, the isolated NaPi2b-targeted antibody has a molecular weight of 40 kDa or greater and includes (i) a CDRH1 comprising the amino acid sequence GYTFTGYNIH (SEQ ID NO: 5); a CDRH2 comprising the amino acid sequence AIYPGNGDTSYKQKFRG (SEQ ID NO: 6); a CDRH3 comprising the amino acid sequence GETARATFAY (SEQ ID NO: 7); a CDRL1 comprising the amino acid sequence SASQDIGNFLN (SEQ ID NO: 8); a CDRL2 comprising the amino acid sequence YTSSLYS (SEQ ID NO: 9); and a CDRL3 comprising the amino acid sequence QQYSKLPLT (SEQ ID NO: 10).

In some embodiments, the isolated NaPi2b-targeted antibody has a molecular weight of 40 kDa or greater and includes a CDRH1 comprising the amino acid sequence GFSFSDFAMS (SEQ ID NO: 18); a CDRH2 comprising the amino acid sequence ATIGRVAFHTYYPDSMKG (SEQ ID NO: 19); a CDRH3 comprising the amino acid sequence ARHRGFDVGHFDF (SEQ ID NO: 20); a CDRL1 comprising the amino acid sequence RSSETLVHSSGNTYLE (SEQ ID NO: 21); a CDRL2 comprising the amino acid sequence RVSNRFS (SEQ ID NO: 22); and a CDRL3 comprising the amino acid sequence FQGSFNPLT (SEQ ID NO: 23).

The scaffold of Formula (Id) can include one or more of the following features:

The sum of $m_{3a}$ and $m_{3b}$ is between 1 and 18.

When the PHF in Formula (Id) has a molecular weight ranging from about 2 kDa to about 40 kDa, the sum of m, $m_1$, $m_2$, $m_{3a}$ and $m_{3b}$ ranges from about 15 to about 300, $m_1$ is an integer from 1 to about 140, $m_2$ is an integer from 1 to about 40, $m_{3a}$ is an integer from 0 to about 17, $m_{3b}$ is an integer from 1 to about 8, the sum of $m_{3a}$ and $m_{3b}$ ranges from 1 and about 18, and the ratio between the PHF and the isolated NaPi2b-targeted antibody is 10 or less.

When the PHF in Formula (Id) has a molecular weight ranging from about 2 kDa to about 20 kDa, the sum of m, $m_1$, $m_2$, $m_{3a}$ and $m_{3b}$ ranges from about 15 to about 150, $m_1$ is an integer from 1 to about 70, $m_2$ is an integer from 1 to about 20, $m_{3a}$ is an integer from 0 to about 9, $m_{3b}$ is an integer from 1 to about 8, the sum of $m_{3a}$ and $m_{3b}$ ranges from 1 and about 10, and the ratio between the PHF and the isolated NaPi2b-targeted antibody is an integer from 2 to about 8.

When the PHF in Formula (Id) has a molecular weight ranging from about 3 kDa to about 15 kDa, the sum of m, $m_1$, $m_2$, $m_{3a}$ and $m_{3b}$ ranges from about 20 to about 110, $m_1$ is an integer from 2 to about 50, $m_2$ is an integer from 2 to about 15, $m_{3a}$ is an integer from 0 to about 7, $m_{3b}$ is an integer from 1 to about 8, the sum of $m_{3a}$ and $m_{3b}$ ranges from 1 and about 8; and the ratio between the PHF and the isolated NaPi2b-targeted antibody is an integer from 2 to about 8 (e.g., from about 2 to about 6 or from about 2 to about 4).

When the PHF in Formula (Id) has a molecular weight ranging from about 5 kDa to about 10 kDa, the sum of m, $m_1$, $m_2$, $m_{3a}$ and $m_{3b}$ ranges from about 40 to about 75, $m_1$ is an integer from about 2 to about 35, $m_2$ is an integer from about 2 to about 10, $m_{3a}$ is an integer from 0 to about 4, $m_{3b}$ is an integer from 1 to about 5, the sum of $m_{3a}$ and $m_{3b}$ ranges from 1 and about 5; and the ratio between the PHF and the isolated NaPi2b-targeted antibody is an integer from 2 to about 8 (e.g., from about 2 to about 6 or from about 2 to about 4).

In certain embodiments, the ratio between auristatin F hydroxypropyl amide ("AF HPA") and the isolated NaPi2b-targeted antibody can be about 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In certain embodiments, the ratio between AF HPA and the isolated NaPi2b-targeted antibody can be about 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In other embodiments, the ratio between AF HPA and the isolated NaPi2b-targeted antibody can be about 20:1, 19:1, 18:1, 17:1, 16:1, 15:1, 14:1, 13:1, 12:1, 11:1, 10:1, 9:1, 8:1, 7:1 or 6:1.

In some embodiments, the ratio between AF HPA and isolated NaPi2b-targeted antibody can be about 16:1, 15:1, 14:1, 13:1, 12:1, 11:1 or 10:1.

In some embodiments, the ratio between AF HPA and isolated NaPi2b-targeted antibody can be about 15:1, 14:1, 13:1, 12:1 or 11:1.

In some embodiments, the ratio between AF HPA and isolated NaPi2b-targeted antibody can be about 15:1, 14:1, 13:1 or 12:1.

In certain embodiments, the ratio between PHF and isolated NaPi2b-targeted antibody can be about 10:1, 9:1, 8:1, 7:1, 6:1, 5:1, 4:1, 3:1, 2:1 or 1:1.

In certain embodiments, the ratio between PHF and isolated NaPi2b-targeted antibody can be about 8:1, 7:1, 6:1, 5:1, 4:1, 3:1 or 2:1.

In other embodiments, the ratio between PHF and isolated NaPi2b-targeted antibody can be about 6:1, 5:1, 4:1, 3:1, 2:1 or 1:1.

In other embodiments, the ratio between PHF and isolated NaPi2b-targeted antibody can be about 6:1, 5:1, 4:1, 3:1 or 2:1.

In other embodiments, the ratio between PHF and isolated NaPi2b-targeted antibody can be about 6:1, 5:1, 4:1 or 3:1.

In some embodiments, the ratio between PHF and isolated NaPi2b-targeted antibody can be about 5:1, 4:1 or 3:1.

In some embodiments, the ratio between PHF and isolated NaPi2b-targeted antibody can be about 4:1, 3:1 or 2:1.

The water-soluble maleimido blocking moieties (e.g., $X_a$ or $X_b$) are moieties that can be covalently attached to one of the two olefin carbon atoms upon reaction of the maleimido group with a thiol-containing compound of Formula (II):

$$R_{90}-(CH_2)_d-SH \quad \quad (II)$$

wherein:

$R_{90}$ is $NHR_{91}$, OH, $COOR_{93}$, $CH(NHR_{91})COOR_{93}$ or a substituted phenyl group;

$R_{93}$ is hydrogen or $C_{1-4}$ alkyl;

$R_{91}$ is hydrogen, $CH_3$ or $CH_3CO$ and d is an integer from 1 to 3.

In one embodiment, the water-soluble maleimido blocking compound of Formula (II) can be cysteine, N-acetyl cysteine, cysteine methyl ester, N-methyl cysteine, 2-mercaptoethanol, 3-mercaptopropanoic acid, 2-mercaptoacetic acid, mercaptomethanol (i.e., $HOCH_2SH$), benzyl thiol in which phenyl is substituted with one or more hydrophilic substituents, or 3-aminopropane-1-thiol. The one or more hydrophilic substituents on phenyl comprise OH, SH, methoxy, ethoxy, COOH, CHO, $COC_{1-4}$ alkyl, $NH_2$, F, cyano, $SO_3H$, $PO_3H$, and the like.

In another aspect, the water-soluble maleimido blocking group is $-S-(CH_2)_d-R_{90}$, in which, $R_{90}$ is OH, COOH, or $CH(NHR_{91})COOR_{93}$;

$R_{93}$ is hydrogen or $CH_3$;

$R_{91}$ is hydrogen or $CH_3CO$; and d is 1 or 2.

In another embodiment, the water-soluble maleimido blocking group is $-S-CH_2-CH(NH_2)COOH$.

In certain embodiments, the conjugate described herein comprises one or more D-carrying PHF, each of which independently is of Formula (If), wherein the PHF has a molecular weight ranging from about 2 kDa to about 40 kDa:

(If)

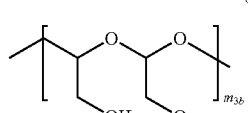
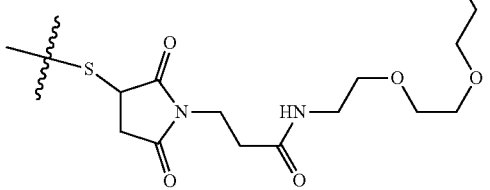
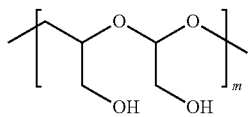
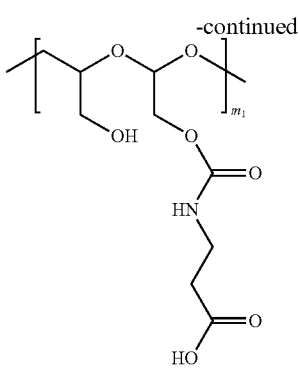
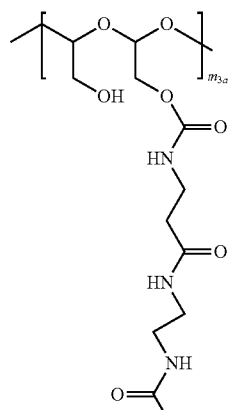
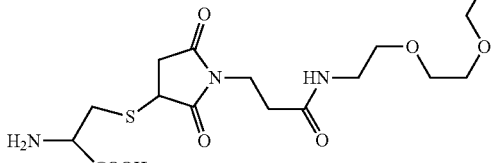
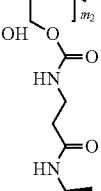
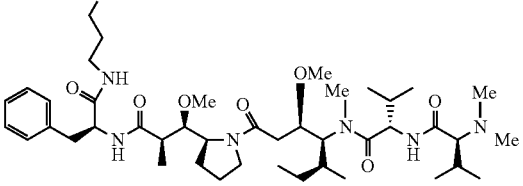

wherein:

m is an integer from 1 to about 300, $m_1$ is an integer from 1 to about 140, $m_2$ is an integer from 1 to about 40, $m_{3a}$ is an integer from 0 to about 17, $m_{3b}$ is an integer from 1 to about 8;

the sum of $m_{3a}$ and $m_{3b}$ ranges from 1 and about 18;

the sum of m, $m_1$, $m_2$, $m_{3a}$, and $m_{3b}$ ranges from about 15 to about 300;

the terminal

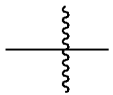

denotes the attachment of one or more PHF polymeric scaffolds to the isolated antibody that specifically binds to SLC34A2, wherein the isolated antibody that specifically binds to SLC34A2 is an isolated antibody that comprises (i) a variable heavy chain complementarity determining region 1 (CDRH1) comprising the amino acid sequence GYTFTGYNIH (SEQ ID NO: 5); a variable heavy chain complementarity determining region 2 (CDRH2) comprising the amino acid sequence AIYPGNGDTSYKQKFRG (SEQ ID NO: 6); a variable heavy chain complementarity determining region 3 (CDRH3) comprising the amino acid sequence GETARATFAY (SEQ ID NO: 7); a variable light chain complementarity determining region 1 (CDRL1) comprising the amino acid sequence SASQDIGNFLN (SEQ ID NO: 8); a variable light chain complementarity determining region 2 (CDRL2) comprising the amino acid sequence YTSSLYS (SEQ ID NO: 9); and a variable light chain complementarity determining region 3 (CDRL3) comprising the amino acid sequence QQYSKLPLT (SEQ ID NO: 10) or (ii) a CDRH1 comprising the amino acid sequence GFSFSDFAMS (SEQ ID NO: 18); a CDRH2 comprising the amino acid sequence ATIGRVAFHTYYPDSMKG (SEQ ID NO: 19); a CDRH3 comprising the amino acid sequence ARHRGFDVGHFDF (SEQ ID NO: 20); a CDRL1 comprising the amino acid sequence RSSETLVHSSGNTYLE (SEQ ID NO: 21); a CDRL2 comprising the amino acid sequence RVSNRFS (SEQ ID NO: 22); and a CDRL3 comprising the amino acid sequence FQGSFNPLT (SEQ ID NO: 23); and the ratio between the PHF and the antibody is 10 or less.

In some embodiments, the isolated NaPi2b-targeted antibody specifically binds to SLC34A2 and includes (i) a CDRH1 comprising the amino acid sequence GYTFTGYNIH (SEQ ID NO: 5); a CDRH2 comprising the amino acid sequence AIYPGNGDTSYKQKFRG (SEQ ID NO: 6); a CDRH3 comprising the amino acid sequence GETARATFAY (SEQ ID NO: 7); a CDRL1 comprising the amino acid sequence SASQDIGNFLN (SEQ ID NO: 8); a CDRL2 comprising the amino acid sequence YTSSLYS (SEQ ID NO: 9); and a CDRL3 comprising the amino acid sequence QQYSKLPLT (SEQ ID NO: 10).

In some embodiments, the isolated NaPi2b-targeted antibody specifically binds to SLC34A2 and includes a CDRH1 comprising the amino acid sequence GFSFSDFAMS (SEQ ID NO: 18); a CDRH2 comprising the amino acid sequence ATIGRVAFHTYYPDSMKG (SEQ ID NO: 19); a CDRH3 comprising the amino acid sequence ARHRGFDVGHFDF (SEQ ID NO: 20); a CDRL1 comprising the amino acid sequence RSSETLVHSSGNTYLE (SEQ ID NO: 21); a CDRL2 comprising the amino acid sequence RVSNRFS (SEQ ID NO: 22); and a CDRL3 comprising the amino acid sequence FQGSFNPLT (SEQ ID NO: 23).

The scaffold of Formula (If) can include one or more of the following features:

When the PHF in Formula (If) has a molecular weight ranging from about 2 kDa to about 20 kDa, the sum of m, $m_1$, $m_2$, $m_{3a}$ and $m_{3b}$ ranges from about 15 to about 150, $m_1$ is an integer from 1 to about 70, $m_2$ is an integer from 1 to about 20, $m_{3a}$ is an integer from 0 to about 9, $m_{3b}$ is an integer from 1 to about 8, the sum of $m_{3a}$ and $m_{3b}$ ranges from 1 and about 10, and the ratio between the PHF and the antibody is an integer from 2 to about 8.

When the PHF in Formula (If) has a molecular weight ranging from about 3 kDa to about 15 kDa, the sum of m, $m_1$, $m_2$, $m_{3a}$ and $m_{3b}$ ranges from about 20 to about 110, $m_1$ is an integer from 2 to about 50, $m_2$ is an integer from 2 to about 15, $m_{3a}$ is an integer from 0 to about 7, $m_{3b}$ is an integer from 1 to about 8, the sum of $m_{3a}$ and $m_{3b}$ ranges from 1 and about 8; and the ratio between the PHF and the antibody is an integer from 2 to about 8 (e.g., from about 2 to about 6 or from about 2 to about 4).

When the PHF in Formula (If) has a molecular weight ranging from about 5 kDa to about 10 kDa, the sum of m, $m_1$, $m_2$, $m_{3a}$ and $m_{3b}$ ranges from about 40 to about 75, $m_1$ is an integer from about 2 to about 35, $m_2$ is an integer from about 2 to about 10, $m_{3a}$ is an integer from 0 to about 4, $m_{3b}$ is an integer from 1 to about 5, the sum of $m_{3a}$ and $m_{3b}$ ranges from 1 and about 5; and the ratio between the PHF and the antibody is an integer from 2 to about 8 (e.g., from about 2 to about 6 or from about 2 to about 4).

In certain embodiments, the ratio between auristatin F hydroxypropyl amide ("AF HPA") and the antibody can be about 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In certain embodiments, the ratio between AF HPA and the antibody can be about 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In other embodiments, the ratio between AF HPA and the antibody can be about 20:1, 19:1, 18:1, 17:1, 16:1, 15:1, 14:1, 13:1, 12:1, 11:1, 10:1, 9:1, 8:1, 7:1 or 6:1.

In some embodiments, the ratio between AF HPA and the antibody can be about 16:1, 15:1, 14:1, 13:1, 12:1, 11:1 or 10:1.

In some embodiments, the ratio between AF and the antibody can be about 15:1, 14:1, 13:1, 12:1 or 11:1.

In some embodiments, the ratio between AF HPA and the antibody can be about 15:1, 14:1, 13:1 or 12:1.

In certain embodiments, the ratio between PHF and the antibody can be about 10:1, 9:1, 8:1, 7:1, 6:1, 5:1, 4:1, 3:1, 2:1 or 1:1.

In certain embodiments, the ratio between PHF and the antibody can be about 8:1, 7:1, 6:1, 5:1, 4:1, 3:1 or 2:1.

In other embodiments, the ratio between PHF and the antibody can be about 6:1, 5:1, 4:1, 3:1, 2:1 or 1:1.

In other embodiments, the ratio between PHF and the antibody can be about 6:1, 5:1, 4:1, 3:1 or 2:1.

In other embodiments, the ratio between PHF and the antibody can be about 6:1, 5:1, 4:1 or 3:1.

In some embodiments, the ratio between PHF and the antibody can be about 5:1, 4:1 or 3:1.

In some embodiments, the ratio between PHF and the antibody can be about 4:1, 3:1 or 2:1.

Another aspect of the disclosure features a method of preparing a conjugate described herein. The method includes reacting the isolated antibody with a D-carrying polymeric scaffold of Formula (Ia) such that the conjugate is formed:

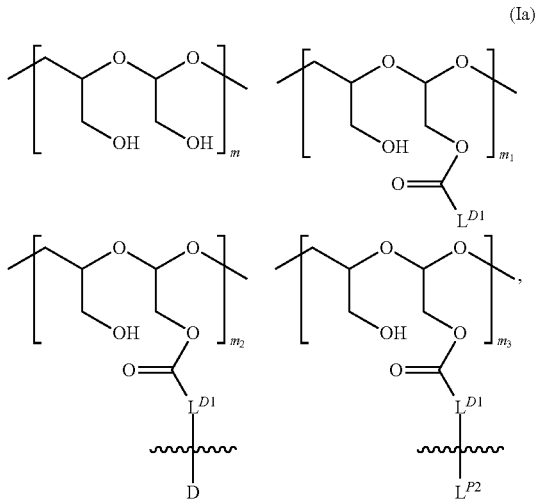

(Ia)

wherein:
$L^{D1}$ is a carbonyl-containing moiety;
each occurrence of

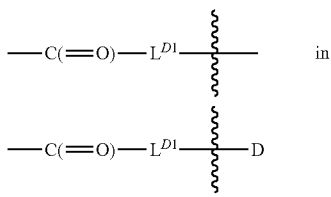

is independently a first linker that contains a biodegradable bond so that when the bond is broken, D is released in an active form for its intended therapeutic effect; and the

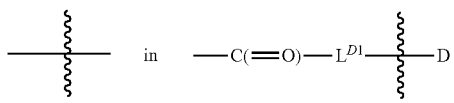

between $L^{D1}$ and D denotes direct or indirect attachment of D to $L^{D1}$;
each occurrence of

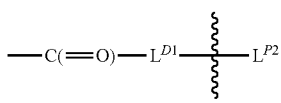

is independently a second linker not yet connected to the isolated antibody, in which $L^{P2}$ is a moiety containing a functional group that is yet to form a covalent bond with a functional group of the isolated antibody, and the

between $L^{D1}$ and $L^{P2}$ denotes direct or indirect attachment of $L^{P2}$ to $L^{D1}$, and each occurrence of the second linker is distinct from each occurrence of the first linker;
m is an integer from 1 to about 300,
$m_1$ is an integer from 1 to about 140,
$m_2$ is an integer from 1 to about 40,
$m_3$ is an integer from 1 to about 18, and
the sum of m, $m_1$, $m_2$ and $m_3$ ranges from about 15 to about 300.

In the formulae for polymeric scaffolds disclosed herein, the disconnection or gap between the polyacetal units indicates that the units can be connected to each other in any order. In other words, the appending groups that contain, e.g., D, $L^{P2}$, and the isolated antibody, can be randomly distributed along the polymer backbone.

The present disclosure also provides methods of treating, preventing, delaying the progression of or otherwise ameliorating a symptom of one or more pathologies associated with aberrant NaPi2b expression, function and/or activation or alleviating a symptom associated with such pathologies, by administering a conjugate disclosed herein to a subject in which such treatment or prevention is desired. The subject to be treated is, e.g., human. The conjugate are administered in an amount sufficient to treat, prevent or alleviate a symptom associated with the pathology.

The present disclosure also provides methods of treating, preventing, delaying the progression of or otherwise ameliorating a symptom of one or more pathologies associated with NaPi2b expression, function and/or activation or alleviating a symptom associated with such pathologies, by administering a conjugate disclosed herein to a subject in which such treatment or prevention is desired. The subject to be treated is, e.g., human. The conjugate is administered in an amount sufficient to treat, prevent or alleviate a symptom associated with the pathology.

Pathologies treated and/or prevented using the conjugates disclosed herein including, for example, a cancer. In some embodiments, the conjugates disclosed herein are useful in treating, preventing, delaying the progression of or otherwise ameliorating a NaPi2b expressing cancer. For example, the conjugates disclosed herein are useful in treating, preventing, delaying the progression of or otherwise ameliorating a symptom of a cancer selected from the group consisting of ovarian cancer (such as epithelial ovarian cancer), thyroid cancer, colorectal cancer, lung cancer, non-small cell lung cancer (NSCLC) such as non-squamous NSCLC, breast cancer, kidney cancer and salivary duct carcinoma.

In some embodiments, the conjugates disclosed herein are useful in treating, preventing, delaying the progression of or otherwise ameliorating a symptom of ovarian cancer. In some embodiments, the ovarian cancer is epithelial ovarian cancer.

In some embodiments, the conjugates disclosed herein are useful in treating, preventing, delaying the progression of or otherwise ameliorating a symptom of NSCLC. In some embodiments, the NSCLC is non-squamous NSCLC.

In some embodiments, the conjugates disclosed herein are useful in treating, preventing, delaying the progression of or otherwise ameliorating a symptom of ovarian cancer. In some embodiments, the ovarian cancer is epithelial ovarian cancer.

The disclosure also provides kits and/or methods for identifying or otherwise refining, e.g., stratifying, a patient population suitable for therapeutic administration of a NaPi2b-targeted antibody-drug conjugates disclosed herein by identifying the NaPi2b score of subject prior to treatment with a NaPi2b-targeted antibody-drug conjugate disclosed herein. In some embodiments, the subject is identified as having a scoring of 1+ or 2+ or 3+ for NaPi2b expression. In some embodiments, the test cell population is derived from fresh, unfrozen tissue from a biopsy sample. In some embodiments, the test cell population is derived from a primary or metastatic site. In some embodiments, the test cell population is derived from a frozen tissue from a biopsy or surgical sample or ascetic fluid or pleural fluid. In some embodiments, the test cell population is derived from a fixed tissue (e.g., formalin fixation) from a biopsy or surgical sample.

The IHC test measures the amount of NaPi2b receptor protein on the surface of cells in a cancer tissue sample, e.g., an ovarian cancer tissue sample or a lung cancer sample, and assigns the detected level of cell surface NaPi2b receptor NaPi2b score of 0, 1+, 2+ or 3+.

In some embodiments, the subject is refractory to chemotherapy, including standard, front-line chemotherapeutic agents.

In some embodiments, the subject has platinum-resistant ovarian cancer.

In some embodiments, the subject has platinum-sensitive ovarian cancer.

In some embodiments, the subject has platinum-refractory ovarian cancer.

In some embodiments, the subject has advanced ovarian cancer and has not received any prior therapy for treating cancer (e.g., ovarian cancer). In some embodiments, the subject has advanced ovarian cancer and has not received any prior chemotherapy for treating cancer (e.g., ovarian cancer).

The NaPi2b-targeted antibody-drug conjugates used in any of the embodiments of the methods and uses provided herein can be administered at any stage of the disease. For example, such a NaPi2b-targeted antibody-drug conjugate can be administered to a patient suffering cancer of any stage, from early to metastatic.

In some embodiments, the NaPi2b-targeted antibody-drug conjugates of the disclosure can be administered either alone or in combination with other compositions in a therapy. For instance, a conjugate of the disclosure may be co-administered with at least one additional therapeutic agent and/or adjuvant. In certain embodiments, the additional therapeutic agent is a small molecule inhibitor, another antibody-based therapy, a polypeptide or peptide-based therapy, a nucleic acid-based therapy and/or other biologic. The additional therapeutic agent can either be the same as the "D" used to form the conjugate or different.

In certain embodiments, the additional therapeutic agent is a cytotoxic agent, a chemotherapeutic agent, a growth inhibitory agent, an angiogenesis inhibitor, a PARP (poly (ADP)-ribose polymerase) inhibitor, an alkylating agent, an anti-metabolite, an anti-microtubule agent, a topoisomerase inhibitor, a cytotoxic antibiotic, any other nucleic acid damaging agent or an immune checkpoint inhibitor. In one embodiment, the therapeutic agent used in the treatment of cancer, includes but is not limited to, a platinum compound (e.g., cisplatin or carboplatin); a taxane (e.g., paclitaxel or docetaxel); a topoisomerase inhibitor (e.g., irinotecan or topotecan); an anthracycline (e.g., doxorubicin (ADRIAMYCIN®) or liposomal doxorubicin (DOXIL®)); an anti-metabolite (e.g., gemcitabine, pemetrexed); cyclophosphamide; vinorelbine (NAVELBINE®); hexamethylmelamine; ifosfamide; etoposide; an angiogenesis inhibitor (e.g., Bevacizumab (Avastin®)), thalidomide, TNP-470, platelet factor 4, interferon or endostatin); a PARP inhibitor (e.g., Olaparib (Lynparza™)); an immune checkpoint inhibitor, such as for example, a monoclonal antibody that targets either PD-1 or PD-L ((e.g., pembrolizumab (Keytruda®), atezolizumab (MPDL3280A) or nivolumab (Opdivo®)) or CTLA-4 (e.g., Ipilimumab (Yervoy®)), a kinase inhibitor (e.g., sorafenib or erlotinib), an ALK inhibitor (e.g. crizotinib (Xalkori), ceritinib (Zykadia), alectinib (Alecensa), dalantercept (ACE-041), brigatinib (AP26113), entrectinib (NMS-E628), PF-06463922 TSR-011, CEP-37440 and X-396), a proteasome inhibitor (e.g., bortezomib or carfilzomib), an immune modulating agent (e.g., lenalidomide or IL-2), a radiation agent, and/or a biosimilar thereof and/or combinations thereof. Other suitable agents include an agent considered standard of care by those skilled in the art and/or a chemotherapeutic agent well known to those skilled in the art.

In some embodiments, the immune checkpoint inhibitor suitable for the combinations and methods of the disclosure is a monoclonal antibody, a humanized antibody, a fully human antibody, a fusion protein or a combination thereof.

In some embodiments, the immune checkpoint inhibitors inhibits a checkpoint protein that comprises CTLA-4, PDL1, PDL2, PD1, BTLA, HVEM, TIM3, GAL9, LAG3, VISTA, KIR, 2B4, CD160, CGEN-15049, CHK1, CHK2, A2aR, a B-7 family ligand, CD2, CD27, CD28, CD30, CD40, CD70, CD80, CD86, CD137, CD226, CD276, DR3, GITR, HAVCR2, HVEM, IDO1, IDO2, ICOS (inducible T cell costimulator), LAIR1, LIGHT, MARCO (macrophage receptor with collagenous structure), OX-40, SLAM, TIGHT, VTCN1 or a combination thereof.

In some embodiments, the immune checkpoint inhibitor interacts with a ligand of a checkpoint protein that comprises CTLA-4, PDL1, PDL2, PD1, BTLA, HVEM, TIM3, GAL9, LAG3, VISTA, KIR, 2B4, CD160, CGEN-15049, CHK1, CHK2, A2aR, a B-7 family ligand, CD2, CD27, CD28, CD30, CD40, CD70, CD80, CD86, CD137, CD226, CD276, DR3, GITR, HAVCR2, HVEM, IDO1, IDO2, ICOS (inducible T cell costimulator), LAIR1, LIGHT, MARCO (macrophage receptor with collagenous structure), OX-40, SLAM, TIGHT, VTCN1 or a combination thereof.

In some embodiments, the immune checkpoint inhibitor inhibits a checkpoint protein that comprises CTLA-4, PDL1, PD1 or a combination thereof.

In some embodiments, the immune checkpoint inhibitor comprises pembrolizumab (MK-3475), nivolumab (BMS-936558), pidilizumab (CT-011), AMP-224, MDX-1 105, durvalumab (MEDI4736), MPDL3280A, BMS-936559, IPH2101, TSR-042, TSR-022, ipilimumab, lirilumab, atezolizumab, avelumab, tremelimumab, or a combination thereof.

In some embodiments, the immune checkpoint inhibitor comprises nivolumab (BMS-936558), ipilimumab, pembrolizumab, atezolizumab, tremelimumab, durvalumab, avelumab, or a combination thereof.

In some embodiments, the NaPi2b-targeted antibody-drug conjugate and additional agent(s) are formulated into a single therapeutic composition, and the NaPi2b-targeted antibody-drug conjugate and additional agent are administered simultaneously. Alternatively, the NaPi2b-targeted antibody-drug conjugate and additional agent are separate from each other, e.g., each is formulated into a separate therapeutic composition, and the NaPi2b-targeted antibody-drug conjugate and the additional agent are administered simultaneously, or the NaPi2b-targeted antibody-drug conjugates and the additional agent are administered at different times during a treatment regimen. For example, the NaPi2b-targeted antibody-drug conjugate is administered prior to the administration of the additional agent, the NaPi2b-targeted antibody-drug conjugate is administered subsequent to the administration of the additional agent, or the NaPi2b-targeted antibody-drug conjugate and the additional agent are administered in an alternating fashion. As described herein, the NaPi2b-targeted antibody-drug conjugate antibody and additional agent are administered in single doses or in multiple doses.

In some embodiments, the NaPi2b-targeted antibody-drug conjugate and the immune checkpoint inhibitor are formulated in the same formulation.

In some embodiments, the NaPi2b-targeted antibody-drug conjugate and the immune checkpoint inhibitor are formulated in separate formulations.

In some embodiments, the combination comprising a NaPi2b-targeted antibody-drug conjugate and an immune checkpoint inhibitor disclosed herein are useful in treating, preventing, delaying the progression of or otherwise ameliorating a symptom of ovarian cancer. In some embodiments, the ovarian cancer is epithelial ovarian cancer.

In some embodiments, the combination comprising a NaPi2b-targeted antibody-drug conjugate and an immune checkpoint inhibitor disclosed herein are useful in treating, preventing, delaying the progression of or otherwise ameliorating a symptom of NSCLC. In some embodiments, the NSCLC is non-squamous NSCLC.

Also disclosed are kits comprising a NaPi2b-targeted antibody-drug conjugate and an immune checkpoint inhibitor. The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

Pharmaceutical compositions according to the disclosure can include a NaPi2b-targeted antibody-drug conjugate disclosed herein and a suitable carrier. These pharmaceutical compositions can be included in kits, such as, for example, diagnostic kits.

One skilled in the art will appreciate that the antibodies disclosed herein have a variety of uses. For example, the proteins disclosed herein are used as therapeutic agents. The antibodies disclosed herein are also used as reagents in diagnostic kits or as diagnostic tools, or these antibodies can be used in competition assays to generate therapeutic reagents.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present invention, suitable methods and materials are described below. In the case of conflict, the present specification, including definitions, will control. In addition, the materials, methods and examples are illustrative only and are not intended to be limiting.

Other features and advantages of the invention will be apparent from the following detailed description and claims.

DETAILED DESCRIPTION

Figure 1:
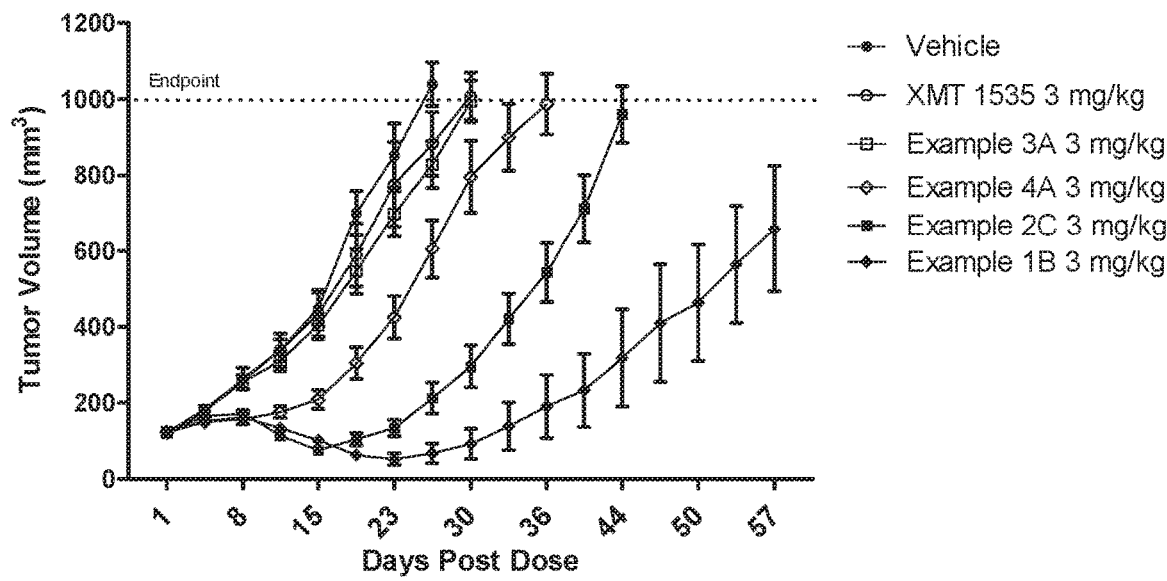
FIG. 1 illustrates the anti-tumor efficacy of XMT-1535; Example 3A, rituximab-(EG2-MI-(10 kDa PHF-BA-(AF-HPA-Ala))); Example 4A ((10H1.11.4B)-(MC-VC-PABA-MMAE)); Example 2C ((10H1.11.4B)-(EG2-MI-(10 kDa PHF-BA-(AF-HPA-Ala))) and Example 1B, XMT 1535-(EG2-MI-(10 kDa PHF-BA-(AF-HPA-Ala))), as measured in a OVCAR3 mouse tumor xenograft model.

The present disclosure provides a NaPi2b-targeted antibody-drug conjugate (such as NaPi2b antibody-polymer-drug conjugate) that is biodegradable, biocompatible and exhibits high drug load as well as specifically binding to the extracellular region of SLC34A2. The NaPi2b-targeted antibody-drug conjugates (such as NaPi2b antibody-polymer-drug conjugates) provided herein include an antibody that specifically recognizes NaPi2b, also known as sodium-dependent phosphate transport protein 2B. The NaPi2b antibodies used in the conjugates disclosed herein are capable of and useful in modulating, e.g., blocking, inhibiting, reducing, antagonizing, neutralizing or otherwise interfering with at least one biological activity of NaPi2b. Antibodies disclosed herein also include antibodies that bind soluble NaPi2b.

The NaPi2b antibody-drug conjugates provided herein include antibodies that bind to a NaPi2b epitope with an equilibrium dissociation constant ($K_d$ or $K_D$) of ≤1 µM, e.g., ≤100 nM, preferably ≤10 nM, and more preferably ≤1 nM. For example, the NaPi2b antibodies used in the antibody-drug conjugates disclosed herein exhibit a $K_d$ in the range approximately between ≤1 nM to about 1 pM.

The NaPi2b antibody-drug conjugates provided herein can include antibodies that serve to modulate, block, inhibit, reduce, antagonize, neutralize or otherwise interfere with the functional activity of NaPi2b. Functional activities of NaPi2b include for example, participating in the transcellular inorganic phosphate (Pi) absorption, thereby contributing to the maintenance of phosphate homeostasis in the body. For example, the NaPi2b antibodies completely or partially inhibit NaPi2b functional activity by partially or completely modulating, blocking, inhibiting, reducing antagonizing, neutralizing, or otherwise interfering with transcellular inorganic phosphate absorption. Transcellular inorganic phosphate absorption activity is assessed using any art-recognized method for detecting transcellular inorganic phosphate absorption activity, including, but not limited to detecting levels of transcellular inorganic phosphate absorption in the presence and absence of an anti-NaPi2b antibody disclosed herein.

The NaPi2b antibodies used in the antibody-drug conjugates disclosed herein can be those that are considered to completely modulate, block, inhibit, reduce, antagonize, neutralize or otherwise interfere with NaPi2b functional activity when the level of NaPi2b functional activity in the presence of the NaPi2b antibody is decreased by at least 95%, e.g., by 96%, 97%, 98%, 99% or 100% as compared to the level of NaPi2b functional activity in the absence of binding with a NaPi2b antibody described herein. The NaPi2b antibodies are considered to partially modulate, block, inhibit, reduce, antagonize, neutralize or otherwise interfere with NaPi2b functional activity when the level of NaPi2b activity in the presence of the NaPi2b antibody is decreased by less than 95%, e.g., 10%, 20%, 25%, 30%, 40%, 50%, 60%, 75%, 80%, 85% or 90% as compared to the level of NaPi2b activity in the absence of binding with a NaPi2b antibody described herein.

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the terms "NaPi2b" (also known as sodium-dependent phosphate transport protein 2B, SLC34A2, NaPiIIb, Npt2, Na(+)-dependent phosphate cotransporter 2B; sodium/phosphate cotransporter 2B; Na(+)/Pi cotransporter 2B; NaPi3b; solute carrier family 34 member 2), when used herein, refers to human NaPi2b (e.g., GenBank Accession No. 095436.3) and includes any variants, isoforms and species homologs of NaPi2b which are naturally expressed by cells, including tumor cells, or are expressed on cells transfected with the NaPi2b gene. These terms are synonymous and may be used interchangeably.

As used herein, the term "NaPi2b antibody" or "anti-NaPi2b antibody" is an antibody that binds specifically to the antigen NaPi2b.

When used herein in the context of two or more antibodies, the term "competes with" or "cross-competes with" indicates that the two or more antibodies compete for binding to NaPi2b, e.g., compete for NaPi2b binding in any art-recognized assay. An antibody "blocks" or "cross-blocks" one or more other antibodies from binding to NaPi2b if the antibody competes with the one or more other antibodies 25% or more, with 25%-74% representing "partial block" and 75%-100% representing "full block", as determined using any art-recognized assay. For some pairs of antibodies, competition or blocking in any art-recognized assay is only observed when one antibody is coated on the plate and the other is used to compete, and not vice versa. Unless otherwise defined or negated by context, the terms "competes with", "cross-competes with", "blocks" or "cross-blocks" when used herein is also intended to cover such pairs of antibodies.

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" "or directed against" is meant that the antibody reacts with one or more antigenic determinants of the desired antigen and does not react with other polypeptides or binds at much lower affinity ($K_d$>10$^{-6}$). Antibodies include, but are not limited to, polyclonal, monoclonal and chimeric antibodies.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as IgG$_1$, IgG$_2$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. Monoclonal antibodies (mAbs) contain an antigen-binding site capable of immunoreacting with a particular epitope of the antigen characterized by a unique binding affinity for it.

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences that are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin or fragment thereof, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is $\leq 1$ µM; e.g., $\leq 100$ nM, preferably $\leq 10$ nM and more preferably $\leq 1$ nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present disclosure is said to specifically bind to NaPi2b, when the equilibrium dissociation constant ($K_d$ or $K_D$) is $\leq 1$ µM, preferably $\leq 100$ nM, more preferably $\leq 10$ nM, and most preferably $\leq 100$ pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the disclosure include nucleic acid molecules encoding the heavy chain immunoglobulin molecules and portions thereof represented in SEQ ID NOs: 1, 3, 14, and 16, and nucleic acid molecules encoding the light chain immunoglobulin molecules and portions thereof represented in SEQ ID NOs: 2, 4, 15, and 17.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the disclosure comprise the heavy chain immunoglobulin molecules and portions thereof presented in SEQ ID NOs: 1, 3, 14, and 16, and the light chain immunoglobulin molecules and portions thereof represented in SEQ ID NOs: 2, 4, 15, and 17 as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences that are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means a polymeric boron of nucleotides of at least 10 bases in length, either ribonucleotides or deoxyribonucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides disclosed herein are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes Oligonucleotides linkages such as phosphorothioate, phosphorodithioate, phosphoroselerloate, phosphorodiselenoate, phosphoroanilothioate, phoshoraniladate, phosphoroamidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman Adv. Appl. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Green, Eds., Sinauer Associates, Sunderland7 Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present disclosure. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions that are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present disclosure, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Analogs of antibodies or immunoglobulin molecules can be readily prepared by those of ordinary skill in the art. Preferred amino- and carboxy-termini of analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the disclosure.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The use of the articles "a", "an", and "the" in both the following description and claims are to be construed to cover both the singular and the plural, unless otherwise indicated herein or clearly contradicted by context. The terms "comprising", "having", "being of" as in "being of a chemical formula", "including", and "containing" are to be construed as open terms (i.e., meaning "including but not limited to") unless otherwise noted. For example, a polymeric scaffold of a certain formula includes all the monomer units shown in the formula and may also include additional monomer units not shown in the formula. Additionally whenever "comprising" or another open-ended term is used in an embodiment, it is to be understood that the same embodiment can be more narrowly claimed using the intermediate term "consisting essentially of" or the closed term "consisting of."

The term "about", "approximately", or "approximate", when used in connection with a numerical value, means that a collection or range of values is included. For example, "about X" includes a range of values that are ±20%, ±10%, ±5%, ±2%, ±1%, ±0.5%, ±0.2%, or ±0.1% of X, where X is a numerical value. In one embodiment, the term "about" refers to a range of values which are 5% more or less than the specified value. In another embodiment, the term "about" refers to a range of values which are 2% more or less than the specified value. In another embodiment, the term "about" refers to a range of values which are 1% more or less than the specified value.

Recitation of ranges of values are merely intended to serve as a shorthand method of referring individually to each separate value falling within the range, unless otherwise indicated herein, and each separate value is incorporated into the specification as if it were individually recited herein. A range used herein, unless otherwise specified, includes the two limits of the range. For example, the expressions "x being an integer between 1 and 6" and "x being an integer of 1 to 6" both mean "x being 1, 2, 3, 4, 5, or 6", i.e., the terms "between X and Y" and "range from X to Y, are inclusive of X and Y and the integers there between.

All methods described herein can be performed in any suitable order unless otherwise indicated herein or otherwise clearly contradicted by context. The use of any and all examples, or exemplary language (e.g., "such as") provided herein, is intended merely to better illustrate the disclosure and is not to be construed as a limitation on the scope of the claims unless explicitly otherwise claimed. No language in the specification is to be construed as indicating that any non-claimed element is essential to what is claimed.

"Biocompatible" as used herein is intended to describe compounds that exert minimal destructive or host response effects while in contact with body fluids or living cells or tissues. Thus a biocompatible group, as used herein, refers to an aliphatic, cycloalkyl, heteroaliphatic, heterocycloalkyl, aryl, or heteroaryl moiety, which falls within the definition of the term biocompatible, as defined above and herein. The term "Biocompatibility" as used herein, is also taken to mean that the compounds exhibit minimal interactions with recognition proteins, e.g., naturally occurring antibodies, cell proteins, cells and other components of biological systems, unless such interactions are specifically desirable. Thus, substances and functional groups specifically intended to cause the above minimal interactions, e.g., drugs and prodrugs, are considered to be biocompatible. Preferably (with exception of compounds intended to be cytotoxic, such as, e.g., antineoplastic agents), compounds are "biocompatible" if their addition to normal cells in vitro, at concentrations similar to the intended systemic in vivo concentrations, results in less than or equal to 1% cell death during the time equivalent to the half-life of the compound in vivo (e.g., the period of time required for 50% of the compound administered in vivo to be eliminated/cleared), and their administration in vivo induces minimal and medically acceptable inflammation, foreign body reaction, immunotoxicity, chemical toxicity and/or other such adverse effects. In the above sentence, the term "normal cells" refers to cells that are not intended to be destroyed or otherwise significantly affected by the compound being tested.

"Biodegradable": As used herein, "biodegradable" polymers are polymers that are susceptible to biological processing in vivo. As used herein, "biodegradable" compounds or moieties are those that, when taken up by cells, can be broken down by the lysosomal or other chemical machinery or by hydrolysis into components that the cells can either reuse or dispose of without significant toxic effect on the cells. The term "biocleavable" as used herein has the same meaning of "biodegradable". The degradation fragments preferably induce little or no organ or cell overload or pathological processes caused by such overload or other adverse effects in vivo. Examples of biodegradation processes include enzymatic and non-enzymatic hydrolysis, oxidation and reduction. Suitable conditions for non-enzymatic hydrolysis of the biodegradable protein-polymer-drug conjugates (or their components, e.g., the biodegradable polymeric carrier and the linkers between the carrier and the antibody or the drug molecule) described herein, for example, include exposure of the biodegradable conjugates to water at a temperature and a pH of lysosomal intracellular compartment. Biodegradation of some protein-polymerdrug conjugates (or their components, e.g., the biodegradable polymeric carrier and the linkers between the carrier and the antibody or the drug molecule), can also be enhanced extracellularly, e.g., in low pH regions of the animal body, e.g., an inflamed area, in the close vicinity of activated macrophages or other cells releasing degradation facilitating factors. In certain preferred embodiments, the effective size of the polymer carrier at pH-7.5 does not detectably change over 1 to 7 days, and remains within 50% of the original polymer size for at least several weeks. At pH-5, on the other hand, the polymer carrier preferably detectably degrades over 1 to 5 days, and is completely transformed into low molecular weight fragments within a two-week to several-month time frame. Polymer integrity in such tests can be measured, for example, by size exclusion HPLC. Although faster degradation may be in some cases preferable, in general it may be more desirable that the polymer degrades in cells with the rate that does not exceed the rate of metabolization or excretion of polymer fragments by the cells. In preferred embodiments, the polymers and polymer biodegradation byproducts are biocompatible.

"Maleimido blocking compound": as used herein refers to a compound that can react with maleimide to convert it to succinimide and "maleimido blocking moiety" refers to the chemical moiety attached to the succinimide upon conversion. In certain embodiments, the maleimido blocking compound is a compound having a terminal thiol group for reacting with the maleimide. In one embodiment, the maleimido blocking compound is cysteine, N-acetyl cysteine, cysteine methyl ester, N-methyl cysteine, 2-mercaptoethanol, 3-mercaptopropanoic acid, 2-mercaptoacetic acid, mercaptomethanol (i.e., $HOCH_2SH$), benzyl thiol in which phenyl is substituted with one or more hydrophilic substituents, or 3-aminopropane-1-thiol.

"Hydrophilic": The term "hydrophilic" as it relates to substituents, e.g., on the polymer monomeric units or on a maleimido blocking moiety to render them hydrophilic or water soluble, does not essentially differ from the common meaning of this term in the art, and denotes chemical moieties which contain ionizable, polar, or polarizable atoms, or which otherwise may be solvated by water molecules. Thus a hydrophilic group, as used herein, refers to an aliphatic, cycloalkyl, heteroaliphatic, heterocycloalkyl, aryl or heteroaryl moiety, which falls within the definition of the term hydrophilic, as defined above. Examples of particular hydrophilic organic moieties which are suitable include, without limitation, aliphatic or heteroaliphatic groups comprising a chain of atoms in a range of between about one and twelve atoms, hydroxyl, hydroxyalkyl, amine, carboxyl, amide, carboxylic ester, thioester, aldehyde, nitryl, isonitryl, nitroso, hydroxylamine, mercaptoalkyl, heterocycle, carbamates, carboxylic acids and their salts, sulfonic acids and their salts, sulfonic acid esters, phosphoric acids and their salts, phosphate esters, polyglycol ethers, polyamines, polycarboxylates, polyesters and polythioesters. In certain embodiments, hydrophilic substituents comprise a carboxyl group (COOH), an aldehyde group (CHO), a ketone group ($COC_{1-4}$ alkyl), a methylol ($CH_2OH$) or a glycol (for example, $CHOH-CH_2OH$ or $CH-(CH_2OH)_2$), $NH_2$, F, cyano, $SO_3H$, $PO_3H$, and the like.

The term "hydrophilic" as it relates to the polymers disclosed herein generally does not differ from usage of this term in the art, and denotes polymers comprising hydrophilic functional groups as defined above. In a preferred embodiment, hydrophilic polymer is a water-soluble polymer. Hydrophilicity of the polymer can be directly measured through determination of hydration energy, or determined through investigation between two liquid phases, or by chromatography on solid phases with known hydrophobicity, such as, for example, C4 or C18.

"Polymeric Carrier": The term polymeric carrier, as used herein, refers to a polymer or a modified polymer, which is suitable for covalently attaching to or can be covalently attached to one or more drug molecules with a designated linker and/or one or more PBRMs with a designated linker.

"Physiological conditions": The phrase "physiological conditions", as used herein, relates to the range of chemical (e.g., pH, ionic strength) and biochemical (e.g., enzyme concentrations) conditions likely to be encountered in the extracellular fluids of living tissues. For most normal tissues, the physiological pH ranges from about 7.0 to 7.4. Circulating blood plasma and normal interstitial liquid represent typical examples of normal physiological conditions.

"Drug": As used herein, the term "drug" refers to a compound which is biologically active and provides a desired physiological effect following administration to a subject in need thereof (e.g., an active pharmaceutical ingredient).

"Anti-angiogenesis agent" or "angiogenesis inhibitor" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. The angiogenesis inhibitor includes those agents that bind and block the angiogenic activity of the angiogenic factor or its receptor. For example, an anti-angiogenesis agent is an antibody or other antagonist to an angiogenic agent as including, but not limited to, antibodies to VEGF-A or to the VEGF-A receptor (e.g., KDR receptor or Flt-1 receptor), VEGF-trap, anti-PDGFR inhibitors such as Gleevec™ (Imatinib Mesylate). Anti-angiogenesis agents also include native angiogenesis inhibitors, e.g., angiostatin, endostatin, and the like.

"Cytotoxic": As used herein the term "cytotoxic" means toxic to cells or a selected cell population (e.g., cancer cells). The toxic effect may result in cell death and/or lysis. In certain instances, the toxic effect may be a sublethal destructive effect on the cell, e.g., slowing or arresting cell growth. In order to achieve a cytotoxic effect, the drug or prodrug may be selected from a group consisting of a DNA damaging agent, a microtubule disrupting agent, or a cytotoxic protein or polypeptide, amongst others.

"Cytostatic": As used herein the term "cytostatic" refers to a drug or other compound that inhibits or stops cell growth and/or multiplication.

"Small molecule": As used herein, the term "small molecule" refers to molecules, whether naturally-occurring or artificially created (e.g., via chemical synthesis) that have a relatively low molecular weight. Preferred small molecules are biologically active in that they produce a local or systemic effect in animals, preferably mammals, more preferably humans. In certain preferred embodiments, the small molecule is a drug and the small molecule is referred to as "drug molecule" or "drug" or "therapeutic agent". In certain embodiments, the drug molecule has MW less than or equal to about 5 kDa. In other embodiments, the drug molecule has MW less than or equal to about 1.5 kDa. In embodiments, the drug molecule is selected from vinca alkaloids, auristatins, duocarmycins, tubulysins, non-natural camptothecin compounds, topoisomerase inhibitors, DNA binding drugs, kinase inhibitors, MEK inhibitors, KSP inhibitors, calicheamicins, SN38, pyrrolobenzodiazepines, and analogs thereof. Preferably, though not necessarily, the drug is one that has already been deemed safe and effective for use by an appropriate governmental agency or body, e.g., the FDA. For example, drugs for human use listed by the FDA under 21 C.F.R. §§ 330.5, 331 through 361, and 440 through 460; drugs for veterinary use listed by the FDA under 21 C.F.R. §§ 500 through 589, incorporated herein by reference, are all considered suitable for use with the present hydrophilic polymers.

"Drug derivative" or "modified drug" or the like as used herein, refers to a compound that comprises the drug molecule intended to be delivered by the conjugate disclosed herein and a functional group capable of attaching the drug molecule to the polymeric carrier.

"Active form" as used herein refers to a form of a compound that exhibits intended pharmaceutical efficacy in vivo or in vitro. In particular, when a drug molecule intended to be delivered by the conjugate disclosed herein is released from the conjugate, the active form can be the drug itself or its derivatives, which exhibit the intended therapeutic properties. The release of the drug from the conjugate can be achieved by cleavage of a biodegradable bond of the linker that attaches the drug to the polymeric carrier. The active drug derivatives accordingly can comprise a portion of the linker.

"PHF" refers to poly(1-hydroxymethylethylene hydroxymethyl-formal).

As used herein, the terms "polymer unit", "monomeric unit", "monomer", "monomer unit", "unit" all refer to a repeatable structural unit in a polymer.

As used herein, "molecular weight" or "MW" of a polymer or polymeric carrier/scaffold or polymer conjugates refers to the weight average molecular weight of the unmodified polymer unless otherwise specified.

"Immune checkpoint inhibitor" or "immune checkpoint inhibiting agent" or "immune checkpoint blocking agent" or "immune checkpoint modulator" as used herein, refers to an agent that binds an inhibitory immune checkpoint protein and blocks its activity thereby enabling the immune system to recognize tumor cells and allowing a sustained immunotherapy response. The inhibition can be competitive or non-competitive inhibition that can be steric or allosteric. In cases where an immune checkpoint protein is an immune stimulating protein, an immune checkpoint inhibitor acts to promote the activity of the immune stimulating protein, such as by binding and activating the stimulatory immune checkpoint protein or by inhibiting by interfering with, such as by binding or deactivating, inhibitors of the stimulatory immune checkpoint protein. An example of an immune checkpoint inhibitor is an anti-immune checkpoint protein antibody.

"Immune checkpoints" as used herein refer to inhibitory pathways of the immune system that are responsible for maintaining self-tolerance and modulating the duration and amplitude of physiological immune responses in peripheral tissues in order to minimize collateral tissue damage. Immune checkpoints are regulated by immune checkpoint proteins.

"Immune checkpoint protein" as used herein, refers to is a protein, typically a receptor (e.g., CTLA4 or PD-1) or a ligand (e.g., PD-L1) that regulates or modulates the extent of an immune response. The immune checkpoint proteins can be inhibitory or stimulatory. In particular, the immune checkpoint proteins are inhibitory to the activation of the immune response. Thus, inhibition of an inhibitory immune checkpoint protein acts to stimulate or activate an immune response, such as T cell activation and proliferation.

A "target" of an immune checkpoint inhibitor as used herein, is the immune checkpoint protein to which the immune checkpoint inhibitor or immune checkpoint inhibiting agent binds to block activity. Typically, the immune checkpoint inhibitor specifically binds to the target. For example, the target of the exemplary anti-CTLA4 antibody designated ipilimumab is CTLA4.

"Combination Therapy" as used herein refers to a treatment in which a subject is given two or more therapeutic agents, such as at least two or at least three therapeutic agents, for treating a single disease. For purposes herein, combination therapy includes therapy with a NaPi2b-targeted antibody-drug conjugate and an immune checkpoint inhibitor.

As used herein "co-administration", "co-administering" or "co-administered" refers to the administration of at least two different therapeutic agents sufficiently close in time. Such administration may be done in any order, including simultaneous administration, as well as temporally spaced order from a few seconds up to several days apart. Such administration may also include more than a single administration of one agent and/or independently the other agent. The administration of the agents may be by the same or different routes.

As used herein, "anti-CTLA4 antibody" refers to any antibody that specifically binds to cytotoxic T-lymphocyte-associated protein 4 (CTLA4) or a soluble fragment thereof and blocks the binding of ligands to CTLA4, thereby resulting in competitive inhibition of CTLA4 and inhibition of CTLA4-mediated inhibition of T cell activation. Hence, anti-CTLA4 antibodies are CTLA4 inhibitors. Reference to anti-CTLA4 antibodies herein include a full-length antibody and derivatives thereof, such as antigen-binding fragments thereof that specifically bind to CTLA4. Exemplary anti-CTLA4 antibodies include, but are not limited to, ipilimumab or tremelimumab, or a derivative or antigen-binding fragment thereof.

As used herein, a "cytotoxic T-lymphocyte-associated protein 4" (CTLA4; also known as CD 152) antigen refers to an inhibitory receptor of the immunoglobulin superfamily, that is bound by ligands such as CD80 (also called B7-1) and CD86, (also called B7-2). CTLA4 includes human and non-human proteins. In particular, CTLA4 antigen includes human CTLA4, which has the sequence of amino acids set forth in SEQ ID NO: 10 (see e.g., GenBank Accession No. AAL07473.1).

As used herein, "anti-PD-1 antibody" refers to any antibody that specifically binds to programmed cell death protein 1 (PD-1) or a soluble fragment thereof and blocks the binding of ligands to PD-1, thereby resulting in competitive inhibition of PD-1 and inhibition of PD-1 mediated inhibition of T cell activation. Hence, anti-PD-1 antibodies are PD-1 inhibitors. Reference to anti-PD-1 antibodies herein include a full-length antibody and derivatives thereof, such as antigen-binding fragments thereof that specifically bind to PD-1. Exemplary anti-PD-1 antibodies include, but are not limited to, nivolumab, MK-3475, pidilizumab, or a derivative or antigen-binding fragment thereof.

As used herein, a "programmed cell death protein 1" (PD-1) antigen refers to an inhibitory receptor, that is a type 1 membrane protein and is bound by ligands such as PD-L1 and PD-L2, which are members of the B7 family. PD-1 includes human and non-human proteins. In particular, PD-1 antigen includes human PD-1, which has the sequence of amino acids set forth in SEQ ID NO: 299 (see e.g., UniProt Accession No. Q15116.3). As used herein, anti-PD-L1 antibody refers to an antibody that specifically binds to programmed death-ligand 1 (PD-L1) or a soluble fragment thereof and blocking the binding of the ligand to PD-1, thereby resulting in competitive inhibition of PD-1 and inhibition of PD-1 mediated inhibition of T cell activity. Hence, anti-PD-LI antibodies are PD-1 inhibitors. Reference to anti-PD-L1 antibodies herein include a full-length antibody and derivatives thereof, such as antigen-binding fragments thereof that specifically bind to PD-L1. Exemplary anti-PD-L1 antibodies include, but are not limited to, BMS-936559, MPDL3280A, MEDI4736 or a derivative or antigen-binding fragment thereof.

As used herein, "dosing regimen" or "dosage regimen" refers to the amount of agent, for example, the composition containing a NaPi2b-targeted antibody-drug conjugate, administered, and the frequency of administration. The dosing regimen is a function of the disease or condition to be treated, and thus can vary.

As used herein, "frequency" of administration refers to the time between successive administrations of treatment. For example, frequency can be days, weeks or months. For example, frequency can be more than once weekly, for example, twice a week, three times a week, four times a week, five times a week, six times a week or: daily. Frequency also can be one, two, three or four weeks. The particular frequency is a function of the particular disease or condition treated. Generally, frequency is more than once weekly, and generally is twice weekly.

As used herein, a "cycle of administration" refers to the repeated schedule of the dosing regimen of administration of the enzyme and/or a second agent that is repeated over successive administrations. For example, an exemplary cycle of administration is a 28 day cycle with administration twice weekly for three weeks, followed by one-week of discontinued dosing.

As used herein, when referencing dosage based on mg/kg of the subject, an average human subject is considered to have a mass of about 70 kg-75 kg, such as 70 kg and a body surface area (BSA) of 1.73 m. As used herein, amelioration of the symptoms of a particular disease or disorder by a treatment, such as by administration of a pharmaceutical composition or other therapeutic, refers to any lessening, whether permanent or temporary, lasting or transient, of the symptoms or, adverse effects of a condition, such as, for example, reduction of adverse effects associated with or that occur upon administration of a NaPi2b-targeted antibody-drug conjugate.

As used herein, "treating" or "treat" describes the management and care of a patient for the purpose of combating a disease, condition, or disorder and includes the administration of a conjugate of the disclosure, or a pharmaceutical composition thereof, to alleviate the symptoms or complications of a disease, condition or disorder, or to eliminate the disease, condition or disorder.

As used herein, "prevention" or "prophylaxis" refers to reduction in the risk of developing a disease or condition, or reduction or elimination of the onset of the symptoms or complications of the disease, condition or disorder.

The term "effective amount" or "sufficient amount", as it refers to an active agent, refers to the amount necessary to elicit the desired biological response. As used herein, a "therapeutically effective amount" or a "therapeutically effective dose" refers to an amount or quantity of an agent, compound, material, or composition containing a compound that is at least sufficient to produce a detectable therapeutic effect. The effect can be detected by any assay method known in the art. The precise effective amount for a subject will depend upon the subject's body weight, size, and health; the nature and extent of the condition; and the therapeutic selected for administration.

A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

As used herein, "unit dose form" or "unit dosage form" refers to physically discrete units suitable for human and animal subjects and packaged individually as is known in the art.

As used herein, a single dosage formulation refers to a formulation as a single dose.

As used herein a "kit" refers to a combination of components, such as a combination of the compositions herein and another item for a purpose including, but not limited to, reconstitution, activation and instruments/devices for delivery, administration, diagnosis and assessment of a biological activity or property. Kits optionally include instructions of use.

The present disclosure is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The present disclosure is intended to include all isomers of the compound, which refers to and includes, optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers.

NaPi2b Antibodies

Antibody-drug conjugates disclosed herein include monoclonal antibodies that specifically recognize NaPi2b and have the ability to inhibit NaPi2b activity.

Exemplary antibodies used in the antibody-drug conjugates disclosed herein include, for example, the antibodies referred to herein as the XMT 1535 antibody and/or the 10H1.11.4B antibody. These antibodies show specificity for human NaPi2b and they have been shown to inhibit the functional activity of NaPi2b in vitro.

Each of the NaPi2b monoclonal antibodies described herein includes a heavy chain (HC), heavy chain variable region (VH), light chain (LC), and a light chain variable region (VL), as shown in the amino acid and corresponding nucleic acid sequences presented below. The variable heavy chain region and variable light chain region for each antibody are shaded in the amino acid sequences below. The complementarity determining regions (CDRs) of the heavy chain and the light chain are underlined in the amino acid sequences presented below. The amino acids encompassing the complementarity determining regions (CDRs) for the XMT 1535 antibody are as defined by E. A. Kabat et al. (See Kabat, E. A., et al., Sequences of Protein of immunological interest, Fifth Edition, US Department of Health and Human Services, US Government Printing Office (1991)) and are disclosed in U.S. Pat. No. 8,603,474, and the amino acids encompassing the CDRs for the 10H1.11.4B antibody are as defined in U.S. Pat. No. 8,535,675.

>XMT 1535 Heavy Chain Amino Acid Sequence (Heavy chain variable region (SEQ ID NO: 3)+IgG1 Heavy chain constant region (SEQ ID NO: 11))

(SEQ ID NO: 1)
QVQLVQSGAEVVKPGASVKMSCKAS<u>GYTFTGYNIH</u>WVKQAPGQGLEWIGA

<u>IYPGNGDTSYKQKFRG</u>RATLTADTSTSTVYMELSSLRSEDSAVYYCARG<u>E</u>

<u>TARATFAY</u>WGQGTLVTVSSGASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKRVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPG*

CDRH1:
(SEQ ID NO: 5)
GYTFTGYNIH

CDRH2:
(SEQ ID NO: 6)
AIYPGNGDTSYKQKFRG

CDRH3:
(SEQ ID NO: 7)
GETARATFAY

>XMT 1535 Light Chain Amino Acid Sequence (Light chain variable region (SEQ ID NO: 4)+Light chain constant region (SEQ ID NO: 12))

(SEQ ID NO: 2)
DIQMTQSPSSLSASVGDRVTITC<u>SASQDIGNFLN</u>WYQQKPGKTVKVLIY<u>Y</u>

<u>TSSLYS</u>GVPSRFSGSGSGTDYTLTISSLQPEDFATYYC<u>QQYSKLPLT</u>FGQ

<u>GTKLELKR</u>RTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

CDRL1:
(SEQ ID NO: 8)
SASQDIGNFLN

CDRL2:
(SEQ ID NO: 9)
YTSSLYS

CDRL3:
(SEQ ID NO: 10)
QQYSKLPLT

>10H1.11.4B Heavy Chain Amino Acid Sequence (Heavy chain variable region (SEQ ID NO: 16)+IgG1 Heavy chain constant region (SEQ ID NO: 13))

(SEQ ID NO: 14)
EVQLVESGGGLVQPGGSLRLSCAAS<u>GFSFSDFAMS</u>WVRQAPGKGLEWVA<u>T</u>

<u>IGRVAFHTYYPDSMKG</u>RFTISRDNSKNTLYLQMNSLRAEDTAVYYC<u>ARHR</u>

<u>GFDVGHFDF</u>WGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPG*

CDRH1:
(SEQ ID NO: 18)
GFSFSDFAMS

CDRH2:
(SEQ ID NO: 19)
ATIGRVAFHTYYPDSMKG

CDRH3:
(SEQ ID NO: 20)
ARHRGFDVGHFDF

>10H1.11.4B Light Chain Amino Acid Sequence (Light chain variable region (SEQ ID NO: 17)+Light chain constant region (SEQ ID NO: 12))

(SEQ ID NO: 15)
DIQMTQSPSSLSASVGDRVTITC<u>RSSETLVHSSGNTYLE</u>WYQQKPGKAP

KLLIY<u>RVSNRFS</u>GVPSRFSGSGSGTDFTLTISSLQPEDFATYYC<u>FQGSF</u>

<u>NPLT</u>FGQGTKVEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC*

CDRL1:
(SEQ ID NO: 21)
RSSETLVHSSGNTYLE

CDRL2:
(SEQ ID NO: 22)
RVSNRFS

CDRL3:
(SEQ ID NO: 23)
FQGSFNPLT

Also included in the disclosure are antibodies that bind to the same epitope or cross compete for binding to the same epitope as the antibodies described herein. For example, antibodies disclosed herein specifically bind to NaPi2b, wherein the antibody binds to an epitope that includes one or more amino acid residues on human NaPi2b (e.g., GenBank Accession No. 095436.3).

Antibodies disclosed herein specifically bind to an epitope on the full-length human NaPi2b comprising the amino acid sequence:

```
                                                   (SEQ ID NO: 24)
  1    MAPWPELGDA QPNPDKYLEG AAGQQPTAPD KSKETNKTDN TEAPVTKIEL

51    LPSYSTATLI DEPTEVDDPW NLPTLQDSGI KWSERDTKGK ILCFFQGIGR

101    LILLLGFLYF FVCSLDILSS AFQLVGGKMA GQFFSNSSIM SNPLLGLVIG

151    VLVTVLVQSS STSTSIVVSM VSSSLLTVRA AIPIIMGANI GTSITNTIVA

201    LMQVGDRSEF RRAFAGATVH DFFNWLSVLV LLPVEVATHY LEIITQLIVE

251    SFHFKNGEDA PDLLKVITKP FTKLIVQLDK KVISQIAMND EKAKNKSLVK

301    IWCKTFTNKT QINVTVPSTA NCTSPSLCWT DGIQNWTMKN VTYKENIAKC

351    QHIFVNFHLP DLAVGTILLI LSLLVLCGCL IMIVKILGSV LKGQVATVIK

401    KTINTDFPFP FAWLTGYLAI LVGAGMTFIV QSSSVFTSAL TPLIGIGVIT

451    IERAYPLTLG SNIGTTTTAI LAALASPGNA LRSSLQIALC HFFFNISGIL

501    LWYPIPFTRL PIRMAKGLGN ISAKYRWFAV FYLIIFFFLI PLTVFGLSLA

551    GWRVLVGVGV PVVFIIILVL CLRLLQSRCP RVLPKKLQNW NFLPLWMRSL

601    KPWDAVVSKF TGCFQMRCCC CCRVCCRACC LLCDCPKCCR CSKCCEDLEE

651    AQEGQDVPVK APETFDNITI SREAQGEVPA SDSKTECTAL
```

Antibodies disclosed herein specifically bind to an epitope on an extracellular domain (ECD) of the human NaPi2b.

Those skilled in the art will recognize that it is possible to determine, without undue experimentation, if a monoclonal antibody has the same specificity as a monoclonal antibody disclosed herein (e.g., XMT 1535, 10H1.11.4B) by ascertaining whether the former prevents the latter from binding to a natural binding partner or other molecule known to be associated with NaPi2b. If the monoclonal antibody being tested competes with the monoclonal antibody disclosed herein, as shown by a decrease in binding by the monoclonal antibody disclosed herein, then the two monoclonal antibodies bind to the same, or a closely related, epitope.

An alternative method for determining whether a monoclonal antibody has the specificity of monoclonal antibody disclosed herein is to pre-incubate the monoclonal antibody disclosed herein with soluble NaPi2b (with which it is normally reactive), and then add the monoclonal antibody being tested to determine if the monoclonal antibody being tested is inhibited in its ability to bind NaPi2b. If the monoclonal antibody being tested is inhibited then, in all likelihood, it has the same, or functionally equivalent, epitopic specificity as the monoclonal antibody disclosed herein.

Screening of monoclonal antibodies disclosed herein, can also be carried out, e.g., by measuring NaPi2b-mediated activity, and determining whether the test monoclonal antibody is able to modulate, block, inhibit, reduce, antagonize, neutralize or otherwise interfere with NaPi2b activity.

NaPi2b antibodies are generated, for example, using various procedures known within the art may be used for the production of monoclonal antibodies directed against NaPi2b, or against derivatives, fragments, analogs homologs or orthologs thereof. (See, for example, Antibodies: A Laboratory Manual, Harlow E, and Lane D, 1988, Cold Spring Harbor Laboratory Press, Cold Spring Harbor, N.Y., incorporated herein by reference). Fully human antibodies are antibody molecules in which the entire sequence of both the light chain and the heavy chain, including the CDRs, arise from human genes. Such antibodies are termed "human antibodies" or "fully human antibodies" herein. Human monoclonal antibodies are prepared, for example, using the procedures described in the Examples provided below. Human monoclonal antibodies can be also prepared by using the trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

Antibodies are purified by well-known techniques, such as affinity chromatography using protein A or protein G, which provide primarily the IgG fraction of immune serum. Subsequently, or alternatively, the specific antigen that is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

Monoclonal antibodies that modulate, block, inhibit, reduce, antagonize, neutralize or otherwise interfere with NaPi2b activity are generated, e.g., by immunizing an animal with membrane bound and/or soluble NaPi2b, such as, for example, murine, rat or human NaPi2b or an immunogenic fragment, derivative or variant thereof. Alternatively, the animal is immunized with cells transfected with a vector containing a nucleic acid molecule encoding NaPi2b such that NaPi2b is expressed and associated with the surface of the transfected cells. Alternatively, the antibodies are obtained by screening a library that contains antibody or antigen binding domain sequences for binding to NaPi2b. This library is prepared, e.g., in bacteriophage as protein or peptide fusions to a bacteriophage coat protein that is expressed on the surface of assembled phage particles and the encoding DNA sequences contained within the phage particles (i.e., "phage displayed library"). Hybridomas resulting from myeloma/B cell fusions are then screened for reactivity to NaPi2b. Additionally, the antibodies by selected from, and optionally optimized in, yeast antibody display libraries and yeast library presentation systems as described in, e.g.: Blaise L, Wehnert A, Steukers M P, van den Beucken T, Hoogenboom H R, Hufton S E. Construction and diversification of yeast cell surface displayed libraries by yeast mating: application to the affinity maturation of Fab antibody fragments. Gene. 2004 Nov. 24; 342(2):211-8; Boder E T, Wittrup K D. Yeast surface display for screening combinatorial polypeptide libraries. Nat Biotechnol. 1997 June; 15(6):553-7; Kuroda K, Ueda M. Cell surface engineering of yeast for applications in white biotechnology. Biotechnol Lett. 2011 January; 33(1): 1-9. doi: 10.1007/s10529-010-0403-9. Review; Lauer T M, Agrawal N J, Chennamsetty N, Egodage K, Helk B, Trout B L. Developability index: a rapid in silico tool for the screening of antibody aggregation propensity. J Pharm Sci. 2012 January; 101(1):102-15; Orcutt K. D. and Wittrup K. D. (2010), 207-233 doi: 10.1007/978-3-642-01144-3_15; Rakestraw J A, Aird D, Aha P M, Baynes B M, Lipovsek D. Secretion-and-capture cell-surface display for selection of target-binding proteins. Protein Eng Des Sel. 2011 June; 24(6):525-30; U.S. Pat. Nos. 8,258,082; 6,300,064; 6,696, 248; 6,165,718; 6,500,644; 6,291,158; 6,291,159; 6,096, 551; 6,368,805; 6,500,644. Exemplary yeast library presentation systems are described in, e.g., WO2008118476; WO2009/036379; WO2010105256; and WO2012009568. In certain embodiments, such yeast antibody display libraries or yeast library presentation systems are designed to mimic or reflect the diversity characteristic of the human preimmune antibody repertoire. In certain embodiments such yeast antibody display library diversity or yeast library presentation system diversity is generated in silico. In certain embodiments such yeast antibody display libraries or yeast library presentation systems comprise *Saccharomyces* yeast cells, such as *Saccharomyces Cerevisiae* cells. In certain embodiments such yeast antibody display libraries or yeast library presentation systems comprise *Pichia* cells.

Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, Monoclonal Antibodies: Principles and Practice, Academic Press, (1986) pp. 59-103). Suitable culture media for this purpose include, for example, Dulbecco's Modified Eagle's Medium and RPMI-1640 medium.

Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxyapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies disclosed herein can be readily isolated and sequenced using conventional procedures (e.g., by using oligonucleotide probes that are capable of binding specifically to genes encoding the heavy and light chains of murine antibodies). The hybridoma cells disclosed herein serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody disclosed herein, or can be substituted for the variable domains of one antigen-combining site of an antibody disclosed herein to create a chimeric bivalent antibody.

Monoclonal antibodies disclosed herein include fully human antibodies or humanized antibodies. These antibodies are suitable for administration to humans without engendering an immune response by the human against the administered immunoglobulin.

A humanized or fully human NaPi2b antibody is generated, for example, using the procedures described in the Examples provided below.

In other, alternative methods, a NaPi2b antibody is developed, for example, using phage-display methods using antibodies containing only human sequences. Such approaches are well-known in the art, e.g., in WO92/01047 and U.S. Pat. No. 6,521,404, which are hereby incorporated by reference. In this approach, a combinatorial library of phage carrying random pairs of light and heavy chains are screened using natural or recombinant source of NaPi2b. In another approach, a NaPi2b antibody can be produced by a process wherein at least one step of the process includes immunizing a transgenic, non-human animal with human NaPi2b protein. In this approach, some of the endogenous heavy and/or kappa light chain loci of this xenogeneic non-human animal have been disabled and are incapable of the rearrangement required to generate genes encoding immunoglobulins in response to an antigen. In addition, at least one human heavy chain locus and at least one human light chain locus have been stably transfected into the animal. Thus, in response to an administered antigen, the human loci rearrange to provide genes encoding human variable regions immunospecific for the antigen. Upon immunization, therefore, the XenoMouse produces B-cells that secrete fully human immunoglobulins.

A variety of techniques are well-known in the art for producing xenogeneic non-human animals. For example, see U.S. Pat. Nos. 6,075,181 and 6,150,584, which is hereby incorporated by reference in its entirety. This general strategy was demonstrated in connection with generation of the first XenoMouse™ strains as published in 1994. See Green et al. Nature Genetics 7:13-21 (1994), which is hereby incorporated by reference in its entirety. See also, U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2 and European Patent No., EP 0 463 151 B1 and International Patent Applications No. WO 94/02602, WO 96/34096, WO 98/24893, WO 00/76310 and related family members.

In an alternative approach, others have utilized a "minilocus" approach in which an exogenous Ig locus is mimicked through the inclusion of pieces (individual genes) from the Ig locus. Thus, one or more VH genes, one or more $D_H$ genes, one or more $J_H$ genes, a mu constant region, and a second constant region (preferably a gamma constant region) are formed into a construct for insertion into an animal. See e.g., U.S. Pat. Nos. 5,545,806; 5,545,807; 5,591,669; 5,612,205; 5,625,825; 5,625,126; 5,633,425; 5,643,763; 5,661,016; 5,721,367; 5,770,429; 5,789,215; 5,789,650; 5,814,318; 5,877; 397; 5,874,299; 6,023,010; and 6,255,458; and European Patent No. 0 546 073 B1; and International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and related family members.

Generation of human antibodies from mice in which, through microcell fusion, large pieces of chromosomes, or entire chromosomes, have been introduced, has also been demonstrated. See European Patent Application Nos. 773 288 and 843 961.

Human anti-mouse antibody (HAMA) responses have led the industry to prepare chimeric or otherwise humanized antibodies. While chimeric antibodies have a human constant region and an immune variable region, it is expected that certain human anti-chimeric antibody (HACA) responses will be observed, particularly in chronic or multi-dose utilizations of the antibody. Thus, it would be desirable to provide fully human antibodies against NaPi2b in order to vitiate or otherwise mitigate concerns and/or effects of HAMA or HACA response.

The production of antibodies with reduced immunogenicity is also accomplished via humanization, chimerization and display techniques using appropriate libraries. It will be appreciated that murine antibodies or antibodies from other species can be humanized or primatized using techniques well known in the art. See e.g., Winter and Harris Immunol Today 14:43 46 (1993) and Wright et al. Crit, Reviews in Immunol. 12125-168 (1992). The antibody of interest may be engineered by recombinant DNA techniques to substitute the CH1, CH2, CH3, hinge domains, and/or the framework domain with the corresponding human sequence (See WO 92102190 and U.S. Pat. Nos. 5,530,101; 5,585,089; 5,693, 761; 5,693,792; 5,714,350; and 5,777,085). Also, the use of Ig cDNA for construction of chimeric immunoglobulin genes is known in the art (Liu et al. P.N.A.S. 84:3439 (1987) and J. Immunol. 139:3521 (1987)). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of immunological Interest, N.I.H. publication no. 91-3242. Human C region genes are readily available from known clones. The choice of isotype will be guided by the desired effecter functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Further, human antibodies or antibodies from other species can be generated through display type technologies, including, without limitation, phage display, retroviral display, ribosomal display, and other techniques, using techniques well known in the art and the resulting molecules can be subjected to additional maturation, such as affinity maturation, as such techniques are well known in the art. Wright et al. Crit, Reviews in Immunol. 12125-168 (1992), Hanes and Plückthun PNAS USA 94:4937-4942 (1997) (ribosomal display), Parmley and Smith Gene 73:305-318 (1988) (phage display), Scott, TIBS, vol. 17:241-245 (1992), Cwirla et al. PNAS USA 87:6378-6382 (1990), Russel et al. Nucl. Acids Research 21:1081-1085 (1993), Hoganboom et al. Immunol. Reviews 130:43-68 (1992), Chiswell and McCafferty TIBTECH; 10:80-8A (1992), and U.S. Pat. No. 5,733,743. If display technologies are utilized to produce antibodies that are not human, such antibodies can be humanized as described above.

Using these techniques, antibodies can be generated to NaPi2b expressing cells, soluble forms of NaPi2b, epitopes or peptides thereof, and expression libraries thereto (See e.g., U.S. Pat. No. 5,703,057) which can thereafter be screened as described above for the activities described herein.

The NaPi2b antibodies disclosed herein can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g., a ligand to a cellular surface receptor), and a nucleic acid binding moiety (e.g., polylysine), viral vector (e.g., a DNA or RNA viral vector), fusion proteins such as described in PCT/US 95/02140 (WO 95/22618) which is a fusion protein containing a target moiety (e.g., an antibody specific for a target cell) and a nucleic acid binding moiety (e.g., a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g., infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g., adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of NaPi2b in a sample. The antibody can also be used to try to bind to and disrupt NaPi2b-related signaling.

NaPi2b-Targeted Antibody Conjugates:

The disclosure also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the trichothecenes.

A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolylene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies disclosed herein. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present disclosure, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat.#21651G); (iv) Sulfo-LC-SPDP (sulfosuccinimidyl 6 [3-(2-pyridyldithio)-propianamide] hexanoate (Pierce Chem. Co. Cat.#2165-G); and (v) sulfo-NHS (N-hydroxysulfo-succinimide: Pierce Chem. Co., Cat.#24510) conjugated to EDC.

The linkers described above contain components that have different attributes, thus leading to conjugates with differing physico-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

In one aspect, the conjugate described herein includes an isolated NaPi2b-targeted antibody that specifically binds to the extracellular region of SLC34A2 connected directly or indirectly to one or more D-carrying polymeric scaffolds independently comprising poly(1-hydroxymethylethylene hydroxymethyl-formal) (PHF) having a molecular weight ranging from about 2 kDa to about 40 kDa, wherein each of the one or more D-carrying polymeric scaffolds independently is of Formula (Ic):

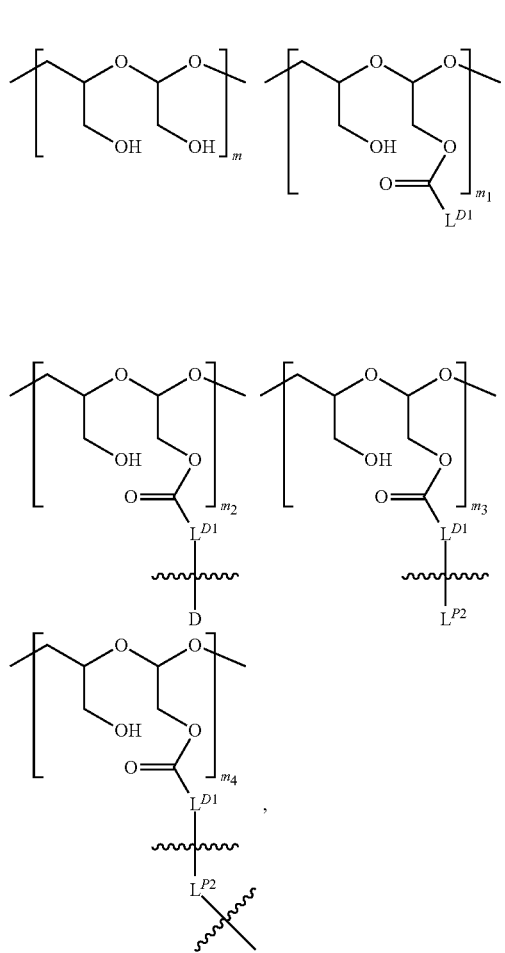

wherein:
each occurrence of D, independently, is a therapeutic or diagnostic agent; $L^{D1}$ is a carbonyl-containing moiety;
each occurrence of

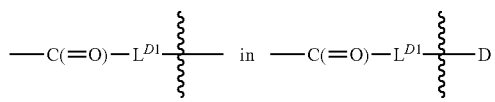

is independently a first linker that contains a biodegradable bond so that when the bond is broken, D is released in an active form for its intended therapeutic effect; and the

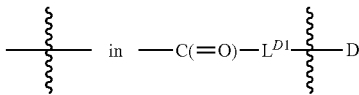

between $L^{D1}$ and D denotes direct or indirect attachment of D to $L^{D1}$;
each occurrence of

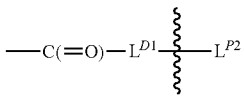

is independently a second linker not yet connected to the isolated NaPi2b antibody, in which $L^{P2}$ is a moiety containing a functional group that is yet to form a covalent bond with a functional group of the isolated antibody, and the

between $L^{D1}$ and $L^{P2}$ denotes direct or indirect attachment of $L^{P2}$ to $L^{D1}$, and each occurrence of the second linker is distinct from each occurrence of the first linker;
each occurrence of

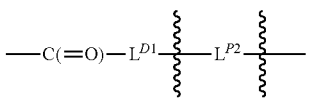

is independently a third linker that connects each D-carrying polymeric scaffold to the isolated antibody, in which the terminal

attached to $L^{P2}$ denotes direct or indirect attachment of $L^{P2}$ to the isolated antibody upon formation of a covalent bond between a functional group of $L^{P2}$ and a functional group of the isolated antibody; and each occurrence of the third linker is distinct from each occurrence of the first linker; m is an integer from 1 to about 300,
$m_1$ is an integer from 1 to about 140,
$m_2$ is an integer from 1 to about 40,
$m_3$ is an integer from 0 to about 18,
$m_4$ is an integer from 1 to about 10;
the sum of m, $m_1$, $m_2$, $m_3$, to and $m_4$ ranges from about 15 to about 300; and the total number of $L^{P2}$ attached to the isolated antibody is 10 or less.

The conjugate may include one or more of the following features.

For example, in Formula (Ic), $m_1$ is an integer from 1 to about 120 (e.g., about 1-90) and/or $m_3$ is an integer from 1 to about 10 (e.g., about 1-8).

For example, when the PHF in Formula (Ic) has a molecular weight ranging from about 6 kDa to about 20 kDa (i.e., the sum of m, $m_1$, $m_2$, $m_3$, and $m_4$ ranging from about 45 to about 150), $m_2$ is an integer from 2 to about 20, $m_3$ is an integer from 0 to about 9, $m_4$ is an integer from 1 to about 10, and/or $m_1$ is an integer from 1 to about 75 (e.g., $m_1$ being about 4-45).

For example, when the PHF in Formula (Ic) has a molecular weight ranging from about 8 kDa to about 15 kDa (i.e., the sum of m, $m_1$, $m_2$, $m_3$, and $m_4$ ranging from about 60 to about 110), $m_2$ is an integer from 2 to about 15, $m_3$ is an integer from 0 to about 7, $m_4$ is an integer from 1 to about 10, and/or $m_1$ is an integer from 1 to about 55 (e.g., $m_1$ being about 4-30).

For example, when the PHF in Formula (Ic) has a molecular weight ranging from about 2 kDa to about 20 kDa (i.e., the sum of m, $m_1$, $m_2$, $m_3$, and $m_4$ ranging from 15 to about 150), $m_2$ is an integer from 1 to about 20, $m_3$ is an integer from 0 to about 10 (e.g., $m_3$ ranging from 0 to about 9), $m_4$ is an integer from 1 to about 8, and/or $m_1$ is an integer from 1 to about 70, and the total number of $L^{P2}$ connected to the isolated antibody ranges from about 2 to about 8 (e.g., about 2, 3, 4, 5, 6, 7, or 8).

For example, when the PHF in Formula (Ic) has a molecular weight ranging from about 3 kDa to about 15 kDa (i.e., the sum of m, $m_1$, $m_2$, $m_3$, and $m_4$ ranging from 20 to about 110), $m_2$ is an integer from 2 to about 15, $m_3$ is an integer from 0 to about 8 (e.g., $m_3$ ranging from 0 to about 7), $m_4$ is an integer from 1 to about 8, and/or $m_1$ is an integer from 2 to about 50, and the total number of $L^{P2}$ connected to the isolated antibody ranges from about 2 to about 8 (e.g., about 2, 3, 4, 5, 6, 7, or 8).

For example, when the PHF in Formula (Ic) has a molecular weight ranging from about 5 kDa to about 10 kDa, (i.e., the sum of m, $m_1$, $m_2$, $m_3$ and $m_4$ ranges from about 40 to about 75), $m_2$ is an integer from about 2 to about 10 (e.g., $m_2$ being about 3-10), $m_3$ is an integer from 0 to about 5 (e.g., $m_3$ ranging from 0 to about 4), $m_4$ is an integer from 1 to about 8 (e.g., $m_4$ ranging from 1 to about 5), and/or $m_1$ is an integer from about 2 to about 35 (e.g., $m_1$ being about 5-35), and the total number of $L^{P2}$ connected to the isolated antibody ranges from about 2 to about 8 (e.g., about 2, 3, 4, 5, 6, 7, or 8).

For example, when the PHF has a molecular weight ranging from 2 kDa to 40 kDa, (e.g., about 6-20 kDa or about 8-15 kDa, about 2-20 kDa, or about 3-15 kDa, or about 5-10 kDa), the number of drugs per PHF (e.g., $m_2$) is an integer from 1 to about 40 (e.g., about 1-20, or about 2-15 or about 3-10 or about 2-10). This scaffold can be used, for example, for conjugating the isolated antibody having a molecular weight of 40 kDa or greater (e.g., 60 kDa or greater; 80 kDa or greater; 100 kDa or greater; 120 kDa or greater; 140 kDa or greater; 160 kDa or greater, 180 kDa or greater, or 200 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, 100-140 kDa or 140-150 kDa). In this embodiment, the ratio of the isolated antibody to PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:4, between about 1:2 and about 1:3, between about 1:3 and about 1:4, or between about 1:3 and about 1:5.

For example, when the PHF has a molecular weight ranging from 2 kDa to 40 kDa, (e.g., about 6-20 kDa or about 8-15 kDa, about 2-20 kDa, or about 3-15 kDa, or about 5-10 kDa), the number of drugs per PHF (e.g., $m_2$) is an integer from 1 to about 40 (e.g., about 1-20, or about 2-15 or about 3-10 or about 2-10). This scaffold can be used, for example, for conjugating the isolated antibody having a molecular weight of 140 kDa to 180 kDa or of 140 kDa to 150 kDa. In this embodiment, the ratio of the isolated antibody to PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:4, between about 1:2 and about 1:3, between about 1:3 and about 1:4, or between about 1:3 and about 1:5.

The NaPi-2b antibody in this molecular weight range, include but are not limited to, for example, full length antibodies, such as, IgG, IgM.

For example, when the PHF has a molecular weight ranging from 2 kDa to 40 kDa, the number of drugs per PHF (e.g., $m_2$) is an integer from 1 to about 40 (e.g., about 1-20 or about 2-15 or about 3-10 or about 2-10). This scaffold can be used, for example, for conjugating the isolated antibody having a molecular weight of 60 kDa to 120 kDa. In this embodiment, the ratio of the isolated antibody to PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:4, between about 1:2 and about 1:3, between about 1:3 and about 1:4, or between about 1:3 and about 1:5.

In certain embodiment, D is a therapeutic agent. In certain embodiments, the therapeutic agent is a small molecule having a molecular weight ≤ about 5 kDa, ≤ about 4 kDa, ≤ about 3 kDa, ≤ about 1.5 kDa, or ≤ about 1 kDa.

In certain embodiments, the therapeutic agent has an $IC_{50}$ of about less than 1 nM.

In another embodiment, the therapeutic agent has an $IC_{50}$ of about greater than 1 nM, for example, the therapeutic agent has an $IC_{50}$ of about 1 to 50 nM.

Some therapeutic agents having an $IC_{50}$ of greater than about 1 nM (e.g., "less potent drugs") are unsuitable for conjugation with an antibody using art-recognized conjugation techniques. Without wishing to be bound by theory, such therapeutic agents have a potency that is insufficient for use in targeted antibody-drug conjugates using conventional techniques as sufficient copies of the drug (i.e., more than 8) cannot be conjugated using art-recognized techniques without resulting in diminished pharmacokinetic and physiochemical properties of the conjugate. However sufficiently high loadings of these less potent drugs can be achieved using the conjugation strategies described herein thereby resulting in high loadings of the therapeutic agent while maintaining the desirable pharmacokinetic and physiochemical properties. Thus, the disclosure also relates to an antibody-polymer-drug conjugate that includes the isolated antibody, PHF and at least eight therapeutic agent moieties, where D is auristatin, dolastatin (e.g., dolastatin 10 or dolastatin 15), monomethylauristatin E (MMAE), monomethylauristatin F (MMAF), auristatin F, AF HPA, monomethyl AF HPA, phenylenediamine (AFP).

For example, the duocarmycin or analogs thereof is duocarmycin A, duocarmycin B1, duocarmycin B2, duocarmycin C1, duocarmycin C2, duocarmycin D, duocarmycin SA, CC-1065, adozelesin, bizelesin, or carzelesin.

Other examples of D include those described in, for example, U.S. Pat. No. 8,815,226; and US Application Publication No. 2015-0104407; the contents of each of which are incorporated herein in their entireties.

In some embodiments, the number of D-carrying polymeric scaffolds that can be conjugated to an antibody is limited by the number of free cysteine residues. In some embodiments, free cysteine residues are introduced into the antibody amino acid sequence by the methods described herein. Exemplary conjugates disclosed herein can include antibodies that have 1, 2, 3, or 4 engineered cysteine amino acids (Lyon, R. et al (2012) Methods in Enzym. 502:123-138). In some embodiments, one or more free cysteine residues are already present in an antibody, without the use of engineering, in which case the existing free cysteine residues may be used to conjugate the antibody to a D-carrying polymeric scaffold. In some embodiments, an antibody is exposed to reducing conditions prior to conjugation of the antibody in order to generate one or more free cysteine residues.

In certain embodiments, the functional group of $L^{P2}$ that is yet to form a covalent bond with a functional group of the isolated antibody (such as a functional group or a reactive moiety on an amino acid residue of the antibody, for example, a functional group on a cysteine residue or a lysine residue of the antibody), is selected from —$SR^P$, —S—S-LG,

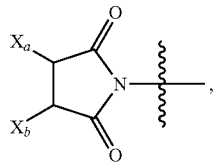

and halo, in which LG is a leaving group, $R^P$ is H or a sulfur protecting group, and one of $X_a$ and $X_b$ is H and the other is a water-soluble maleimido blocking moiety, or $X_a$ and $X_b$, together with the carbon atoms to which they are attached for a carbon-carbon double bond. For example, the functional group of $L^{P2}$ that is yet to form a covalent bond is a functional group that is not reacted with a functional group of the isolated antibody, e.g.,

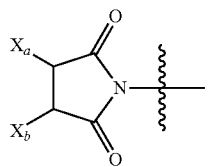

as the functional group of $L^{P2}$, in which one of $X_a$ and $X_b$ is H and the other is a water-soluble maleimido blocking moiety, or $X_a$ and $X_b$.

In certain embodiments, in the conjugate described herein, the D-carrying polymeric scaffold of Formula (Ic) is of Formula (Ie):

(Ie)

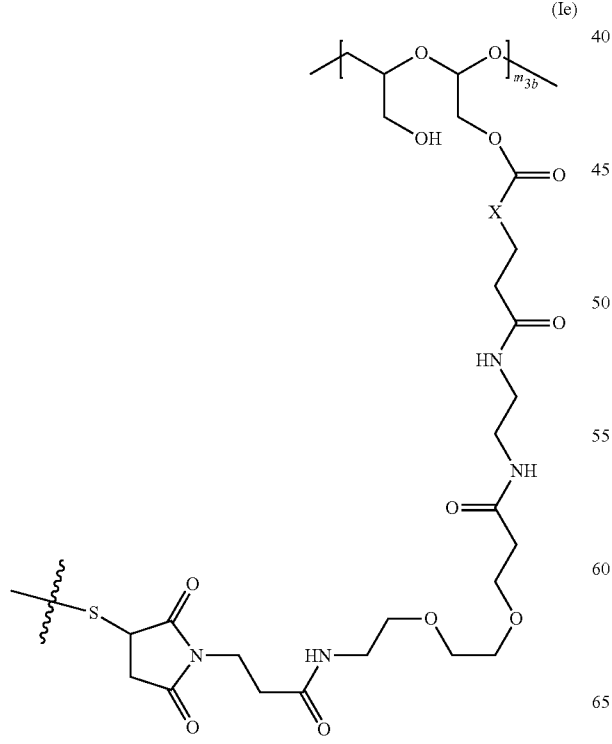

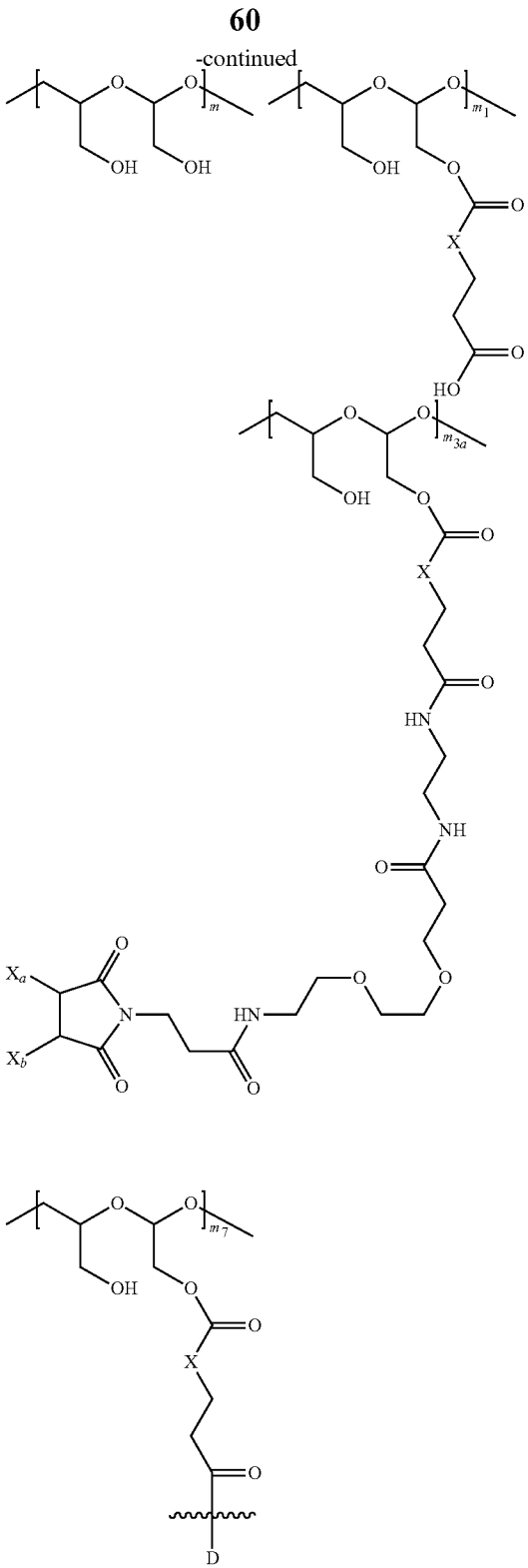

wherein,
the PHF has a molecular weight ranging from about 2 kDa to about 40 kDa;
each occurrence of D independently is a therapeutic agent having a molecular weight of ≤5 kDa, and the

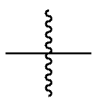

between D and the carbonyl group denotes direct or indirect attachment of D to the carbonyl group, X is $CH_2$, O, or NH;

one of $X_a$ and $X_b$ is H and the other is a water-soluble maleimido blocking moiety, or $X_a$ and $X_b$, together with the carbon atoms to which they are attached for a carbon-carbon double bond, $m_1$ is an integer from 1 to about 140, $m_7$ is an integer from 1 to about 40, and the sum of $m_1$ and $m_7$ is about 2 to about 180 m is an integer from 1 to about 300, $m_{3a}$ is an integer from 0 to about 17, $m_{3b}$ is an integer from 1 to about 8, and the sum of $m_{3a}$ and $m_{3b}$ is between 1 and 18, and the sum of m, $m_1$, $m_7$, $m_{3a}$, and $m_{3b}$ ranges from about 15 to about 300.

In certain embodiments, in the conjugate described herein, the D-carrying polymeric scaffold of Formula (Ie) is of Formula (Id):

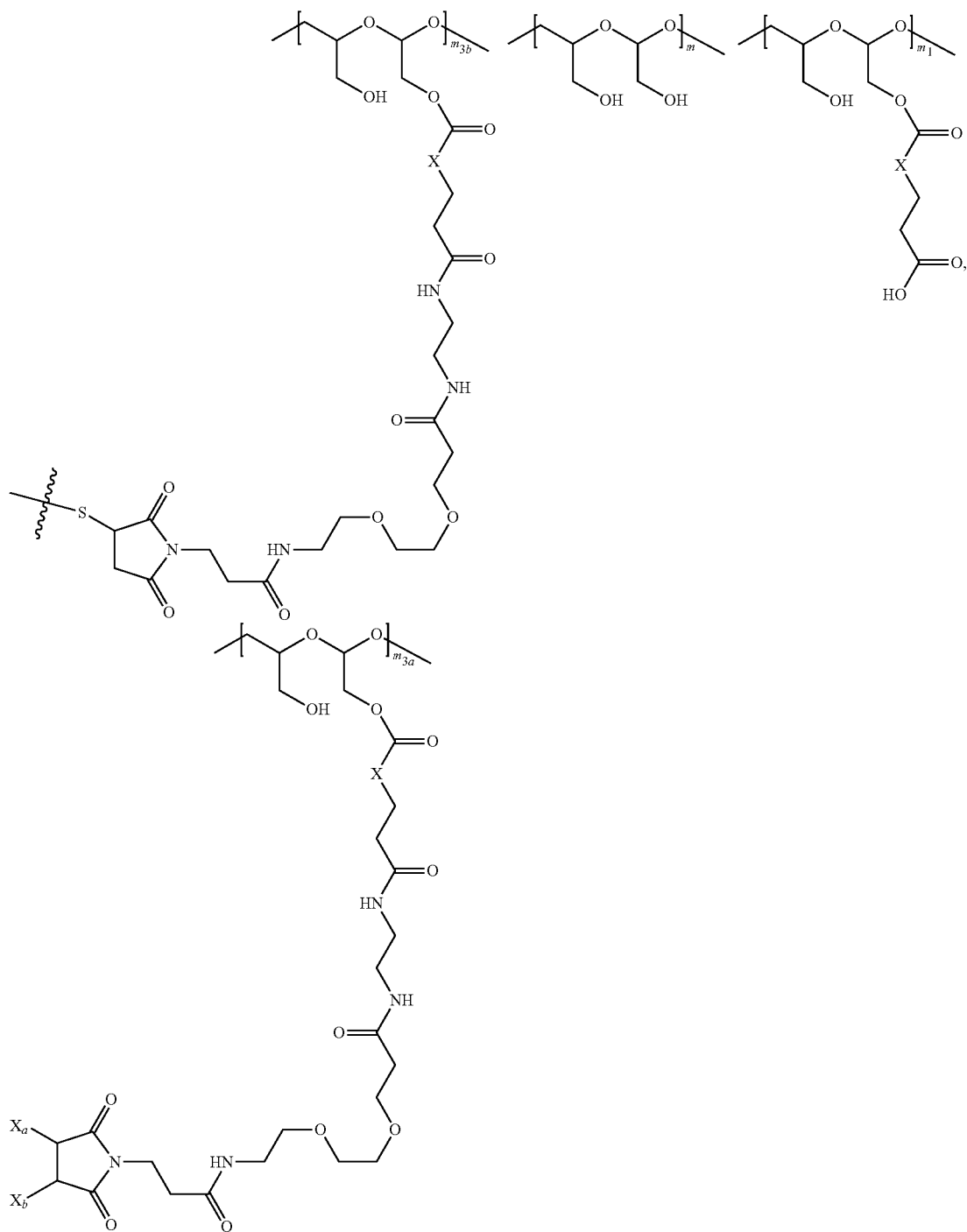

(Id)

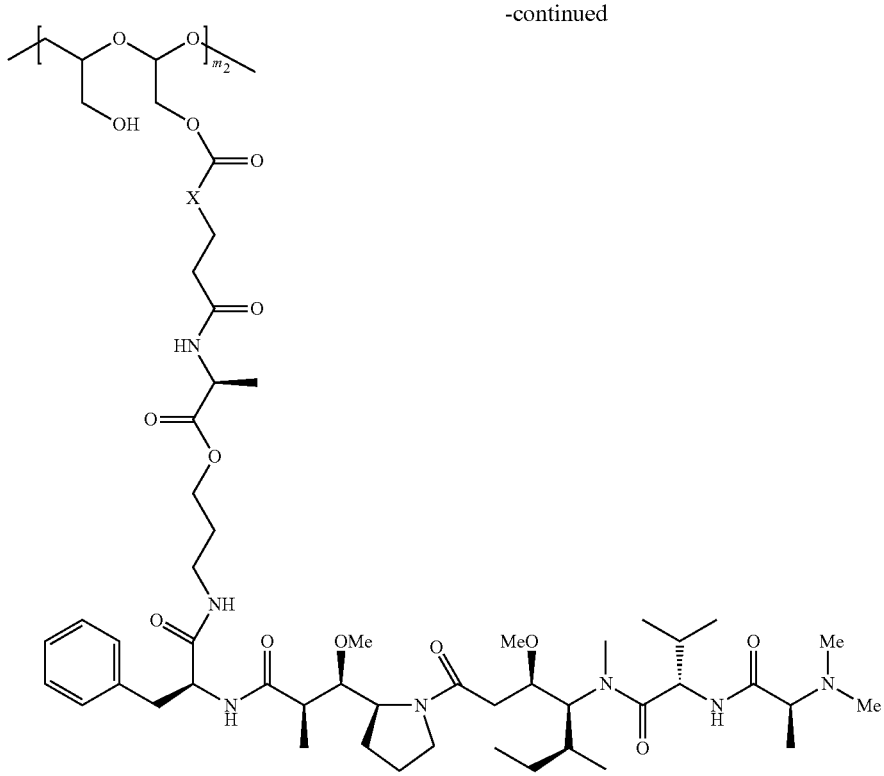

wherein:

one of $X_a$ and $X_b$ is H and the other is a water-soluble maleimido blocking moiety, or $X_a$ and $X_b$, together with the carbon atoms to which they are attached for a carbon-carbon double bond;

$m_{3a}$ is an integer from 0 to about 17, $m_{3b}$ is an integer from 1 to about 8, and the sum of $m_{3a}$ and $m_{3b}$ is between 1 and 18, and the sum of m, $m_1$, $m_2$, $m_{3a}$, and $m_{3b}$ ranges from about 15 to about 300.

For example, the ratio between $m_2$ and $m_{3b}$ is greater than 1:1 and less than or equal to 10:1.

For example, the ratio between $m_2$ and $m_{3b}$ is about 9:1, 8:1, 7:1, 6:1, 5:1, 4:1, 3:1, or 2:1.

For example, the ratio between $m_2$ and $m_{3b}$ is between 2:1 and 8:1.

For example, the ratio between $m_2$ and $m_{3b}$ is about 8:1, 71, 7:1, 6:1, 5:1, 4:1, 3:1, or 2:1.

For example, the ratio between $m_2$ and $m_{3b}$ is between 2:1 and 4:1.

For example, the ratio between $m_2$ and $m_{3b}$ is about 4:1, 3:1, or 2:1.

For example, the ratio between $m_2$ and $m_{3b}$ is about 3:1 and 5:1.

For example, the ratio between $m_2$ and $m_{3b}$ is about 3:1, 4:1 or 5:1.

For example, when the PHF in Formula (Id) has a molecular weight ranging from about 2 kDa to about 20 kDa, the sum of m, $m_1$, $m_2$, $m_{3a}$ and $m_{3b}$ ranges from about 15 to about 150, $m_1$ is an integer from 1 to about 70, $m_2$ is an integer from 1 to about 20, $m_{3a}$ is an integer from 0 to about 9, $m_{3b}$ is an integer from 1 to about 8 and the ratio between the PHF and the isolated NaPi2b-targeted antibody is an integer from 2 to about 8.

For example, when the PHF in Formula (Id) has a molecular weight ranging from about 3 kDa to about 15 kDa, the sum of m, $m_1$, $m_2$, $m_{3a}$ and $m_{3b}$ ranges from about 20 to about 110, $m_1$ is an integer from 2 to about 50, $m_2$ is an integer from 2 to about 15, $m_{3a}$ is an integer from 0 to about 7, $m_{3b}$ is an integer from 1 to about 8 and the ratio between the PHF and the isolated NaPi2b-targeted antibody is an integer from 2 to about 8 (e.g., an integer from 2 to about 6 or an integer from 2 to about 4).

For example, when the PHF in Formula (Id) has a molecular weight ranging from about 5 kDa to about 10 kDa, the sum of m, $m_1$, $m_2$, $m_{3a}$ and $m_{3b}$ ranges from about 40 to about 75, $m_1$ is an integer from about 2 to about 35, $m_2$ is an integer from about 2 to about 10, $m_{3a}$ is an integer from 0 to about 4, $m_{3b}$ is an integer from 1 to about 5 and the ratio between the PHF and the isolated NaPi2b-targeted antibody is an integer from 2 to about 8 (e.g., an integer from 2 to about 6 or an integer from 2 to about 4).

For example, the water-soluble maleimido blocking moieties are moieties that can be covalently attached to one of the two olefin carbon atoms upon reaction of the maleimido group with a thiol-containing compound of Formula (II):

$$R_{90}—(CH_2)_d—SH \quad (II)$$

wherein:

$R_{90}$ is $NHR_{91}$, OH, $COOR_{93}$, $CH(NHR_{91})COOR_{93}$ or a substituted phenyl group;

$R_{93}$ is hydrogen or $C_{1-4}$ alkyl;

$R_{91}$ is hydrogen, $CH_3$ or $CH_3CO$ and d is an integer from 1 to 3.

For example, the water-soluble maleimido blocking compound of Formula (II) can be cysteine, N-acetyl cysteine, cysteine methyl ester, N-methyl cysteine, 2-mercaptoethanol, 3-mercaptopropanoic acid, 2-mercaptoacetic acid, mercaptomethanol (i.e., $HOCH_2SH$), benzyl thiol in which phenyl is substituted with one or more hydrophilic substituents, or 3-aminopropane-1-thiol. The one or more hydrophilic substituents on phenyl comprise OH, SH, methoxy, ethoxy, COOH, CHO, $COC_{1-4}$ alkyl, $NH_2$, F, cyano, $SO_3H$, $PO_3H$, and the like.

For example, the water-soluble maleimido blocking group is $—S—(CH_2)_d—R_{90}$, in which, $R_{90}$ is OH, COOH, or $CH(NHR_{91})COOR_{93}$;

$R_{93}$ is hydrogen or $CH_3$;

$R_{91}$ is hydrogen or $CH_3CO$; and d is 1 or 2.

For example, the water-soluble maleimido blocking group is $—S—CH_2—CH(NH_2)COOH$.

For example, when the PHF has a molecular weight ranging from 2 kDa to 40 kDa, (e.g., about 2-20 kDa, or about 3-15 kDa, or about 5-10 kDa), the number of drugs per PHF (e.g., $m_2$) is an integer from 1 to about 40 (e.g., about 1-20 or about 2-15 or about 3-10 or about 2-10). This scaffold can be used, for example, for conjugating an isolated antibody having a molecular weight of 40 kDa or greater (e.g., 60 kDa or greater; 80 kDa or greater; or 100 kDa or greater; 120 kDa or greater; 140 kDa or greater; 160 kDa or greater, 180 kDa or greater, or 200 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, 100-140 kDa or 140-150 kDa). In this embodiment, the ratio of the isolated antibody to PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:8, between about 1:2 and about 1:6, between about 1:2 and about 1:5, between about 1:2 and about 1:4, between about 1:2 and about 1:3, between about 1:3 and about 1:4, or between about 1:3 and about 1:5.

For example, when the PHF has a molecular weight ranging from 2 kDa to 40 kDa, (e.g., about 2-20 kDa, or about 3-15 kDa, or about 5-10 kDa), the number of drugs per PHF (e.g., $m_2$) is an integer from 1 to about 40 (e.g., about 1-20 or about 2-15 or about 3-10 or about 2-10). This scaffold can be used, for example, for conjugating an isolated antibody having a molecular weight of 140 kDa to 180 kDa or of 140 kDa to 150 kDa. In this embodiment the ratio of the isolated antibody to PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:8, between about 1:2 and about 1:6, between about 1:2 and about 1:5, between about 1:2 and about 1:4, between about 1:2 and about 1:3, between about 1:3 and about 1:4, or between about 1:3 and about 1:5.

The isolated antibodies in this molecular weight range, include but are not limited to, for example, full length antibodies, such as, IgG, IgM.

For example, when the PHF has a molecular weight ranging from 2 kDa to 40 kDa (e.g., about 2-20 kDa, or about 3-15 kDa, or about 5-10 kDa), the number of drugs per PHF (e.g., $m_2$) is an integer from 1 to about 40, (e.g., about 1-20 or about 2-15 or about 3-10 or 2-10). This scaffold can be used, for example, for conjugating an isolated antibody having a molecular weight of 60 kDa to 120 kDa. In this embodiment the ratio of the isolated antibody to PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:8, between about 1:2 and about 1:6, between about 1:2 and about 1:5, between about 1:2 and about 1:4, between about 1:2 and about 1:3, between about 1:3 and about 1:4, or between about 1:3 and about 1:5.

For example, when the PHF has a molecular weight ranging from 2 kDa to 40 kDa, (e.g., about 2-20 kDa, or about 3-15 kDa, or about 5-10 kDa), the number of drugs per PHF (e.g., $m_2$) is an integer from 1 to about 40 (e.g., about 1-20 or about 2-15 or about 3-10 or 2-10). This scaffold can be used, for example, for conjugating the isolated antibody having a molecular weight of 40 kDa to 80 kDa. In this embodiment the ratio of the isolated antibody to PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:8, between about 1:2 and about 1:6, between about 1:2 and about 1:5, between about 1:2 and about 1:4, between about 1:2 and about 1:3, between about 1:3 and about 1:4, or between about 1:3 and about 1:5.

In certain embodiments, in the conjugate described herein, the D-carrying polymeric scaffold of Formula (Ie) is of Formula (If), wherein the polymer is PHF that has a molecular weight ranging from about 2 kDa to about 40 kDa:

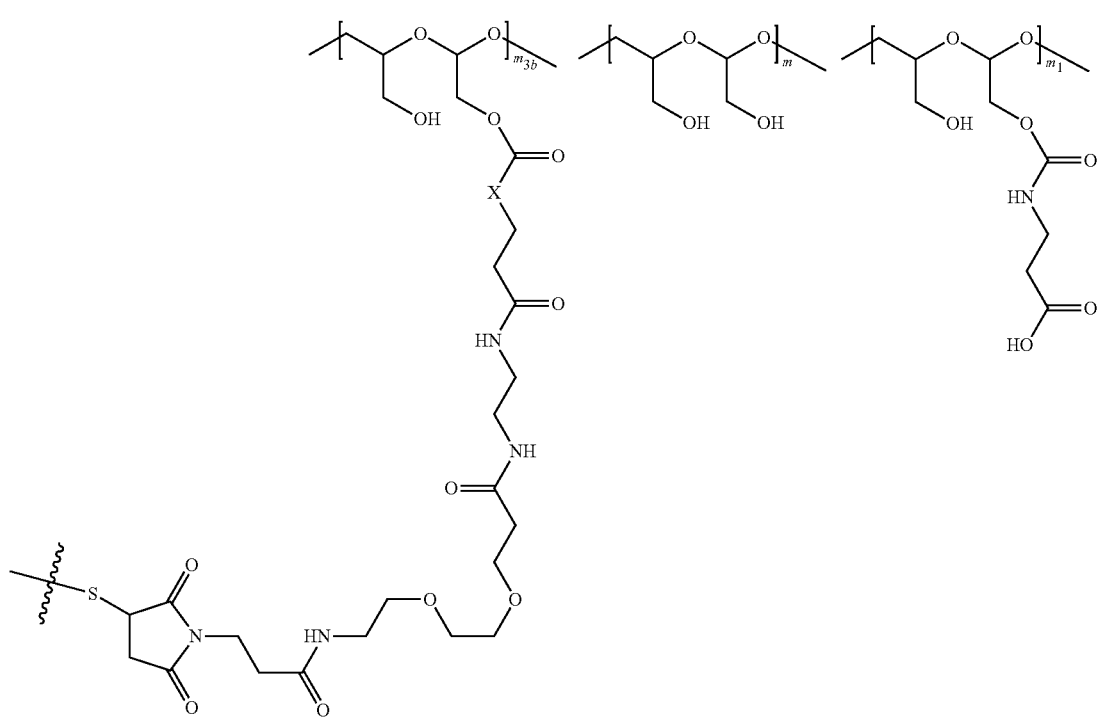
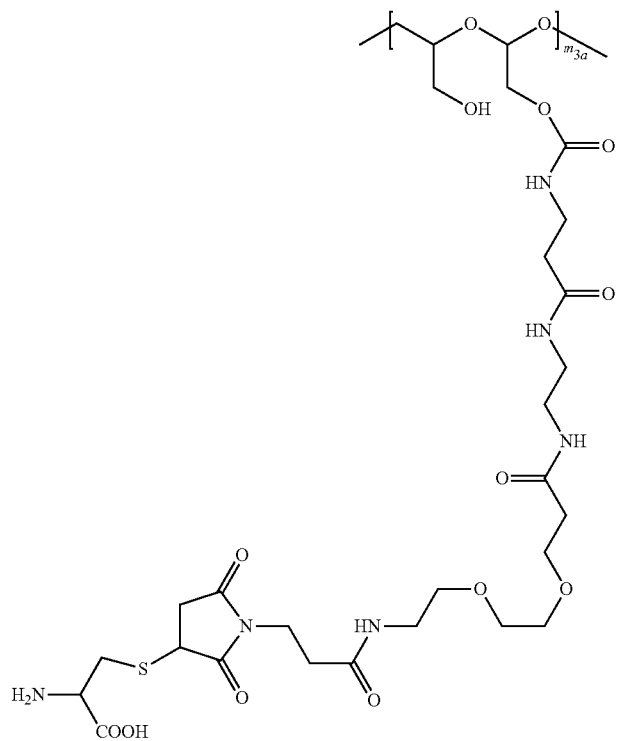

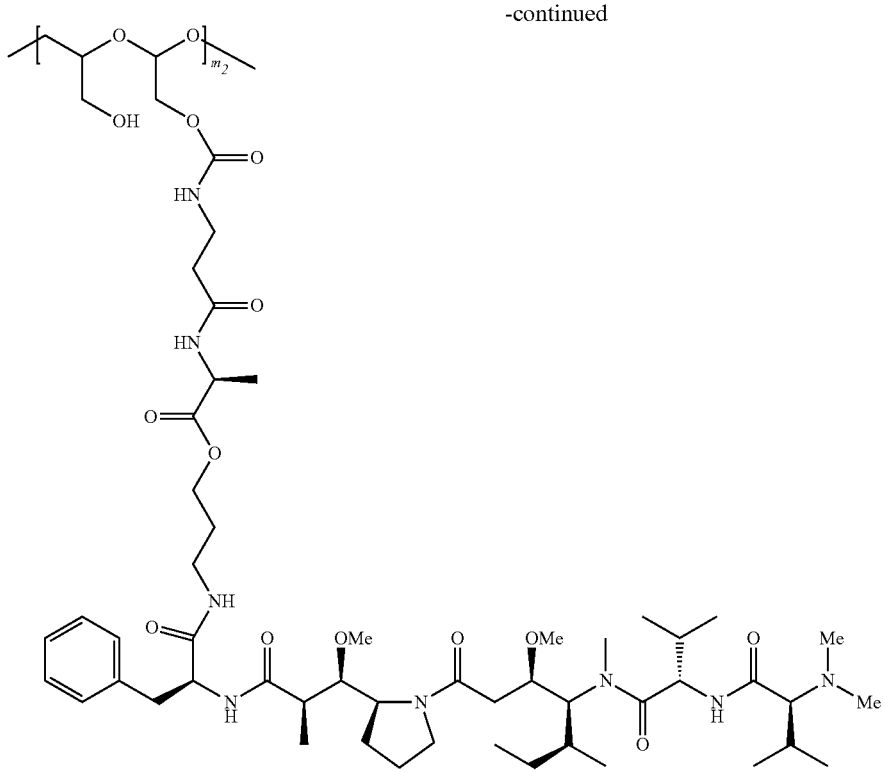

wherein:
m is an integer from 1 to about 300,
$m_1$ is an integer from 1 to about 140,
$m_2$ is an integer from 1 to about 40,
$m_{3a}$ is an integer from 0 to about 17,
$m_{3b}$ is an integer from 1 to about 8;
the sum of $m_{3a}$ and $m_{3b}$ ranges from 1 and about 18;
the sum of m, $m_1$, $m_2$, $m_{3a}$, and $m_{3b}$ ranges from about 15 to about 300;
the terminal

denotes the attachment of one or more polymeric scaffolds to the isolated antibody that specifically binds to the extracellular region of SLC34A2 (i) a variable heavy chain complementarity determining region 1 (CDRH1) comprising the amino acid sequence GYTFTGYNIH (SEQ ID NO: 5); a variable heavy chain complementarity determining region 2 (CDRH2) comprising the amino acid sequence AIYPGNGDTSYKQKFRG (SEQ ID NO: 6); a variable heavy chain complementarity determining region 3 (CDRH3) comprising the amino acid sequence GET-ARATFAY (SEQ ID NO: 7); a variable light chain complementarity determining region 1 (CDRL1) comprising the amino acid sequence SASQDIGNFLN (SEQ ID NO: 8); a variable light chain complementarity determining region 2 (CDRL2) comprising the amino acid sequence YTSSLYS (SEQ ID NO: 9); and a variable light chain complementarity determining region 3 (CDRL3) comprising the amino acid sequence QQYSKLPLT (SEQ ID NO: 10) or (ii) a CDRH1 comprising the amino acid sequence GFSFSDFAMS (SEQ ID NO: 18); a CDRH2 comprising the amino acid sequence ATIGRVAFHTYYPDSMKG (SEQ ID NO: 19); a CDRH3 comprising the amino acid sequence ARHRGFDVGHFDF (SEQ ID NO: 20); a CDRL1 comprising the amino acid sequence RSSETLVHSSGNTYLE (SEQ ID NO: 21); a CDRL2 comprising the amino acid sequence RVSNRFS (SEQ ID NO: 22); and a CDRL3 comprising the amino acid sequence FQGSFNPLT (SEQ ID NO: 23); and
the ratio between the PHF and the antibody is 10 or less.

In some embodiments, the isolated NaPi2b-targeted antibody specifically binds to SLC34A2 and includes (i) a CDRH1 comprising the amino acid sequence GYTFTGY-NIH (SEQ ID NO: 5); a CDRH2 comprising the amino acid sequence AIYPGNGDTSYKQKFRG (SEQ ID NO: 6); a CDRH3 comprising the amino acid sequence GET-ARATFAY (SEQ ID NO: 7); a CDRL1 comprising the amino acid sequence SASQDIGNFLN (SEQ ID NO: 8); a CDRL2 comprising the amino acid sequence YTSSLYS (SEQ ID NO: 9); and a CDRL3 comprising the amino acid sequence QQYSKLPLT (SEQ ID NO: 10).

In some embodiments, the isolated NaPi2b-targeted antibody specifically binds to SLC34A2 and includes a CDRH1 comprising the amino acid sequence GFSFSDFAMS (SEQ ID NO: 18); a CDRH2 comprising the amino acid sequence ATIGRVAFHTYYPDSMKG (SEQ ID NO: 19); a CDRH3 comprising the amino acid sequence ARHRGFDVGHFDF (SEQ ID NO: 20); a CDRL1 comprising the amino acid sequence RSSETLVHSSGNTYLE (SEQ ID NO: 21); a CDRL2 comprising the amino acid sequence RVSNRFS (SEQ ID NO: 22); and a CDRL3 comprising the amino acid sequence FQGSFNPLT (SEQ ID NO: 23).

The scaffold of Formula (If) can include one or more of the following features:

When the PHF in Formula (If) has a molecular weight ranging from about 2 kDa to about 20 kDa, the sum of m, $m_1$, $m_2$, $m_{3a}$ and $m_{3b}$ ranges from about 15 to about 150, $m_1$ is an integer from 1 to about 70, $m_2$ is an integer from 1 to about 20, $m_{3a}$ is an integer from 0 to about 9, $m_{3b}$ is an integer from 1 to about 8, the sum of $m_{3a}$ and $m_{3b}$ ranges from 1 and about 10, and the ratio between the PHF and antibody is an integer from 2 to about 8.

When the PHF in Formula (If) has a molecular weight ranging from about 3 kDa to about 15 kDa, the sum of m, $m_1$, $m_2$, $m_{3a}$ and $m_{3b}$ ranges from about 20 to about 110, $m_1$ is an integer from 2 to about 50, $m_2$ is an integer from 2 to about 15, $m_{3a}$ is an integer from 0 to about 7, $m_{3b}$ is an integer from 1 to about 8, the sum of $m_{3a}$ and $m_{3b}$ ranges from 1 and about 8; and the ratio between the PHF and antibody is an integer from 2 to about 8 (e.g., from about 2 to about 6 or from about 2 to about 4).

When the PHF in Formula (If) has a molecular weight ranging from about 5 kDa to about 10 kDa, the sum of m, $m_1$, $m_2$, $m_{3a}$ and $m_{3b}$ ranges from about 40 to about 75, $m_1$ is an integer from about 2 to about 35, $m_2$ is an integer from about 2 to about 10, $m_{3a}$ is an integer from 0 to about 4, $m_{3b}$ is an integer from 1 to about 5, the sum of $m_{3a}$ and $m_{3b}$ ranges from 1 and about 5; and the ratio between the PHF and antibody is an integer from 2 to about 8 (e.g., from about 2 to about 6 or from about 2 to about 4).

In certain embodiments, the ratio between auristatin F hydroxypropyl amide ("AF HPA") and the antibody can be about 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In certain embodiments, the ratio between AF HPA and the antibody can be about 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In other embodiments, the ratio between AF HPA and the antibody can be about 20:1, 19:1, 18:1, 17:1, 16:1, 15:1, 14:1, 13:1, 12:1, 11:1, 10:1, 9:1, 8:1, 7:1 or 6:1.

In some embodiments, the ratio between AF HPA and the antibody can be about 16:1, 15:1, 14:1, 13:1, 12:1, 11:1 or 10:1.

In some embodiments, the ratio between AF and the antibody can be about 15:1, 14:1, 13:1, 12:1 or 11:1.

In some embodiments, the ratio between AF HPA and the antibody can be about 15:1, 14:1, 13:1 or 12:1.

In certain embodiments, the ratio between PHF and the antibody can be about 10:1, 9:1, 8:1, 7:1, 6:1, 5:1, 4:1, 3:1, 2:1 or 1:1.

In certain embodiments, the ratio between PHF and the antibody can be about 8:1, 7:1, 6:1, 5:1, 4:1, 3:1 or 2:1.

In other embodiments, the ratio between PHF and the antibody can be about 6:1, 5:1, 4:1, 3:1, 2:1 or 1:1.

In other embodiments, the ratio between PHF and the antibody can be about 6:1, 5:1, 4:1, 3:1 or 2:1.

In other embodiments, the ratio between PHF and the antibody can be about 6:1, 5:1, 4:1 or 3:1.

In some embodiments, the ratio between PHF and the antibody can be about 5:1, 4:1 or 3:1.

In some embodiments, the ratio between PHF and the antibody can be about 4:1, 3:1 or 2:1.

Other embodiments of antibody-polymer drug conjugates are those described in, for example, U.S. Pat. No. 8,815,226; and US Application Publication No. 2015-0104407; the contents of each of which are incorporated herein in their entireties.

This disclosure also relates to a drug derivative so modified that it can be directly conjugated to an antibody absent a polymeric carrier, and the drug-antibody conjugates thereof.

In some embodiments, the NaPi2b-targeted antibody drug conjugates include an antibody conjugated, i.e., covalently attached, to the drug moiety. In some embodiments, the antibody is covalently attached to the drug moiety through a linker, e.g., a non-polymeric linker.

The "D" (e.g., a drug moiety) of the NaPi2b-targeted antibody-drug conjugates (ADC) may include any compound, moiety or group that has a cytotoxic or cytostatic effect as defined herein. In certain embodiments, a NaPi2b-targeted-antibody-drug conjugate (ADC) comprises a NaPi2b-targeted antibody (Ab) which targets a tumor cell, D (e.g., a drug moiety), and a linker moiety (L) that attaches Ab to D. In some embodiments, the antibody is attached to the linker moiety (L) through one or more amino acid residues, such as lysine and/or cysteine.

In certain embodiments the ADC has Formula (Ig):

$$Ab\text{-}(L\text{-}D)_p \qquad (Ig),$$

where p is 1 to about 20.

In some embodiments, the number of drug moieties that can be conjugated to an antibody is limited by the number of free cysteine residues. In some embodiments, free cysteine residues are introduced into the antibody amino acid sequence by the methods described herein. Exemplary ADC of Formula Ig include, but are not limited to, antibodies that have 1, 2, 3, or 4 engineered cysteine amino acids (Lyon, R. et al (2012) Methods in Enzym. 502:123-138). In some embodiments, one or more free cysteine residues are already present in an antibody, without the use of engineering, in which case the existing free cysteine residues may be used to conjugate the antibody to a drug. In some embodiments, an antibody is exposed to reducing conditions prior to conjugation of the antibody in order to generate one or more free cysteine residues.

In some embodiments the "Linker" (L) is a bifunctional or multifunctional moiety that can be used to link one or more D (e.g., drug moieties) to an antibody (Ab) to form an antibody-drug conjugate (ADC) of Formula Ig. In some embodiments, antibody-drug conjugates (ADC) can be prepared using a Linker having reactive functionalities for covalently attaching to the drug and to the antibody. For example, in some embodiments, a cysteine thiol of an antibody (Ab) can form a bond with a reactive functional group of a linker or a drug-linker intermediate to make an ADC.

In one aspect, a linker has a functionality that is capable of reacting with a free cysteine present on an antibody to form a covalent bond. Nonlimiting exemplary such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), Bioconjugate Chemistry 15(4):765-773, and the Examples herein.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio) pentanoate ("SPP"), and 4-(N-maleimidomethyl)cyclohexane-1 carboxylate ("MCC"). Various linker components are known in the art, some of which are described below.

A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020).

In certain embodiments, a linker has the following Formula (IIg):

wherein:
A is a "stretcher unit", and a is an integer from 0 to 1;
W is an "amino acid unit", and w is an integer from 0 to 12;
Y is a "spacer unit", and y is an integer 0, 1, or 2. An ADC comprising the linker of Formula (IIg) has the Formula I(A): Ab-(Aa-Ww-Yy-D)p, wherein Ab, D, and p are defined as above for Formula (Ig). Exemplary embodiments of such linkers are described in U.S. Pat. No. 7,498,298, which is incorporated herein by reference in its entirety.

In some embodiments, a linker component comprises a "stretcher unit" (A) that links an antibody to another linker component or to a drug moiety. Nonlimiting exemplary stretcher units are shown below (wherein the wavy line indicates sites of covalent attachment to an antibody, drug, or additional linker components):

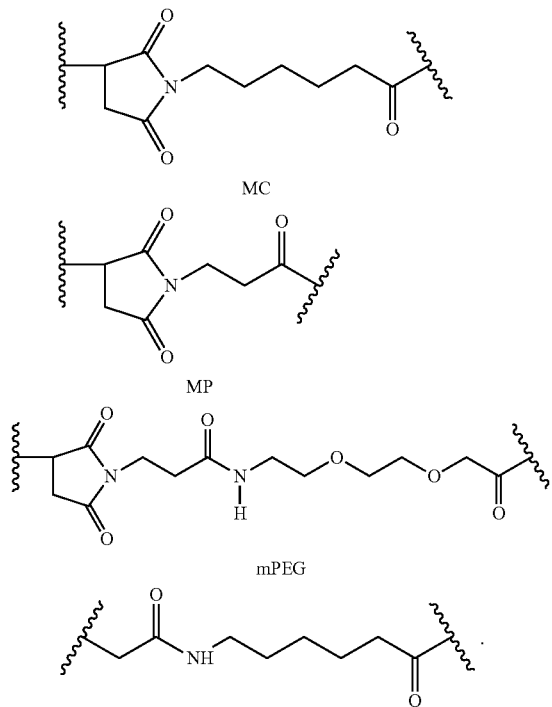

In some embodiments, a linker component comprises an "amino acid unit" (W). In some such embodiments, the amino acid unit allows for cleavage of the linker by a protease, thereby facilitating release of the drug from the immunoconjugate upon exposure to intracellular proteases, such as lysosomal enzymes (Doronina et al. (2003) Nat. Biotechnol. 21:778-784). Exemplary amino acid units include, but are not limited to, dipeptides, tripeptides, tetrapeptides, and pentapeptides. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly). An amino acid unit may comprise amino acid residues that occur naturally and/or minor amino acids and/or non-naturally occurring amino acid analogs, such as citrulline. Amino acid units can be designed and optimized for enzymatic cleavage by a particular enzyme, for example, a tumor-associated protease, cathepsin B, C and D, or a plasmin protease.

Typically, peptide-type linkers can be prepared by forming a peptide bond between two or more amino acids and/or peptide fragments. Such peptide bonds can be prepared, for example, according to a liquid phase synthesis method (e.g., E. Schrider and K. Lubke (1965) "The Peptides", volume 1, pp 76-136, Academic Press).

In some embodiments, a linker component comprises a "spacer" unit that links the antibody to a drug moiety, either directly or through a stretcher unit and/or an amino acid unit. A spacer unit may be "self-immolative" or a "non-self-immolative." A "non-self-immolative" spacer unit is one in which part or all of the spacer unit remains bound to the drug moiety upon cleavage of the ADC. Examples of non-self-immolative spacer units include, but are not limited to, a glycine spacer unit and a glycine-glycine spacer unit. In some embodiments, enzymatic cleavage of an ADC containing a glycine-glycine spacer unit by a tumor-cell associated protease results in release of a glycine-glycine-drug moiety from the remainder of the ADC. In some such embodiments, the glycine-glycine-drug moiety is subjected to a hydrolysis step in the tumor cell, thus cleaving the glycine-glycine spacer unit from the drug moiety.

A "self-immolative" spacer unit allows for release of the drug moiety. In certain embodiments, a spacer unit of a linker comprises a p-aminobenzyl unit. In some such embodiments, a p-aminobenzyl alcohol is attached to an amino acid unit via an amide bond, and a carbamate, methylcarbamate, or carbonate is made between the benzyl alcohol and the drug (Hamann et al. (2005) Expert Opin. Ther. Patents (2005) 15:1087-1103). In some embodiments, the spacer unit comprises p-aminobenzyloxycarbonyl (PAB). In some embodiments, an ADC comprising a self-immolative linker has the structure:

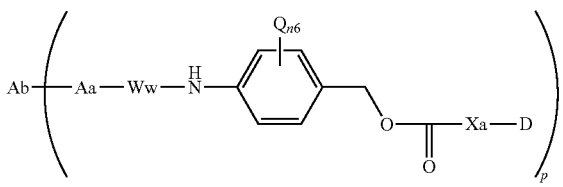

wherein:
Q is —$C_1$-$C_8$ alkyl, —O—($C_1$-$C_8$ alkyl), halogen, nitro, or cyano;
$n_6$ is an integer from 0 to 4;
$X_a$ may be one or more additional spacer units or may be absent; and
p in an integer from 1 to about 20.

In some embodiments, p in an integer from 1 to 10, 1 to 7, 1 to 5, or 1 to 4. Nonlimiting exemplary $X_a$ spacer units include:

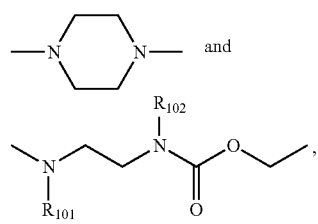

wherein $R_{101}$ and $R_{102}$ are independently selected from H and $C_1$-$C_6$ alkyl. In some embodiments, $R_{101}$ and $R_{102}$ are each —$CH_3$.

Other examples of self-immolative spacers include, but are not limited to, aromatic compounds that are electronically similar to the PAB group, such as 2-aminoimidazol-5-methanol derivatives (U.S. Pat. No. 7,375,078; Hay et al. (1999) Bioorg. Med. Chem. Lett. 9:2237) and ortho- or para-aminobenzylacetals. In some embodiments, spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Linkage of a drug to the α-carbon of a glycine residue is another example of a self-immolative spacer that may be useful in ADC (Kingsbury et al (1984) J. Med. Chem. 27:1447).

In some embodiments, linker L may be a dendritic type linker for covalent attachment of more than one drug moiety to an antibody through a branching, multifunctional linker moiety (Sun et al (2002) Bioorganic & Medicinal Chemistry Letters 12:2213-2215; Sun et al (2003) Bioorganic & Medicinal Chemistry 11:1761-1768). Dendritic linkers can increase the molar ratio of drug to antibody, i.e., loading, which is related to the potency of the ADC. Thus, where an antibody bears only one reactive cysteine thiol group, a multitude of drug moieties may be attached through a dendritic linker.

Nonlimiting exemplary linkers are shown below for ADCs of Formula (Ig):

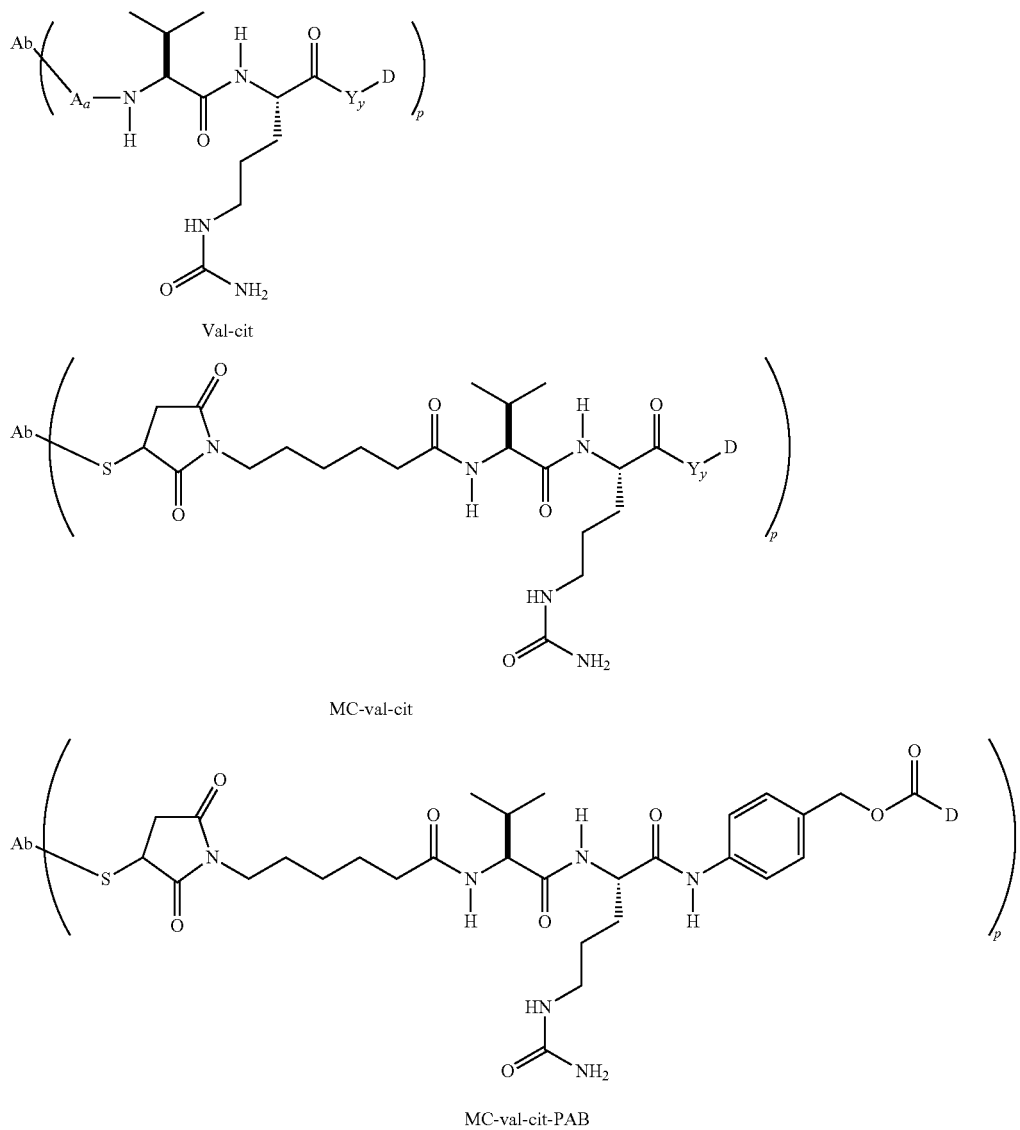

Val-cit

MC-val-cit

MC-val-cit-PAB

-continued

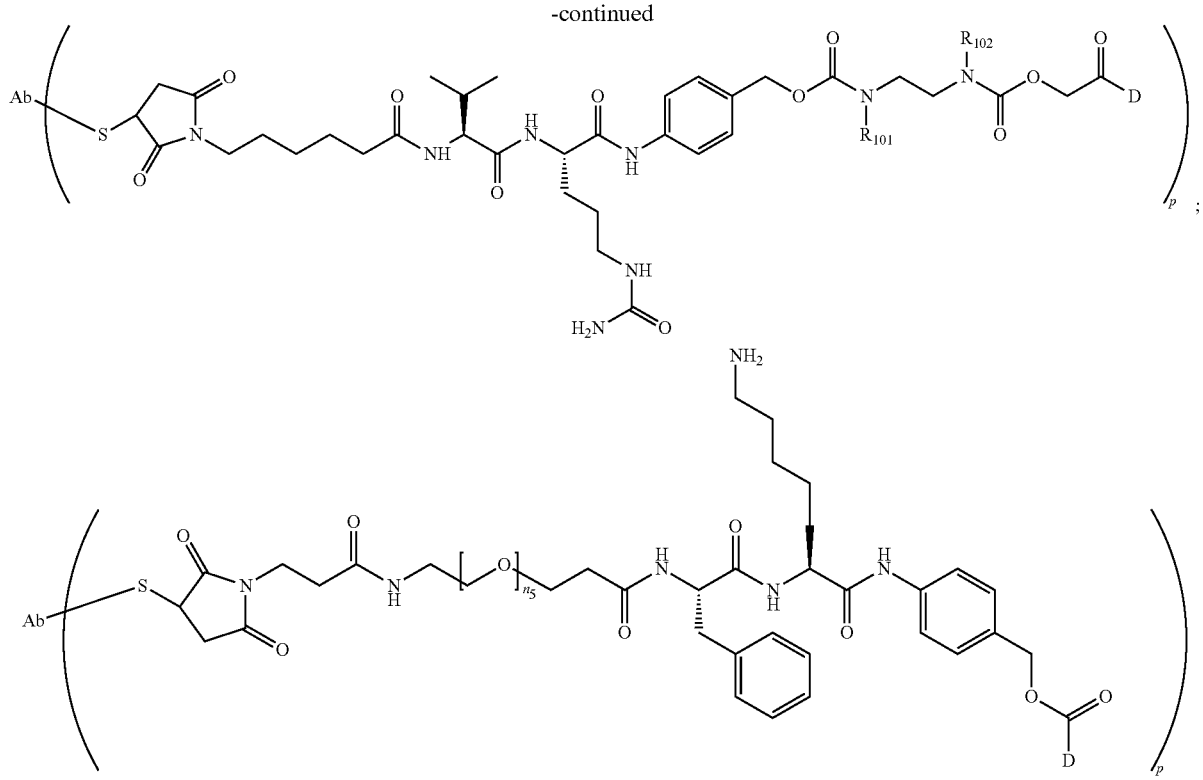

Phe-Lys-PAB-Ab wherein $R_{101}$ and $R_{102}$ are independently selected from H and $C_1$-$C_6$ alkyl;

$n_5$ is an integer from 0 to 12.

In some embodiments, n is an integer 2 to 10. In some embodiments, n is an integer from 4 to 8.

In some embodiments, $R_{101}$ and $R_{102}$ are each —$CH_3$.

Further nonlimiting exemplary ADCs include the structures:

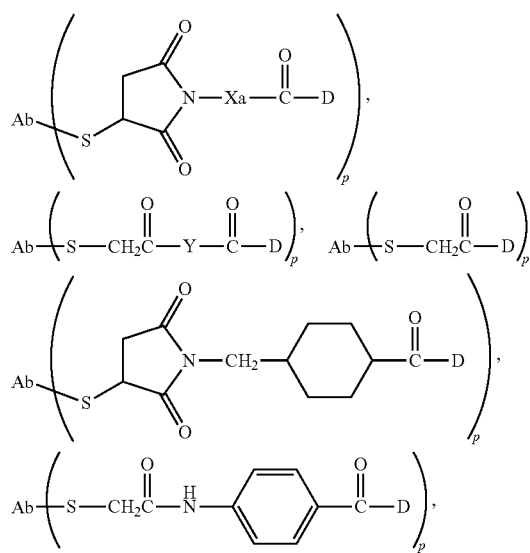

wherein Xa is:

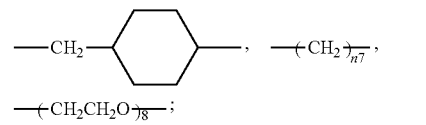

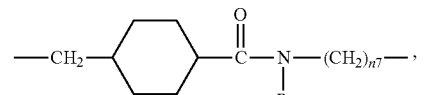

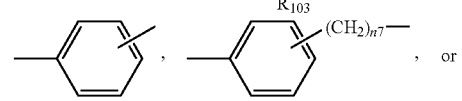

Y is:

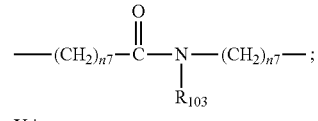

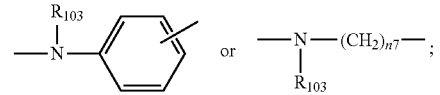

each $R_{103}$ is independently H or $C_1$-$C_6$ alkyl; and n7 is an integer from 1 to 12.

In some embodiments, a linker is substituted with groups that modulate solubility and/or reactivity. As a nonlimiting example, a charged substituent such as sulfonate (—$SO_3^-$) or ammonium may increase water solubility of the linker reagent and facilitate the coupling reaction of the linker reagent with the antibody and/or the drug moiety, or facilitate the coupling reaction of Ab-L (antibody-linker intermediate) with D, or D-L (drug-linker intermediate) with Ab, depending on the synthetic route employed to prepare the ADC. In some embodiments, a portion of the linker is coupled to the antibody and a portion of the linker is coupled to the drug, and then the Ab-(linker portion) a is coupled to drug-(linker portion)[b] to form the ADC of Formula Ig.

The compounds disclosed herein expressly contemplate, but are not limited to, ADC prepared with the following linker reagents: bis-maleimido-trioxyethylene glycol (BMPEO), N-(β-maleimidopropyloxy)-N-hydroxy succinimide ester (BMPS), N-(ε-maleimidocaproyloxy) succinimide ester (EMCS), N-[γ-maleimidobutyryloxy]succinimide ester (GMBS), 1,6-hexane-bis-vinylsulfone (HBVS), succinimidyl 4-(N-maleimidomethyl)cyclohexane-1-carboxy-(6-amidocaproate) (LC-SMCC), m-maleimidobenzoyl-N-hydroxysuccinimide ester (MBS), 4-(4-N-Maleimidophenyl)butyric acid hydrazide (MPBH), succinimidyl 3-(bromoacetamido)propionate (SBAP), succinimidyl iodoacetate (SIA), succinimidyl (4-iodoacetyl) aminobenzoate (SIAB), N-succinimidyl-3-(2-pyridyldithio) propionate (SPDP), N-succinimidyl-4-(2-pyridylthio)pentanoate (SPP), succinimidyl 4-(N-maleimidomethyl)cyclohexane-1-carboxylate (SMCC), succinimidyl 4-(p-maleimidophenyl)butyrate (SMPB), succinimidyl 6-[(β-maleimidopropionamido)hexanoate](SMPH), iminothiolane (IT), sulfo-EMCS, sulfo-GMBS, sulfo-KMUS, sulfo-MBS, sulfo-SIAB, sulfo-SMCC, and sulfo-SMPB, and succinimidyl-(4-vinylsulfone)benzoate (SVSB), and including bis-maleimide reagents: dithiobismaleimidoethane (DTME), 1,4-Bismaleimidobutane (BMB), 1,4 Bismaleimidyl-2,3-dihydroxybutane (BMDB), bismaleimidohexane (BMH), bis-maleimidoethane (BMOE), BM(PEG)$_2$ (shown below), and BM(PEG)$_3$ (shown below); bifunctional derivatives of imidoesters (such as dimethyl adipimidate HCl), active esters (such as disuccinimidyl suberate), aldehydes (such as glutaraldehyde), bis-azido compounds (such as bis-(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). In some embodiments, bis-maleimide reagents allow the attachment of the thiol group of a cysteine in the antibody to a thiol-containing drug moiety, linker, or linker-drug intermediate. Other functional groups that are reactive with thiol groups include, but are not limited to, iodoacetamide, bromoacetamide, vinyl pyridine, disulfide, pyridyl disulfide, isocyanate, and isothiocyanate.

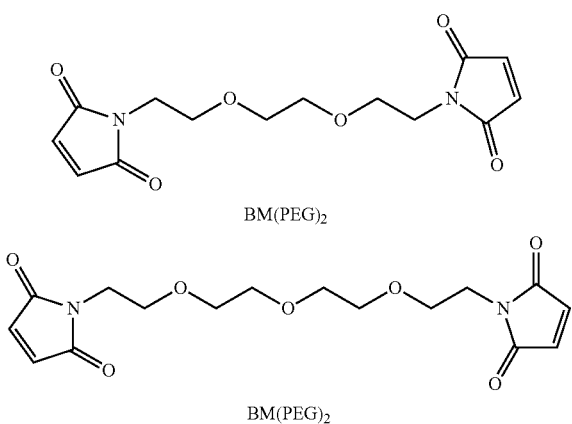

BM(PEG)$_2$

BM(PEG)$_2$

Certain useful linker reagents can be obtained from various commercial sources, such as Pierce Biotechnology, Inc. (Rockford, Ill.), Molecular Biosciences Inc. (Boulder, Colo.), or synthesized in accordance with procedures described in the art; for example, in Toki et al (2002) J. Org. Chem. 67:1866-1872; Dubowchik, et al. (1997) Tetrahedron Letters, 38:5257-60; Walker, M. A. (1995) J. Org. Chem. 60:5352-5355; Frisch et al (1996) Bioconjugate Chem. 7:180-186; U.S. Pat. No. 6,214,345; WO 02/088172; US 2003130189; US2003096743; WO 03/026577; WO 03/043583; and WO 04/032828.

Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO 94/11026.

Methods of Making Polymer NaPi2b-Targeted Antibody Conjugates:

In certain embodiments, the conjugates are formed in several steps. These steps include (1) modifying a polymer so that it contains a functional group that can react with a functional group of the drug or its derivative; (2) reacting the modified polymer with the drug or its derivative so that the drug is linked to the polymer; (3) modifying the polymer-drug conjugate so that the polymer contains a functional group that can react with a functional group of the isolated NaPi2b-targeted antibody or its derivative; and (4) reacting the modified polymer-drug conjugate with the NaPi2b-targeted antibody to form the conjugate disclosed herein. Step (3) may be omitted if the modified polymer produced by step (1) contains a functional group that can react with a functional group of the antibody.

In another embodiment the conjugates are formed in several steps: (1) modifying a polymer so that it contains a functional group that can react with a functional group of a first drug or its derivative; (2) reacting the modified polymer with the first drug or its derivative so that the first drug is linked to the polymer; (3) modifying the polymer-drug conjugate so that it contains a different functional group that can react with a functional group of a second drug or its derivative (4) reacting the modified polymer-drug conjugate with the second drug or its derivative so that the second drug is linked to the polymer-drug conjugate; (5) modifying the polymer-drug conjugate containing 2 different drugs so that the polymer contains a functional group that can react with a functional group of the NaPi2b-targeted antibody; and (6) reacting the modified polymer-drug conjugate of step (5) with the isolated NaPi2b-targeted antibody or its derivative to form the conjugate disclosed herein. Steps (5) and (6) may be repeated if 2 different isolated NaPi2b-targeted antibodies or their derivatives are to be conjugated to form a polymer-drug conjugate comprising two different drugs and two different antibodies.

In yet another embodiment, the conjugates are formed in several steps. These steps include (1) modifying a polymer so that it contains a functional group that can react with a functional group of the drug or its derivative; (2) further modifying the polymer so that it also contains a functional group that can react with a functional group of the NaPi2b-targeted antibody; (3) reacting the modified polymer with the drug or its derivative so that the drug is linked to the polymer; and (4) reacting the modified polymer-drug conjugate with the NaPi2b-targeted antibody to form the conjugate disclosed herein. The sequence of steps (1) and (2) or that of steps (3) and (4) can be reversed. Further either step (1) or (2) may be omitted if the modified polymer contains a functional group that can react with both a functional group of the drug or its derivatives and a functional group of the NaPi2b-targeted antibody.

In another embodiment the conjugates are formed in several steps: (1) modifying a polymer so that it contains a functional group that can react with a functional group of a first drug or its derivative; (2) further modifying a polymer so that it contains a functional group that can react with a functional group of the NaPi2b-targeted antibody; (3) reacting the modified polymer with the first drug or its derivative so that the first drug is linked to the polymer; (4) modifying the polymer-drug conjugate so that it contains a different functional group that can react with a functional group of a second drug or its derivative (5) reacting the modified polymer-drug conjugate with the second drug or its derivative so that the second drug is linked to the polymer-drug conjugate; (6) reacting the modified polymer-drug conjugate containing 2 different drugs so that the polymer with the isolated NaPi2b-targeted antibody or its derivative to form the conjugate disclosed herein. Step (6) may be repeated if 2 different isolated antibodies or their derivatives are to be conjugated to form a polymer-drug conjugate comprising two different drugs and two different antibodies. Step (4) may be carried out after step (1) so that the modified polymer contains two different functional groups that can react with two different drugs or their derivatives. In this embodiment, the modified polymer containing two different functional group that can react with two different drugs or their derivatives can be further modified so that it contains a functional group that can react with a functional group of the antibody; prior to the reaction of the modified polymer with either the two different drugs (step (3) and step (5) or antibody (step (6).

In certain exemplary embodiments, the conjugates disclosed herein find use in biomedical applications, such as drug delivery and tissue engineering, and the polymeric carrier is biocompatible and biodegradable. In certain embodiments, the carrier is a soluble polymer, nanoparticle, gel, liposome, micelle, suture, implant, etc. In certain embodiments, the term "soluble polymer" encompasses biodegradable biocompatible polymer such as a polyal (e.g., hydrophilic polyacetal or polyketal). In certain other embodiments, the carrier is a fully synthetic, semi-synthetic or naturally-occurring polymer. In certain other embodiments, the carrier is hydrophilic. Examples of suitable polymeric carrier for producing the conjugates disclosed herein are described in U.S. Pat. No. 8,815,226, the content of which is hereby incorporated by reference in its entirety.

In one embodiment, the polymeric carrier comprises units of Formula (IV):

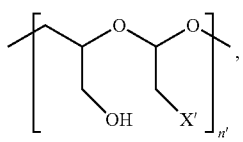
(IV)

wherein X' indicates the substituent for the hydroxyl group of the polymer backbone. As shown in Formula (IV) and the other formulae described herein, each polyacetal unit has a single hydroxyl group attached to the glycerol moiety of the unit and an X' group attached to the glycolaldehyde moiety of the unit. This is for convenience only and it should be construed that the polymer having units of Formula (IV) and other formulae described herein can contain a random distribution of units having a X' group (or another substituent such as a linker comprising a maleimide terminus) attached to the glycolaldehyde moiety of the units and those having a single X' group (or another substituent such as a linker comprising a maleimide terminus) attached to the glycerol moiety of the units as well as units having two X' groups (or other substituents such as a linker comprising a maleimide terminus) with one attached to the glycolaldehyde moiety and the other attached to the glycerol moiety of the units.

In one embodiment, biodegradable biocompatible polyals suitable for practicing the present disclosure have a molecular weight of between about 2 and about 40 kDa, between about 6 and about 20 kDa, or between about 8 and about 15 kDa). For example, the biodegradable biocompatible polyal used for the polymer scaffold or conjugate disclosed herein is PHF having a molecular weight of between about 2 and about 40 kDa (e.g., about 2-20 kDa, 3-15 kDa, or 5-10 kDa.)

Methods for preparing polymer carriers (e.g., biocompatible, biodegradable polymer carriers) suitable for conjugation to modifiers are known in the art. For example, synthetic guidance can be found in U.S. Pat. Nos. 5,811,510; 5,863, 990; 5,958,398; 7,838,619; 7,790,150; and 8,685,383. The skilled practitioner will know how to adapt these methods to make polymer carriers for use in the practice of the disclosure.

In one embodiment, a method for forming the biodegradable biocompatible polyal conjugates of the present disclosure comprises a process by which a suitable polysaccharide is combined with an efficient amount of a glycol-specific oxidizing agent to form an aldehyde intermediate. The aldehyde intermediate, which is a polyal itself, may then be reduced to the corresponding polyol, succinylated, and coupled with one or more suitable modifiers to form a biodegradable biocompatible polyal conjugate comprising succinamide-containing linkages.

In another preferred embodiment, fully synthetic biodegradable biocompatible polyals for used in the present disclosure can be prepared by reacting a suitable initiator with a suitable precursor compound.

For example, fully synthetic polyals may be prepared by condensation of vinyl ethers with protected substituted diols. Other methods, such as cycle opening polymerization, may be used, in which the method efficacy may depend on the degree of substitution and bulkiness of the protective groups.

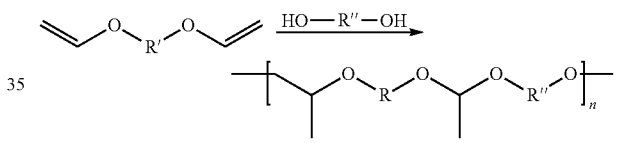

One of ordinary skill in the art will appreciate that solvent systems, catalysts and other factors may be optimized to obtain high molecular weight products.

In certain embodiments, the carrier is PHF.

In embodiments, the polymer carrier is PHF having a polydispersity index (PDI) of ≤1.5, e.g., <1.4, <1.3, <1.2 or <1.1.

For example, for conjugating the isolated NaPi2b-targeted antibody having a molecular weight of 40 kDa to 200 kDa, the polymeric carrier of the scaffold is a polyacetal, e.g., a PHF having a molecular weight (i.e., MW of the unmodified PHF) ranging from about 2 kDa to about 40 kDa (e.g., about 2-20 kDa, or about 3-15 kDa, or about 5-10 kDa).

For example, for conjugating the antibody having a molecular weight of 40 kDa to 80 kDa, the polymeric carrier of the scaffold disclosed herein is a polyacetal, e.g., a PHF having a molecular weight (i.e., MW of the unmodified PHF) ranging from about 2 kDa to about 40 kDa (e.g., about 2-20 kDa, or about 3-15 kDa, or about 5-10 kDa). For example the PHF has a molecular weight of about 5 kDa, 6 kDa, 7 kDa, 8 kDa, 9 kDa, 10 kDa, 11 kDa, 12 kDa, 13 kDa, 14 kDa, or 15 kDa.

For example, for conjugating the antibody having a molecular weight of 60 kDa to 120 kDa, the polymeric carrier of the scaffold disclosed herein is a polyacetal, e.g., a PHF having a molecular weight (i.e., MW of the unmodified PHF) ranging from about 2 kDa to about 40 kDa (e.g., about 2-20 kDa, or about 3-15 kDa, or about 5-10 kDa). For example the PHF has a molecular weight of about 5 kDa, 6 kDa, 7 kDa, 8 kDa, 9 kDa, 10 kDa, 11 kDa, 12 kDa, 13 kDa, 14 kDa, or 15 kDa.

For example, for conjugating the antibody having a molecular weight of 140 kDa to 180 kDa or of 140 kDa to 150 kDa, the polymeric carrier of the scaffold disclosed herein is a polyacetal, e.g., a PHF having a molecular weight (i.e., MW of the unmodified PHF) ranging from about 2 kDa to about 40 kDa (e.g., about 2-20 kDa, or about 3-15 kDa, or about 5-10 kDa). For example the PHF has a molecular weight of about 5 kDa, 6 kDa, 7 kDa, 8 kDa, 9 kDa, 10 kDa, 11 kDa, 12 kDa, 13 kDa, 14 kDa, or 15 kDa.

The antibody thereof in this molecular weight range, includes but are not limited to, for example, full length antibodies, such as, IgG, IgM.

The biodegradable biocompatible conjugates disclosed herein can be prepared to meet desired requirements of biodegradability and hydrophilicity. For example, under physiological conditions, a balance between biodegradability and stability can be reached. For instance, it is known that molecules with molecular weights beyond a certain threshold (generally, above 40-100 kDa, depending on the physical shape of the molecule) are not excreted through kidneys, as small molecules are, and can be cleared from the body only through uptake by cells and degradation in intracellular compartments, most notably lysosomes. This observation exemplifies how functionally stable yet biodegradable materials may be designed by modulating their stability under general physiological conditions (pH=7.5±0.5) and at lysosomal pH (pH near 5). For example, hydrolysis of acetal and ketal groups is known to be catalyzed by acids, therefore polyals will be in general less stable in acidic lysosomal environment than, for example, in blood plasma. One can design a test to compare polymer degradation profile at, for example, pH=5 and pH=7.5 at 37° C. in aqueous media, and thus to determine the expected balance of polymer stability in normal physiological environment and in the "digestive" lysosomal compartment after uptake by cells. Polymer integrity in such tests can be measured, for example, by size exclusion HPLC. One skilled on the art can select other suitable methods for studying various fragments of the degraded conjugates disclosed herein.

In many cases, it will be preferable that at pH=7.5 the effective size of the polymer will not detectably change over 1 to 7 days, and remain within 50% from the original for at least several weeks. At pH=5, on the other hand, the polymer should preferably detectably degrade over 1 to 5 days, and be completely transformed into low molecular weight fragments within a two-week to several-month time frame. Although faster degradation may be in some cases preferable, in general it may be more desirable that the polymer degrades in cells with the rate that does not exceed the rate of metabolization or excretion of polymer fragments by the cells. Accordingly, in certain embodiments, the conjugates of the present disclosure are expected to be biodegradable, in particular upon uptake by cells, and relatively "inert" in relation to biological systems. The products of carrier degradation are preferably uncharged and do not significantly shift the pH of the environment. It is proposed that the abundance of alcohol groups may provide low rate of polymer recognition by cell receptors, particularly of phagocytes. The polymer backbones of the present disclosure generally contain few, if any, antigenic determinants (characteristic, for example, for some polysaccharides and polypeptides) and generally do not comprise rigid structures capable of engaging in "key-and-lock" type interactions in vivo unless the latter are desirable. Thus, the soluble, crosslinked and solid conjugates disclosed herein are predicted to have low toxicity and bioadhesivity, which makes them suitable for several biomedical applications.

In certain embodiments of the present disclosure, the biodegradable biocompatible conjugates can form linear or branched structures. For example, the biodegradable biocompatible polyal conjugates of the present disclosure can be chiral (optically active). Optionally, the biodegradable biocompatible polyal conjugates of the present disclosure can be scalemic.

In certain embodiments, the conjugates disclosed herein are water-soluble. In certain embodiments, the conjugates disclosed herein are water-insoluble. In certain embodiments, the inventive conjugate is in a solid form. In certain embodiments, the conjugates disclosed herein are colloids. In certain embodiments, the conjugates disclosed herein are in particle form. In certain embodiments, the conjugates disclosed herein are in gel form.

Scheme 1 below shows a synthetic scheme of making a polymeric drug scaffold disclosed herein. In one embodiment, the conjugates are formed in several steps: (1) the polymer, PHF is modified to contain a COOH moiety (e.g., —C(O)—X—$(CH_2)_2$—COOH); (2) the polymer is then further modified so that it contains a maleimido moiety (e.g., EG2-MI) that can react with a functional group of a PBRM; (3) the modified polymer, containing two different functional groups, is reacted with a functional group of a drug or its derivative (e.g., AF-HPA-Ala) to form a polymer-drug conjugate; (4) the disulfide bonds of a PBRM are reduced; (5) the reduced PBRM is then reacted with the polymer-drug conjugate to form the protein-polymer-drug conjugate; and (6) the remaining maleimido moieties are optionally reacted with a maleimido blocking compound (e.g., cysteine).

In another embodiment the order of steps (2) and (3) can be reversed as depicted in the right side route in Scheme 1 below.

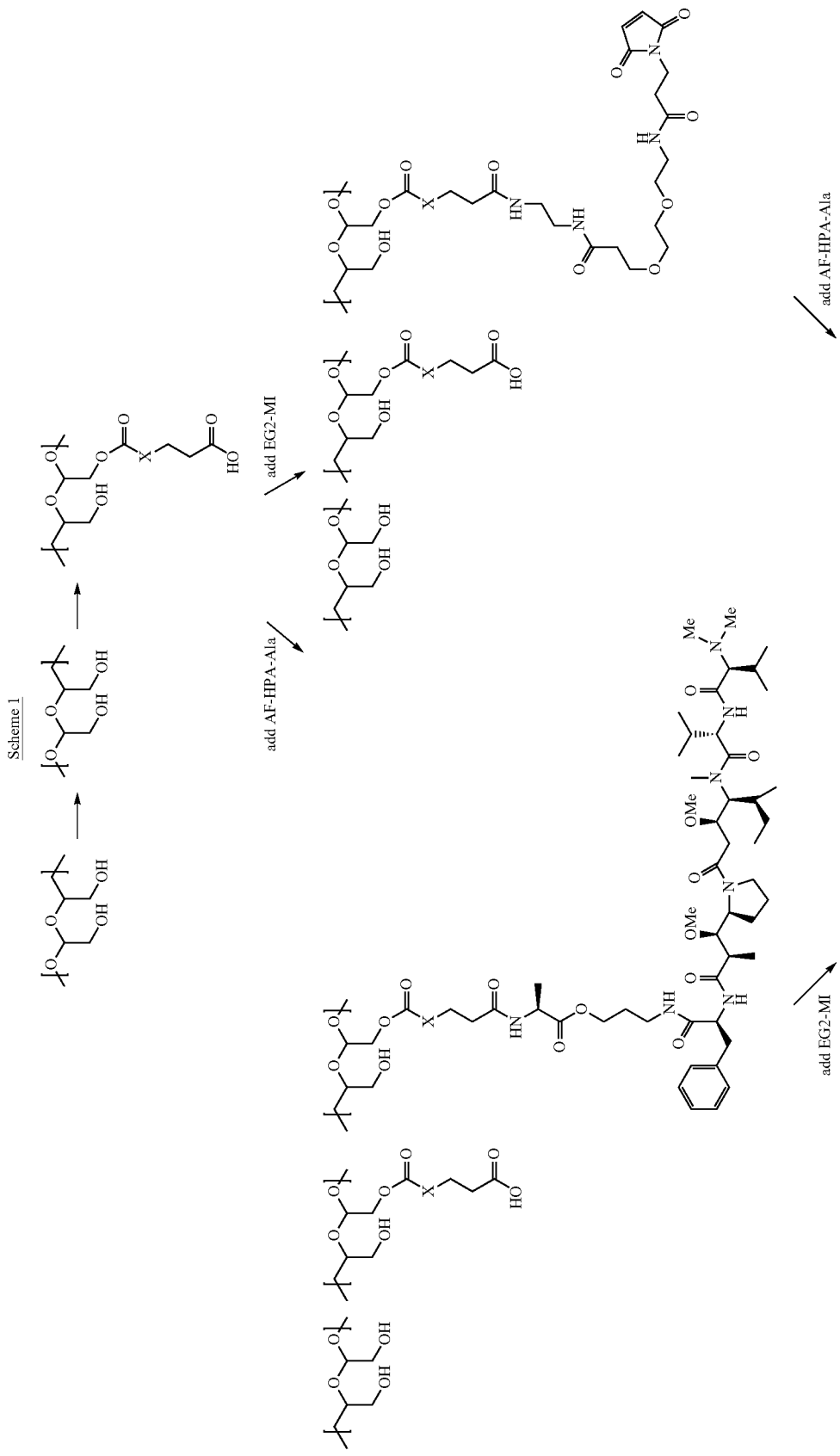
Scheme 1

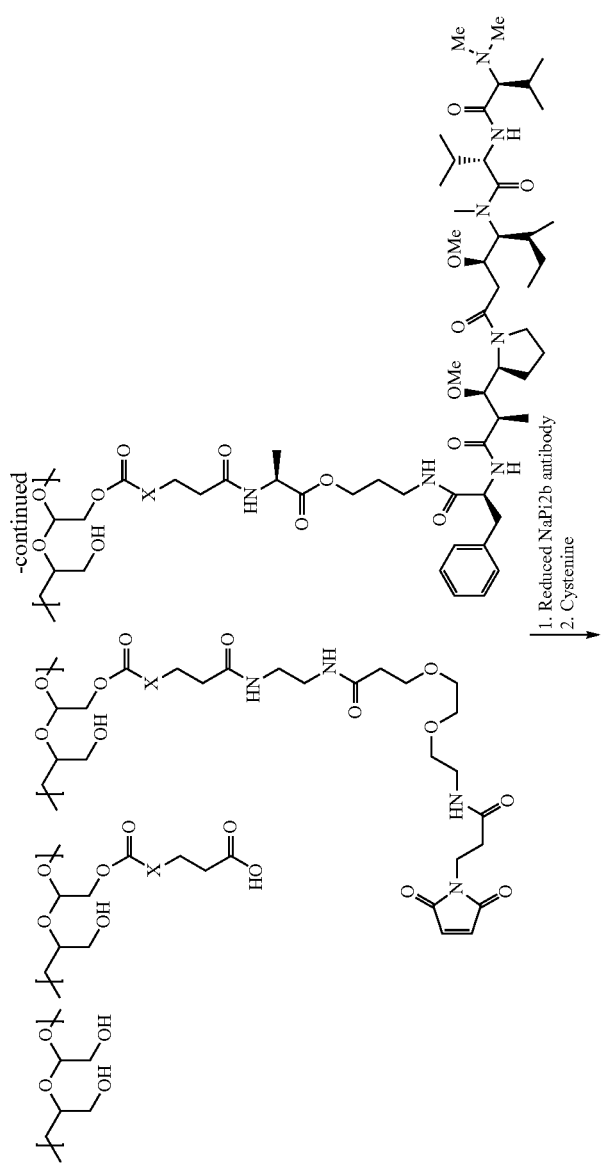
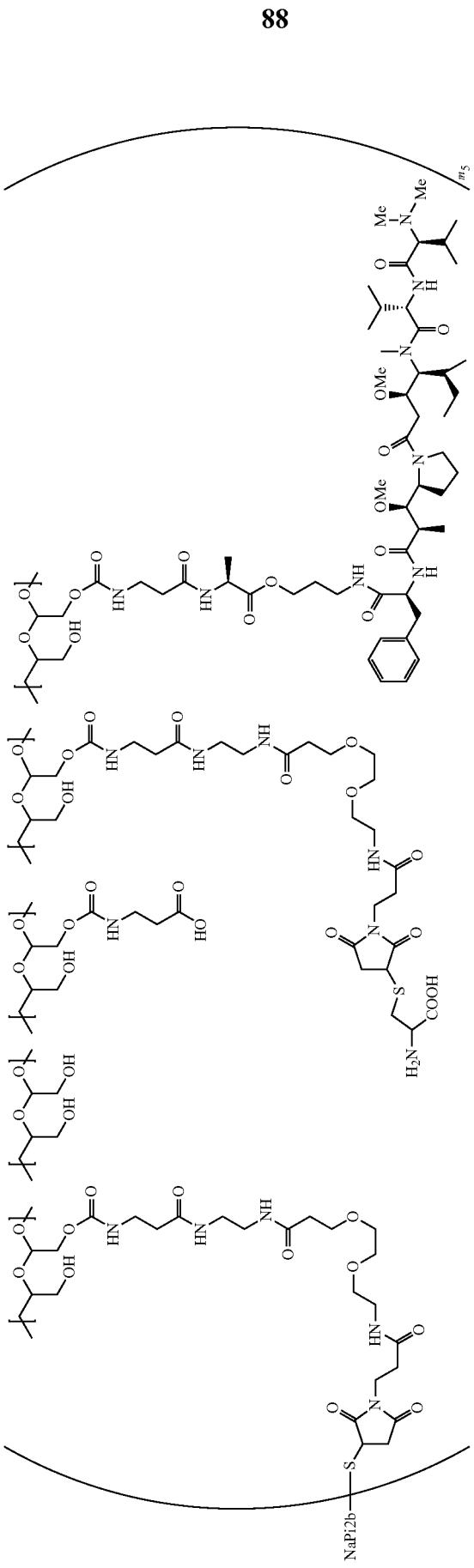

In yet another embodiment, steps (2) and (3) above are carried out simultaneously as depicted in Scheme 2 below.

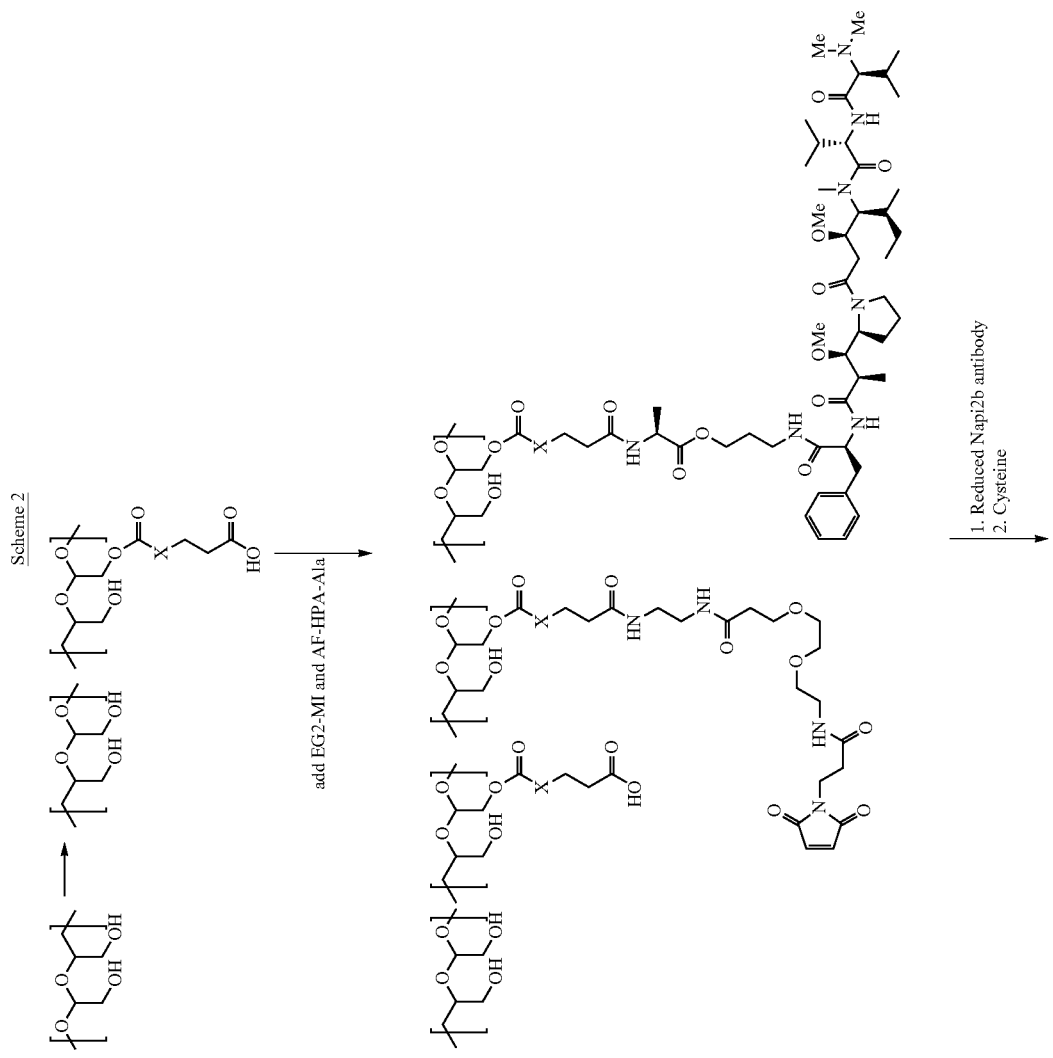

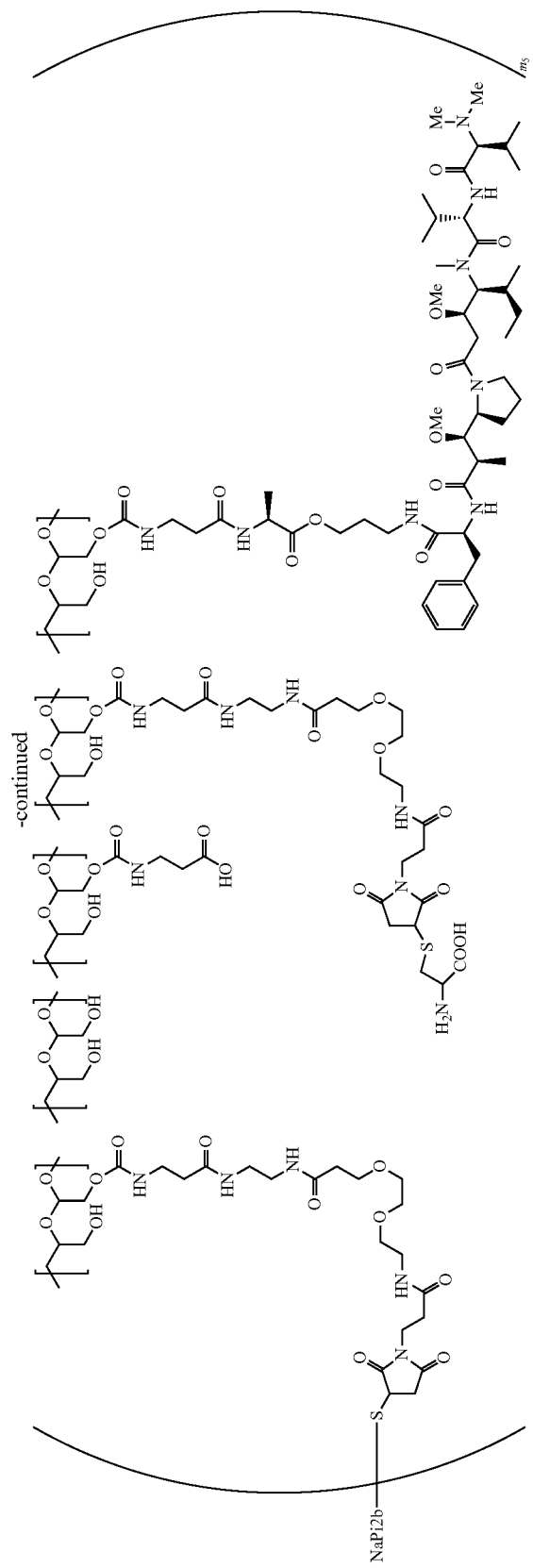

Use of NaPi2b-Targeted Antibody-Drug Conjugates

It will be appreciated that administration of therapeutic entities in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed., Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

In one embodiment, the NaPi2b antibody conjugates disclosed herein may be used as therapeutic agents. Such agents will generally be employed to diagnose, prognose, monitor, treat, alleviate, prevent, and/or delay the progression of a disease or pathology associated with, e.g., an aberrant NaPi2b activity and/or expression in a subject. A therapeutic regimen is carried out by identifying a subject, e.g., a human patient suffering from (or at risk of developing) a disease or disorder associated with aberrant NaPi2b activity and/or expression, e.g., a cancer, using standard methods. NaPi2b antibody conjugate preparation, preferably one having high specificity and high affinity for its target antigen, is administered to the subject and will generally have an effect due to its binding with the target. Administration of the conjugate may abrogate or inhibit or interfere with the signaling function of the target. Administration of the conjugate may abrogate or inhibit or interfere with the binding of the target with an endogenous ligand to which it naturally binds. For example, the conjugate can bind to the target and modulate, block, inhibit, reduce, antagonize, neutralize, or otherwise interfere with NaPi2b activity and/or expression.

Diseases or disorders related to aberrant NaPi2b activity and/or expression include but not limited to cancer. The target cancer can be ovarian cancer such as epithelial ovarian cancer, thyroid cancer, colorectal cancer, lung cancer, non-small cell lung cancer (NSCLC) such as non-squamous NSCLC, breast cancer, kidney cancer and salivary duct carcinoma.

In another aspect, diseases or disorders are cancer selected from the group consisting of non-small cell lung cancer (NSCLC) such as non-squamous NSCLC and ovarian cancer such as epithelial ovarian cancer. Generally, alleviation or treatment of a disease or disorder involves the lessening of one or more symptoms or medical problems associated with the disease or disorder. For example, in the case of cancer, the therapeutically effective amount of the conjugate or a pharmaceutical composition thereof can accomplish one or a combination of the following: reduce the number of cancer cells; reduce the tumor size; inhibit (i.e., to decrease to some extent and/or stop) cancer cell infiltration into peripheral organs; inhibit tumor metastasis; inhibit, to some extent, tumor growth; and/or relieve to some extent one or more of the symptoms associated with the cancer. In some embodiments, a composition disclosed herein can be used to prevent the onset or reoccurrence of the disease or disorder in a subject.

A therapeutically effective amount of a NaPi2b antibody conjugate disclosed herein relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. The dosage regimen utilizing the conjugates disclosed herein is also selected in accordance with a variety of other factors including type, species, age, weight, sex and medical condition of the patient; the severity of the condition to be treated; the route of administration; the renal and hepatic function of the patient; and the particular conjugate employed. An ordinarily skilled physician or veterinarian can readily determine and prescribe the effective amount of the conjugate required to prevent, counter or arrest the progress of the condition. Common ranges for therapeutically effective dosing of a NaPi2b antibody conjugate disclosed herein may be, by way of nonlimiting example, from about 0.1 mg/kg body weight to about 50 mg/kg body weight, from about 0.1 mg/kg body weight to about 100 mg/kg body weight or from about 0.1 mg/kg body weight to about 150 mg/kg body weight. Ranges disclosed herein are expressed as amount administered based on the subject's weight, and one skilled in the art can easily express it as amount administered per body surface area of the subject. For example, 1 mg/kg body weight for a human adult is equivalent to about 37 mg/m$^2$ and 1 mg/kg body weight for a human child is equivalent to about 25 mg/m$^2$.

Common dosing frequencies may range, for example, from twice daily to once a month (e.g., once daily, once weekly; once every other week; once every 3 weeks or monthly). For example, conjugates of XMT 1535 or 10H1.11.4B disclosed herein can be administered (e.g., as a single dose weekly, every 2 weeks, every 3 weeks, or monthly) at about 0.1 mg/kg to about 20 mg/kg (e.g., 0.2 mg/kg, 0.4 mg/kg, 0.5 mg/kg, 0.67 mg/kg, 0.8 mg/kg, 1 mg/kg, 1.25 mg/kg, 1.67 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, or 20 mg/kg). For example, conjugates of XMT 1535 or 10H1.11.4B disclosed herein can be administered (e.g., as a single dose weekly, every 2 weeks, every 3 weeks, or monthly) at about 0.1 mg/kg to about 20 mg/kg (e.g., 0.2 mg/kg, 0.4 mg/kg, 0.5 mg/kg, 0.67 mg/kg, 0.8 mg/kg, 1 mg/kg, 1.25 mg/kg, 1.67 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, or 20 mg/kg) for treating NaPi2b-expressing ovarian cancer or NaPi2b-expressing NSCLC cancer.

Efficaciousness of treatment is determined in association with any known method for diagnosing or treating the particular NaPi2b-related disorder. Alleviation of one or more symptoms of the NaPi2b-related disorder indicates that the antibody confers a clinical benefit.

Methods for the screening of antibodies that possess the desired specificity include, but are not limited to, enzyme linked immunosorbent assay (ELISA) and other immunologically mediated techniques known within the art.

Therapeutic Administration and Formulations of NaPi2b-Targeted Antibody-Drug Conjugates The conjugates disclosed herein (also referred to herein as "active compounds"), can be incorporated into pharmaceutical compositions suitable for administration. Principles and considerations involved in preparing such compositions, as well as guidance in the choice of components are provided, for example, in Remington's Pharmaceutical Sciences: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Such compositions typically comprise the antibody and/or conjugates thereof and a pharmaceutically acceptable carrier.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated.

The formulations to be used for in vivo administration must be sterile. This is readily accomplished by filtration through sterile filtration membranes.

A pharmaceutical composition disclosed herein is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a conjugate disclosed herein) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a sustained/controlled release formulations, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

For example, the active ingredients can be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

The materials can also be obtained commercially from Alza Corporation and Nova Pharmaceuticals, Inc. Liposomal suspensions (including liposomes targeted to infected cells with monoclonal antibodies to viral antigens) and can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms disclosed herein are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

In one embodiment, the active compounds are administered in combination therapy, i.e., combined with other agents, e.g., therapeutic agents, that are useful for treating pathological conditions or disorders, such as various forms of cancer, autoimmune disorders and inflammatory diseases. The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

For example, the combination therapy can include one or more conjugates disclosed herein coformulated with, and/or coadministered with, one or more additional antibodies e.g., a NaPi2b antibody, which can be the same as the antibody used to form the conjugate or a different antibody.

For example, the combination therapy can include one or more therapeutic agent and/or adjuvant. In certain embodiments, the additional therapeutic agent is a small molecule inhibitor, another antibody-based therapy, a polypeptide or peptide-based therapy, a nucleic acid-based therapy and/or other biologic.

In certain embodiments, the additional therapeutic agent is a cytotoxic agent, a chemotherapeutic agent, a growth inhibitory agent, an angiogenesis inhibitor, a PARP (poly (ADP)-ribose polymerase) inhibitor, an alkylating agent, an anti-metabolite, an anti-microtubule agent, a topoisomerase inhibitor, a cytotoxic antibiotic, any other nucleic acid damaging agent or an immune checkpoint inhibitor. In one embodiment, the therapeutic agent used in the treatment of cancer, includes but is not limited to, a platinum compound (e.g., cisplatin or carboplatin); a taxane (e.g., paclitaxel or docetaxel); a topoisomerase inhibitor (e.g., irinotecan or topotecan); an anthracycline (e.g., doxorubicin (ADRIAMYCIN®) or liposomal doxorubicin (DOXIL®)); an anti-metabolite (e.g., gemcitabine, pemetrexed); cyclophosphamide; vinorelbine (NAVELBINE®); hexamethylmelamine; ifosfamide; etoposide; an angiogenesis inhibitor (e.g., Bevacizumab (Avastin®)), thalidomide, TNP-470, platelet factor 4, interferon or endostatin); a PARP inhibitor (e.g., Olaparib (Lynparza™)); an immune checkpoint inhibitor, such as for example, a monoclonal antibody that targets either PD-1 or PD-L ((Pembrolizumab (Keytruda®), atezolizumab (MPDL3280A) or Nivolumab (Opdivo®)) or CTA-4 (Ipilimumab (Yervoy®), a kinase inhibitor (e.g., sorafenib or erlotinib), a proteasome inhibitor (e.g., bortezomib or carfilzomib), an immune modulating agent (e.g., lenalidomide or IL-2), a radiation agent, an ALK inhibitor (e.g. crizotinib (Xalkori), ceritinib (Zykadia), alectinib (Alecensa), dalantercept (ACE-041), brigatinib (AP26113), entrectinib (NMS-E628), PF-06463922 TSR-011, CEP-37440 and X-396) and/or a biosimilar thereof and/or combinations thereof. Other suitable agents include an agent considered standard of care by those skilled in the art and/or a chemotherapeutic agent well known to those skilled in the art.

In some embodiments, the immune checkpoint inhibitor is an inhibitor of CTLA-4. In some embodiments, the immune checkpoint inhibitor is an antibody against CTLA-4. In some embodiments, the immune checkpoint inhibitor is a monoclonal antibody against CTLA-4. In other embodiments, the immune checkpoint inhibitor is a human or humanized antibody against CTLA-4. In one embodiment, the anti-CTLA-4 antibody blocks the binding of CTLA-4 to CD80 (B7-1) and/or CD86 (B7-2) expressed on antigen presenting cells. Exemplary antibodies against CTLA-4 include, but are not limited to, Bristol Meyers Squibb's anti-CTLA-4 antibody ipilimumab (also known as Yervoy®, MDX-010, BMS-734016 and MDX-101); anti-CTLA4 Antibody, clone 9H10 from Millipore; Pfizer's tremelimumab (CP-675,206, ticilimumab); and anti-CTLA4 antibody clone BNI3 from Abcam.

In some embodiments, the anti-CTLA-4 antibody is an anti-CTLA-4 antibody disclosed in any of the following patent publications (herein incorporated by reference): WO 2001014424; WO 2004035607; US2005/0201994; EP 1212422 B1; WO2003086459; WO2012120125; WO2000037504; WO2009100140; WO200609649; WO2005092380; WO2007123737; WO2006029219; WO20100979597; WO200612168; and WO1997020574. Additional CTLA-4 antibodies are described in U.S. Pat. Nos. 5,811,097, 5,855,887, 6,051,227, and 6,984,720; in PCT Publication Nos. WO 01/14424 and WO 00/37504; and in U.S. Publication Nos. 2002/0039581 and 2002/086014; and/or U.S. Pat. Nos. 5,977,318, 6,682,736, 7,109,003, and 7,132,281, incorporated herein by reference). In some embodiments, the anti-CTLA-4 antibody is for example, those disclosed in: WO 98/42752; U.S. Pat. Nos. 6,682,736 and 6,207,156; Hurwitz et al, Proc. Natl. Acad. Sci. USA, 95(17): 10067-10071 (1998); Camacho et al, J. Clin. Oncol., 22(145): Abstract No. 2505 (2004) (antibody CP-675206); Mokyr et al, Cancer Res., 58:5301-5304 (1998) (incorporated herein by reference).

In some embodiments, the CTLA-4 inhibitor is a CTLA-4 ligand as disclosed in WO1996040915.

In some embodiments, the CTLA-4 inhibitor is a nucleic acid inhibitor of CTLA-4 expression. For example, anti-CTLA4 RNAi molecules may take the form of the molecules described by Mello and Fire in PCT Publication Nos. WO 1999/032619 and WO 2001/029058; U.S. Publication Nos. 2003/0051263, 2003/0055020, 2003/0056235, 2004/265839, 2005/0100913, 2006/0024798, 2008/0050342, 2008/0081373, 2008/0248576, and 2008/055443; and/or U.S. Pat. Nos. 6,506,559, 7,282,564, 7,538,095, and 7,560,438 (incorporated herein by reference). In some instances, the anti-CTLA4 RNAi molecules take the form of double stranded RNAi molecules described by Tuschl in European Patent No. EP 1309726 (incorporated herein by reference). In some instances, the anti-CTLA4 RNAi molecules take the form of double stranded RNAi molecules described by Tuschl in U.S. Pat. Nos. 7,056,704 and 7,078,196 (incorporated herein by reference). In some embodiments, the CTLA4 inhibitor is an aptamer described in PCT Publication No. WO2004081021.

Additionally, the anti-CTLA4 RNAi molecules of the present disclosure may take the form be RNA molecules described by Crooke in U.S. Pat. Nos. 5,898,031, 6,107,094, 7,432,249, and 7,432,250, and European Application No. EP 0928290 (incorporated herein by reference).

In some embodiments, the immune checkpoint inhibitor is an inhibitor of PD-L1. In some embodiments, the immune checkpoint inhibitor is an antibody against PD-L1. In some embodiments, the immune checkpoint inhibitor is a monoclonal antibody against PD-L1. In other or additional embodiments, the immune checkpoint inhibitor is a human or humanized antibody against PD-L1. In one embodiment, the immune checkpoint inhibitor reduces the expression or activity of one or more immune checkpoint proteins, such as PD-L1. In another embodiment, the immune checkpoint inhibitor reduces the interaction between PD-1 and PD-L1. Exemplary immune checkpoint inhibitors include antibodies (e.g., an anti-PD-L1 antibody), RNAi molecules (e.g., anti-PD-L1 RNAi), antisense molecules (e.g., an anti-PD-L1 antisense RNA), dominant negative proteins (e.g., a dominant negative PD-L1 protein), and small molecule inhibitors. Antibodies include monoclonal antibodies, humanized antibodies, deimmunized antibodies, and Ig fusion proteins. An exemplary anti-PD-L1 antibody includes clone EH12. Exemplary antibodies against PD-L1 include: Genentech's MPDL3280A (RG7446); Anti-mouse PD-L1 antibody Clone 10F.9G2 (Cat #BE0101) from BioXcell; anti-PD-L1 monoclonal antibody MDX-1105 (BMS-936559) and BMS-935559 from Bristol-Meyer's Squibb; MSB0010718C; mouse anti-PD-L1 Clone 29E.2A3; and AstraZeneca's MEDI4736. In some embodiments, the anti-PD-L1 antibody is an anti-PD-L1 antibody disclosed in any of the following patent publications (herein incorporated by reference): WO2013079174; CN101104640; WO2010036959; WO2013056716; WO2007005874; WO2010089411; WO2010077634; WO2004004771; WO2006133396; WO201309906; US 20140294898; WO2013181634 or WO2012145493.

In some embodiments, the PD-L1 inhibitor is a nucleic acid inhibitor of PD-L1 expression. In some embodiments, the PD-L1 inhibitor is disclosed in one of the following patent publications (incorporated herein by reference): WO2011127180 or WO2011000841. In some embodiments, the PD-L1 inhibitor is rapamycin.

In some embodiments, the immune checkpoint inhibitor is an inhibitor of PD-L2. In some embodiments, the immune checkpoint inhibitor is an antibody against PD-L2. In some embodiments, the immune checkpoint inhibitor is a monoclonal antibody against PD-L2. In other or additional embodiments, the immune checkpoint inhibitor is a human or humanized antibody against PD-L2. In some embodiments, the immune checkpoint inhibitor reduces the expression or activity of one or more immune checkpoint proteins, such as PD-L2. In other embodiments, the immune checkpoint inhibitor reduces the interaction between PD-1 and PD-L2. Exemplary immune checkpoint inhibitors include antibodies (e.g., an anti-PD-L2 antibody), RNAi molecules (e.g., an anti-PD-L2 RNAi), antisense molecules (e.g., an anti-PD-L2 antisense RNA), dominant negative proteins (e.g., a dominant negative PD-L2 protein), and small molecule inhibitors. Antibodies include monoclonal antibodies, humanized antibodies, deimmunized antibodies, and Ig fusion proteins.

In some embodiments, the PD-L2 inhibitor is GlaxoSmithKline's AMP-224 (Amplimmune). In some embodiments, the PD-L2 inhibitor is rHIgM12B7.

In some embodiments, the immune checkpoint inhibitor is an inhibitor of PD-L1. In some embodiments, the immune checkpoint inhibitor is an antibody against PD-1. In some embodiments, the immune checkpoint inhibitor is a monoclonal antibody against PD-1. In other embodiments, the immune checkpoint inhibitor is a human or humanized antibody against PD-1. For example, the inhibitors of PD-1 biological activity (or its ligands) disclosed in U.S. Pat. Nos. 7,029,674; 6,808,710; or U.S. Patent Application Nos: 20050250106 and 20050159351 can be used in the combinations provided herein. Exemplary antibodies against PD-1 include: Anti-mouse PD-1 antibody Clone J43 (Cat #BE0033-2) from BioXcell; Anti-mouse PD-1 antibody Clone RMP1-14 (Cat #BE0146) from BioXcell; mouse anti-PD-1 antibody Clone EH12; Merck's MK-3475 anti-mouse PD-1 antibody (Keytruda®, pembrolizumab, lambrolizumab, h409A1 1); and AnaptysBio's anti-PD-1 antibody, known as ANB011; antibody MDX-1 106 (ONO-4538); Bristol-Myers Squibb's human IgG4 monoclonal antibody nivolumab (Opdivo®, BMS-936558, MDX1106); AstraZeneca's AMP-514, and AMP-224; and Pidilizumab (CT-011 or hBAT-1), CureTech Ltd.

Additional exemplary anti-PD-1 antibodies are described by Goldberg et al, Blood 1 10(1): 186-192 (2007), Thompson et al, Clin. Cancer Res. 13(6): 1757-1761 (2007), and Korman et al, International Application No. PCT/JP2006/309606 (publication no. WO 2006/121168 A1), each of which are expressly incorporated by reference herein. In some embodiments, the anti-PD-1 antibody is an anti-PD-1 antibody disclosed in any of the following patent publications (herein incorporated by reference): WO014557; WO2011110604; WO2008156712; US2012023752; WO2011110621; WO2004072286; WO2004056875; WO20100036959; WO2010029434; WO201213548; WO2002078731; WO2012145493; WO2010089411; WO2001014557; WO2013022091; WO2013019906; WO2003011911; US20140294898; and WO2010001617.

In some embodiments, the PD-1 inhibitor is a PD-1 binding protein as disclosed in WO200914335 (herein incorporated by reference).

In some embodiments, the PD-1 inhibitor is a peptidomimetic inhibitor of PD-1 as disclosed in WO2013132317 (herein incorporated by reference).

In some embodiments, the PD-1 inhibitor is an anti-mouse PD-1 mAb: clone J43, BioXCell (West Lebanon, N.H.).

In some embodiments, the PD-1 inhibitor is a PD-L1 protein, a PD-L2 protein, or fragments, as well as antibody MDX-1 106 (ONO-4538) tested in clinical studies for the treatment of certain malignancies (Brahmer et al., J Clin Oncol. 2010 28(19): 3167-75, Epub 2010 Jun. 1). Other blocking antibodies may be readily identified and prepared by the skilled person based on the known domain of interaction between PD-1 and PD-L1/PD-L2, as discussed above. For example, a peptide corresponding to the IgV region of PD-1 or PD-L1/PD-L2 (or to a portion of this region) could be used as an antigen to develop blocking antibodies using methods well known in the art.

In some embodiments, the immune checkpoint inhibitor is an inhibitor of IDO1. In some embodiments, the immune checkpoint inhibitor is a small molecule against IDO1. Exemplary small molecules against IDO1 include: Incyte's INCB024360, NSC-721782 (also known as 1-methyl-D-tryptophan), and Bristol Meyers Squibb's F001287.

In some embodiments, the immune checkpoint inhibitor is an inhibitor of LAG3 (CD223). In some embodiments, the immune checkpoint inhibitor is an antibody against LAG3. In some embodiments, the immune checkpoint inhibitor is a monoclonal antibody against LAG3. In other or additional embodiments, the immune checkpoint inhibitor is a human or humanized antibody against LAG3. In additional embodiments, an antibody against LAG3 blocks the interaction of LAG3 with major histocompatibility complex (MHC) class II molecules. Exemplary antibodies against LAG3 include: anti-Lag-3 antibody clone eBioC9B7W (C9B7W) from eBioscience; anti-Lag3 antibody LS-B2237 from LifeSpan Biosciences; IMP321 (ImmuFact) from Immutep; anti-Lag3 antibody BMS-986016; and the LAG-3 chimeric antibody A9H12. In some embodiments, the anti-LAG3 antibody is an anti-LAG3 antibody disclosed in any of the following patent publications (herein incorporated by reference): WO2010019570; WO2008132601; or WO2004078928.

In some embodiments, the immune checkpoint inhibitor is an antibody against TIM3 (also known as HAVCR2). In some embodiments, the immune checkpoint inhibitor is a monoclonal antibody against TIM3. In other or additional embodiments, the immune checkpoint inhibitor is a human or humanized antibody against TIM3. In additional embodiments, an antibody against TIM3 blocks the interaction of TIM3 with galectin-9 (Gal9). In some embodiments, the anti-TIM3 antibody is an anti-TIM3 antibody disclosed in any of the following patent publications (herein incorporated by reference): WO2013006490; WO201155607; WO2011159877; or WO200117057. In another embodiment, a TIM3 inhibitor is a TIM3 inhibitor disclosed in WO2009052623.

In some embodiments, the immune checkpoint inhibitor is an antibody against B7-H3. In one embodiment, the immune checkpoint inhibitor is MGA271.

In some embodiments, the immune checkpoint inhibitor is an antibody against MR. In one embodiment, the immune checkpoint inhibitor is Lirilumab (IPH2101). In some embodiments, an antibody against MR blocks the interaction of KIR with HLA.

In some embodiments, the immune checkpoint inhibitor is an antibody against CD137 (also known as 4-1BB or TNFRSF9). In one embodiment, the immune checkpoint inhibitor is urelumab (BMS-663513, Bristol-Myers Squibb), PF-05082566 (anti-4-1BB, PF-2566, Pfizer), or XmAb-5592 (Xencor). In one embodiment, an anti-CD137 antibody is an antibody disclosed in U.S. Published Application No. US 2005/0095244; an antibody disclosed in issued U.S. Pat. No. 7,288,638 (such as 20H4.9-IgG4 [1007 or BMS-663513] or 20H4.9-IgG1 [BMS-663031]); an antibody disclosed in issued U.S. Pat. No. 6,887,673 [4E9 or BMS-554271]; an antibody disclosed in issued U.S. Pat. No. 7,214,493; an antibody disclosed in issued U.S. Pat. No. 6,303,121; an antibody disclosed in issued U.S. Pat. No. 6,569,997; an antibody disclosed in issued U.S. Pat. No. 6,905,685; an antibody disclosed in issued U.S. Pat. No. 6,355,476; an antibody disclosed in issued U.S. Pat. No. 6,362,325 [1D8 or BMS-469492; 3H3 or BMS-469497; or 3E1]; an antibody disclosed in issued U.S. Pat. No. 6,974,863 (such as 53A2); or an antibody disclosed in issued U.S. Pat. No. 6,210,669 (such as 1D8, 3B8, or 3E1). In a further embodiment, the immune checkpoint inhibitor is one disclosed in WO 2014036412. In another embodiment, an antibody against CD137 blocks the interaction of CD137 with CD137L.

In some embodiments, the immune checkpoint inhibitor is an antibody against PS. In one embodiment, the immune checkpoint inhibitor is Bavituximab.

In some embodiments, the immune checkpoint inhibitor is an antibody against CD52. In one embodiment, the immune checkpoint inhibitor is alemtuzumab.

In some embodiments, the immune checkpoint inhibitor is an antibody against CD30. In one embodiment, the immune checkpoint inhibitor is brentuximab vedotin. In another embodiment, an antibody against CD30 blocks the interaction of CD30 with CD30L.

In some embodiments, the immune checkpoint inhibitor is an antibody against CD33. In one embodiment, the immune checkpoint inhibitor is gemtuzumab ozogamicin.

In some embodiments, the immune checkpoint inhibitor is an antibody against CD20. In one embodiment, the immune checkpoint inhibitor is ibritumomab tiuxetan. In another embodiment, the immune checkpoint inhibitor is ofatumumab. In another embodiment, the immune checkpoint inhibitor is rituximab. In another embodiment, the immune checkpoint inhibitor is tositumomab.

In some embodiments, the immune checkpoint inhibitor is an antibody against CD27 (also known as TNFRSF7). In one embodiment, the immune checkpoint inhibitor is CDX-1127 (Celldex Therapeutics). In another embodiment, an antibody against CD27 blocks the interaction of CD27 with CD70.

In some embodiments, the immune checkpoint inhibitor is an antibody against OX40 (also known as TNFRSF4 or CD134). In one embodiment, the immune checkpoint inhibitor is anti-OX40 mouse IgG. In another embodiment, an antibody against 0x40 blocks the interaction of OX40 with OX40L.

In some embodiments, the immune checkpoint inhibitor is an antibody against glucocorticoid-induced tumor necrosis factor receptor (GITR). In one embodiment, the immune checkpoint inhibitor is TRX518 (GITR, Inc.). In another embodiment, an antibody against GITR blocks the interaction of GITR with GITRL.

In some embodiments, the immune checkpoint inhibitor is an antibody against inducible T-cell COstimulator (ICOS, also known as CD278). In one embodiment, the immune checkpoint inhibitor is MEDI570 (MedImmune, LLC) or AMG557 (Amgen). In another embodiment, an antibody against ICOS blocks the interaction of ICOS with ICOSL and/or B7-H2.

In some embodiments, the immune checkpoint inhibitor is an inhibitor against BTLA (CD272), CD160, 2B4, LAIR1, TIGHT, LIGHT, DR3, CD226, CD2, or SLAM. As described elsewhere herein, an immune checkpoint inhibitor can be one or more binding proteins, antibodies (or fragments or variants thereof) that bind to immune checkpoint molecules, nucleic acids that downregulate expression of the immune checkpoint molecules, or any other molecules that bind to immune checkpoint molecules (i.e. small organic molecules, peptidomimetics, aptamers, etc.). In some instances, an inhibitor of BTLA (CD272) is HVEM. In some instances, an inhibitor of CD160 is HVEM. In some cases, an inhibitor of 2B4 is CD48. In some instances, an inhibitor of LAIR1 is collagen. In some instances, an inhibitor of TIGHT is CD112, CD113, or CD155. In some instances, an inhibitor of CD28 is CD80 or CD86. In some instances, an inhibitor of LIGHT is HVEM. In some instances, an inhibitor of DR3 is TL1A. In some instances, an inhibitor of CD226 is CD155 or CD112. In some cases, an inhibitor of CD2 is CD48 or CD58. In some cases, SLAM is self inhibitory and an inhibitor of SLAM is SLAM.

In certain embodiments, the immune checkpoint inhibitor inhibits a checkpoint protein that include, but are not limited to CTLA4 (cytotoxic T-lymphocyte antigen 4, also known as CD152), PD-L1 (programmed cell death 1 ligand 1, also known as CD274), PDL2 programmed cell death protein 2), PD-1 (programmed cell death protein 1, also known as CD279), a B-7 family ligand (B7-H1, B7-H3, B7-H4) BTLA (B and T lymphocyte attenuator, also known as CD272), HVEM, TIM3 (T-cell membrane protein 3), GAL9, LAG-3 (lymphocyte activation gene-3; CD223), VISTA, KIR (killer immunoglobulin receptor), 2B4 (also known as CD244), CD160, CGEN-15049, CHK1 (Checkpoint kinase 1), CHK2 (Checkpoint kinase 2), A2aR (adenosine A2a receptor), CD2, CD27, CD28, CD30, CD40, CD70, CD80, CD86, CD137, CD226, CD276, DR3, GITR, HAVCR2, HVEM, IDO1 (indoleamine 2,3-dioxygenase 1), IDO2 (indoleamine 2,3-dioxygenase 2), ICOS (inducible T cell costimulator), LAIR1, LIGHT (also known as TNFSF14, a TNF family members, MARCO (macrophage receptor with collagenous structure), OX40 (also known as tumor necrosis factor receptor superfamily, member 4, TNFRSF4, and CD134) and its ligand OX40L (CD252), SLAM, TIGHT, VTCN1 or a combination thereof.

In certain embodiments, the immune checkpoint inhibitor interacts with a ligand of a checkpoint protein that comprises CTLA-4, PDL1, PDL2, PD1, BTLA, HVEM, TIM3, GAL9, LAG3, VISTA, KIR, 2B4, CD160, CGEN-15049, CHK1, CHK2, A2aR, a B-7 family ligand, CD2, CD27, CD28, CD30, CD40, CD70, CD80, CD86, CD137, CD226, CD276, DR3, GITR, HAVCR2, HVEM, IDO1, IDO2, ICOS (inducible T cell costimulator), LAIR1, LIGHT, MARCO (macrophage receptor with collagenous structure), OX-40, SLAM, TIGHT, VTCN1 or a combination thereof.

In certain embodiments, the immune checkpoint inhibitor inhibits a checkpoint protein that comprises CTLA-4, PDL1, PD1 or a combination thereof.

In certain embodiments, the immune checkpoint inhibitor inhibits a checkpoint protein that comprises CTLA-4 and PD1 or a combination thereof.

In certain embodiments, the immune checkpoint inhibitor comprises pembrolizumab (MK-3475), nivolumab (BMS-936558), pidilizumab (CT-011), AMP-224, MDX-1 105, durvalumab (MEDI4736), MPDL3280A, BMS-936559, IPH2101, TSR-042, TSR-022, ipilimumab, lirilumab, atezolizumab, avelumab, tremelimumab, or a combination thereof.

In certain embodiments, the immune checkpoint inhibitor is nivolumab (BMS-936558), ipilimumab, pembrolizumab, atezolizumab, tremelimumab, durvalumab, avelumab, or a combination thereof.

In certain embodiments, the immune checkpoint inhibitor is pembrolizumab.

Diagnostic and Prophylactic Formulations

The NaPi2b antibody conjugates disclosed herein are used in diagnostic and prophylactic formulations. In one embodiment, a NaPi2b antibody conjugate disclosed herein is administered to patients that are at risk of developing one or more of the aforementioned diseases, such as for example, without limitation, cancer. A patient's or organ's predisposition to one or more of the aforementioned indications can be determined using genotypic, serological or biochemical markers.

In another embodiment of the disclosure, a NaPi2b antibody conjugate disclosed herein is administered to human individuals diagnosed with a clinical indication associated with one or more of the aforementioned diseases, such as for example, without limitation, cancer. Upon diagnosis, a NaPi2b antibody conjugate disclosed herein is administered to mitigate or reverse the effects of the clinical indication associated with one or more of the aforementioned diseases.

In another embodiment of the disclosure, a method for identifying an ovarian cancer patient amenable to treatment with the conjugates disclosed herein, comprise measuring the status of certain characteristics in a tumor sample obtained from the patient, and identifying the patient for treatment based on the status of certain characteristics in the tumor sample.

In another embodiment of the disclosure, a method for identifying NSCLC patient amenable to treatment with the conjugates disclosed herein, comprise measuring the status of certain characteristics in a tumor sample obtained from the patient, and identifying the patient for treatment based on the status of certain characteristics in the tumor sample.

Antibodies disclosed herein are also useful in the detection of NaPi2b in patient samples and accordingly are useful as diagnostics. For example, NaPi2b antibodies disclosed herein are used in in vitro assays, e.g., ELISA, to detect NaPi2b levels in a patient sample.

In one embodiment, a NaPi2b antibody disclosed herein is immobilized on a solid support (e.g., the well(s) of a microtiter plate). The immobilized antibody serves as a capture antibody for any NaPi2b that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of NaPi2b antigen in the test sample is determined by comparison with a standard curve developed from the standard samples.

It will be appreciated that based on the results obtained using the NaPi2b antibodies disclosed herein in an in vitro diagnostic assay, it is possible to stage a disease in a subject based on expression levels of the NaPi2b antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The disclosure having now been described by way of written description, those of skill in the art will recognize that the disclosure can be practiced in a variety of embodiments and that the foregoing description and examples below are for purposes of illustration and not limitation of the claims that follow.

EXAMPLES

The following working examples are illustrative of the linkers, drug molecules and PBRM, and methods for preparing same. These are not intended to be limiting and it will be readily understood by one of skill in the art that other reagents or methods may be utilized.

Abbreviations

The following abbreviations are used in the reaction schemes and synthetic examples, which follow. This list is not meant to be an all-inclusive list of abbreviations used in the application as additional standard abbreviations, which are readily understood by those skilled in the art of organic synthesis, can also be used in the synthetic schemes and examples.

| AF-HPA | Auristatin F-hydroxypropylamide |
| FBS | Fetal bovine serum |
| MMAE | Monomethyl auristatin E |
| NaPi2b | Type II sodium-phosphate co-transporter |
| NSCLC | Non-small cell lung cancer |

General Information

CDRs were identified by the Kabat numbering scheme.

Tumor growth inhibition (% TGI) was defined as the percent difference in median tumor volumes (MTVs) between treated and control groups.

Treatment efficacy was determined from the incidence and magnitude of regression responses of the tumor size observed during the study. Treatment may cause partial regression (PR) or complete regression (CR) of the tumor in an animal. In a PR response, the tumor volume was 50% or less of its Day 1 volume for three consecutive measurements during the course of the study, and equal to or greater than 13.5 mm$^3$ for one or more of these three measurements. In a CR response, the tumor volume was less than 13.5 mm3 for three consecutive measurements during the course of the study. An animal with a CR response at the termination of a study was additionally classified as a tumor-free survivor (TFS). Animals were monitored for regression responses.

AF-HPA was prepared in a fashion similar to that as described in U.S. Pat. No. 8,685,383, Example 48.

Anti-NaPi2b antibody (XMT-1535) was produced using SEQ ID NO: 38 and SEQ ID NO: 39 from U.S. Pat. No. 8,603,474B2.

Anti-NaPi2b antibody (10H1.11.4B) was produced using SEQ ID NO: 80 and SEQ ID NO: 81 from U.S. Pat. No. 8,535,675B2.

HPLC purification was performed on a Phenomenex Gemini 5 μm 110 Å, 250×10 mm, 5 micron, semi-preparation column.

SEC was performed on a Tosoh Biosciences TSK gel G4000 column (7.8 mm×30 cm, 10 um) or Superose 12 column (GE Healthcare).

WCX was performed on ProPac WCX-10 (94 mm×250 mm) column (ThermoFisher).

Whenever possible the drug content of the conjugates was determined spectrophotometrically otherwise LC/MS or $^1$H-NMR was performed for quantitative determination of the drug content.

The protein content of the protein-polymer-drug conjugates was determined spectrophotometrically at 280 nm or by ELISA.

The molecular weights of the polymer conjugates (reported as the apparent weight average molecular weights or peak molecular weights) were determined by SEC with either polysaccharide or protein molecular weight standards. More specifically, for the polymer or polymer-drug conjugates, polysaccharide molecular weights standard were used, and for protein-drug-polymer conjugates, protein standards are used. Unless specifically indicated the reported polymer carrier molecular weight is the weight average molecular weight of PHF; and the polymer-drug conjugate molecular weight and the protein-polymer-drug conjugates is the peak molecular weight. The NaPi2b antibody-polymer-drug conjugates have a peak molecular weight of about 170 kDa to about 250 kDa. The polymer and polymer conjugates synthesized/measured typically have a polydispersity ≤1.5.

NaPi2b antibody-polymer-drug conjugates were separated from residual unreacted drug-polymer conjugates by (Prep-WCX HPLC). If necessary, additional purification by size exclusion chromatography was conducted to remove any aggregated NaPi2b antibody-polymer-drug conjugates. In general, the NaPi2b antibody-polymer-drug conjugates typically contained <5% (w/w) aggregated fraction as determined by SEC; <0.5% (w/w, e.g., <0.1% w/w) free (unconjugated) drug as determined by RP-HPLC or LC-MS/MS; <1% (w/w) of free polymer-drug conjugate as determined by RP-HPLC and <2% (w/w, e.g., <1% w/w) unconjugated NaPi2b as determined by HIC-HPLC and/or WCX HPLC. Reduced or partially reduced antibodies were prepared using procedures described in the literature, see, for example, Francisco et al., Blood 102 (4): 1458-1465 (2003). The total drug (conjugated and unconjugated) concentration was determined by LC-MS/MS.

To determine the pharmacokinetics of the NaPi2b antibody-polymer-drug conjugates, assays were developed to measure the plasma concentration of the NaPi2b antibody-PHF-AF-HPA conjugate (i.e., conjugated AF-HPA) and concentration of the released, unconjugated AF-HPA and AF (free drugs). To determine the plasma concentration of the free drugs, the acidified plasma sample was treated with acetonitrile to precipitate plasma proteins and antibody drug conjugate and the acetonitrile containing supernatant was analyzed for free drugs by LC-MS/MS. To determine the concentration of conjugated AF-HPA, the acidified plasma sample was subjected to basic hydrolysis followed by acidification and protein precipitation with acetonitrile. The acetonitrile supernatant containing the released AF-HPA and AF was analyzed by LC-MS/MS. The standard curves for the free drugs and conjugated AF-HPA in plasma were linear over the concentration ranges of 1 to 3,000 ng/mL and 10 to 20,000 ng/mL, respectively. Total NaPi2b concentration was determined by ELISA.

General Procedures

General Procedure A. Conjugation of Polymer with Linker or Drug

In general, the conjugation of the polymer (PHF-BA or PHF-GA) with an amine-containing linker, such as, for example, EG2-maleimide or an amine-containing linker drug, such as, for example, AF-HPA-Ala, HPA-Ala, is conducted in an aqueous or 10-90% organic/aqueous solvent mixture in the presence of an activating agent, such as, for example EDC.HCl. Typical organic solvents, include, but are not limited to, water miscible solvents, such as, for example, DMSO, DMF, DMA, NMP, propylene glycol and ACN. To accelerate the coupling, a co-activator, such as, for example, NHS, is added. The polymer is first mixed with the amino-containing compound followed by addition of the co-activator (NHS) and then the addition of the activator (EDC.HCl). The reaction is conducted at 0-10° C., pH 4.5 to 7.5 for 1 h to 24 hours at ambient temperature. The resulting polymer conjugated product is purified by diafiltration or by SEC. The product is concentrated to 2-50 mg/mL, the pH is adjusted to 4.5 to 6.5 to insure drug-polymer linker stability and the conjugate is stored frozen at −20 to −80° C. until further use.

The conjugation of the polymer with the amine-containing linker or drug can be conducted sequentially, in any order, or simultaneously.

General Procedure B. Partial Selective Reduction of Protein (NaPi2b Antibody)

The partial selective reduction of the inter-chain disulfide groups or unpaired disulfide in the relevant NaPi2b antibody prior to conjugation with the polymer-drug conjugate is achieved by using a reducing agent, such as, for example, TCEP, DTT or β-mercaptoethanol. When the reduction is performed with an excess of the reducing agent, the reducing agent is removed prior to conjugation by diafiltration or SEC. The degree of conversion of the NaPi2b disulfide groups into reactive sulfhydryl groups depends on the stoichiometry of NaPi2b, reducing agent, pH, temperature and/or duration of the reaction. When some but not all of the disulfide groups in the PBRM are reduced, the reduced PBRM is a partially reduced NaPi2b.

General Procedure C. Conjugation of Partially Reduced NaPi2b-Targeted Antibody with Polymer Drug Conjugate The conjugation of the partially reduced NaPi2b-targeted antibody to the polymer-drug conjugate is conducted under neutral or slightly basic conditions (pH 6.5-8.5) at antibody concentrations of 1-10 mg/mL and polymer-drug conjugate concentration of 0.5-10 mg/mL. The polymer-drug conjugate is typically used in 1-5 fold excess relative to the desired protein-polymer-drug conjugate stoichiometry. When the antibody is conjugated to the maleimido group of the polymer-drug conjugate, the conjugation is optionally terminated by the addition of a water-soluble maleimido blocking compound, such as, for example, N-acetyl cysteine, cysteine methyl ester, N-methyl cysteine, 2-mercaptoethanol, 3-mercaptopropanoic acid, 2-mercaptoacetic acid, mercaptomethanol (i.e., $HOCH_2SH$), benzyl thiol, and the like.

The resulting NaPi2b-targeted antibody-polymer-drug conjugate is typically purified by diafiltration to remove any unconjugated polymer-drug conjugate, unconjugated drug and small molecule impurities. Alternatively or additionally, appropriate chromatographic separation procedures such as, for example, size-exclusion chromatography, hydrophobic interaction chromatography, ion chromatography such as, for example, WCX chromatography; reversed phase chromatography, hydroxyl apatite chromatography, affinity chromatography or combination thereof may be used to purify the NaPi2b antibody-polymer-drug conjugate. The resulting purified NaPi2b-polymer-drug conjugate is typically formulated in a buffer at pH 5.0-6.5.

Example 1: Synthesis of XMT-1535-(EG2-MI-(10 kDa PHF-BA-(AF-HPA-Ala)))

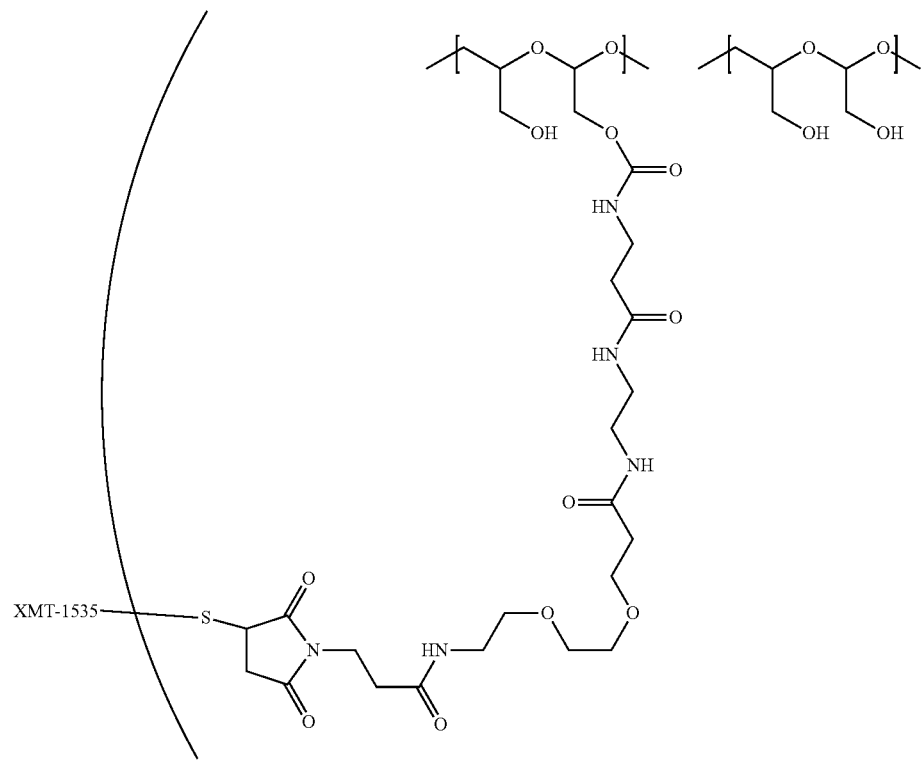

111
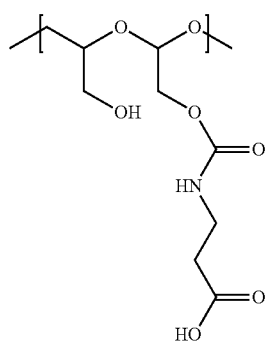
112
-continued
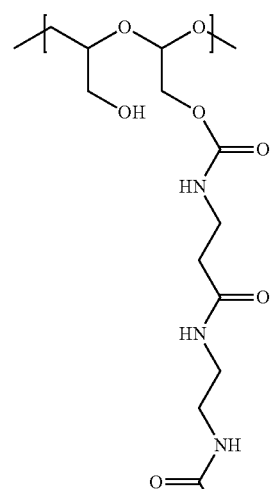
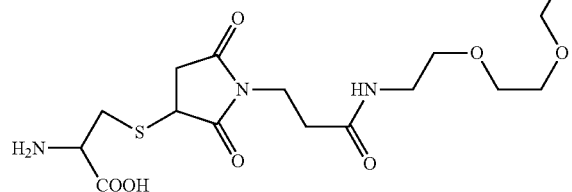
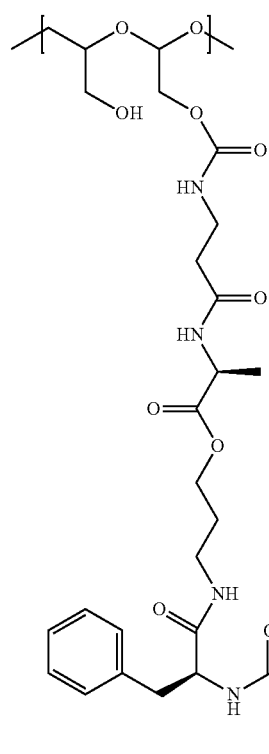
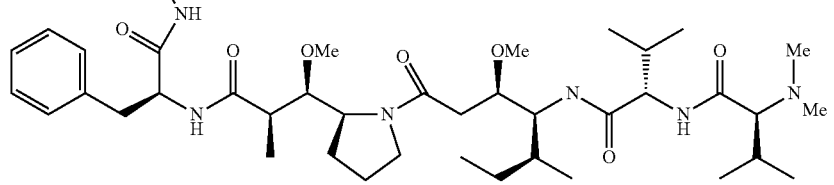

The XMT-1535-(EG2-MI-(10 kDa PHF-BA-(AF-HPA-Ala))) conjugates were prepared using the procedure described in US Application Publication US-2015-0104407-A1. Table I gives the details of the antibody-polymer-drug conjugates.

TABLE I

| Example No. | DAR (Drug:Antibody ratio) |
|---|---|
| 1A | About 8:1 to about 12:1 |
| 1B | About 10:1 to about 14:1 |
| 1C | About 11:1 to about 15:1 |

The XMT-1535-(EG2-MI-(10 kDa PHF-BA-(AF-HPA-Ala))) conjugates had a peak molecular weight of about 180 kDa to about 250 kDa. The polymer and polymer conjugates synthesized/measured typically have a polydispersity ≤1.5. The polymer-drug conjugates (i.e., the drug-carrying polymer chain attached to antibody) contained about 25% mol to about 35% mol beta-alanine, about 7.0% mol to about 10% mol AF-HPA-Ala and about 1.5% mol to about 4% mol EG2-MI.

Example 2: Synthesis of (10H1.11.4B)-(EG2-MI-(10 kDa PHF-BA-(AF-HPA-Ala)))

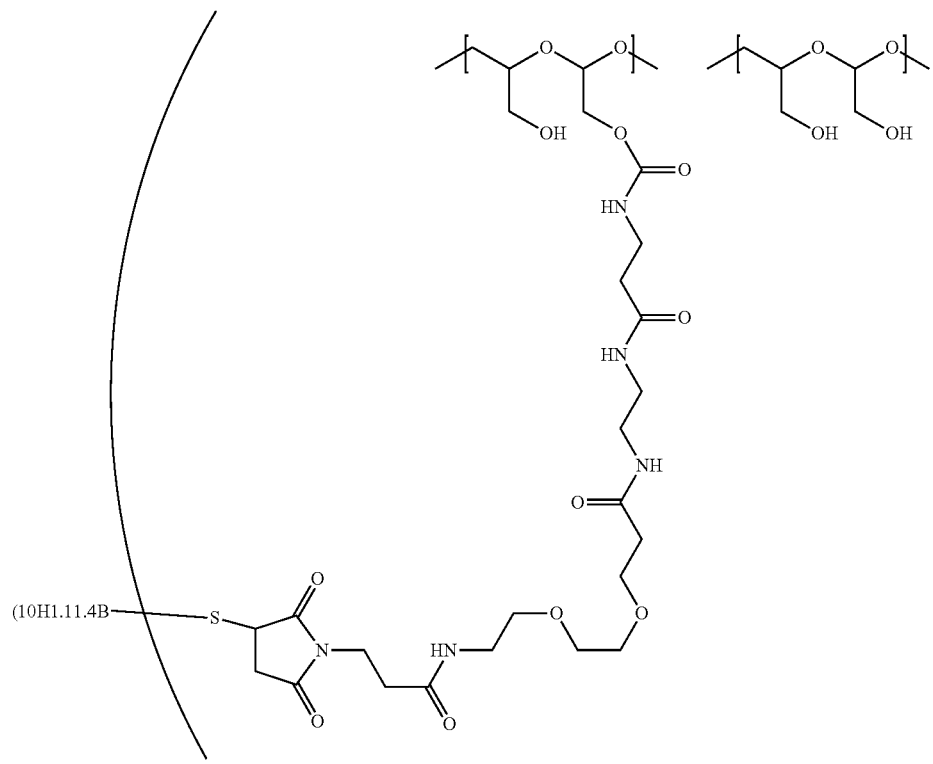

115 116
-continued
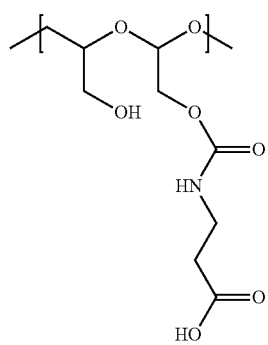
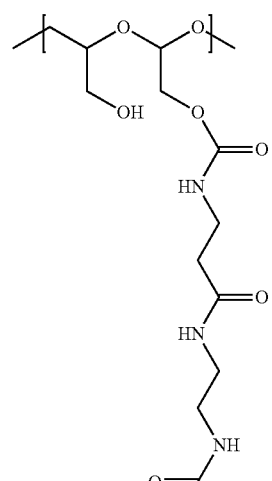
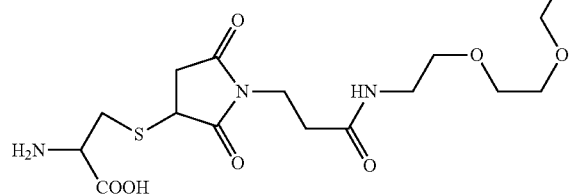
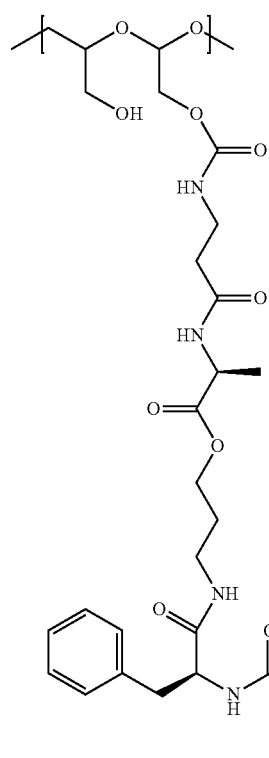

The (10H11.1.4B)-(EG2-MI-(10 kDa PHF-BA-(AF-HPA-Ala))) conjugates (non-binding control) were prepared using the procedure described in US Application Publication US-2015-0104407-A1. Table II gives the details of the antibody-polymer drug conjugates.

TABLE II

| Example No. | DAR (Drug:Antibody ratio) |
|---|---|
| 2A | About 10:1 to about 14:1 |
| 2B | About 14:1 to about 19:1 |
| 2C | About 9:1 to about 13:1 |

The (10H1.11.4B)-(EG2-MI-(10 kDa PHF-BA-(AF-HPA-Ala))) conjugates had a peak molecular weight of about 170 kDa to about 230 kDa. The polymer and polymer conjugates synthesized/measured typically have a polydispersity ≤1.5. The polymer-drug conjugates (i.e., the drug-carrying polymer chain attached to antibody) contained about 25% mol to about 35% mol beta-alanine, about 7% mol to about 10% mol AF-HPA-Ala and about 1.5% mol to about 4% mol EG2-MI.

Example 3: Synthesis of Rituximab-(EG2-MI-(10 kDa PHF-BA-(AF-HPA-Ala)))

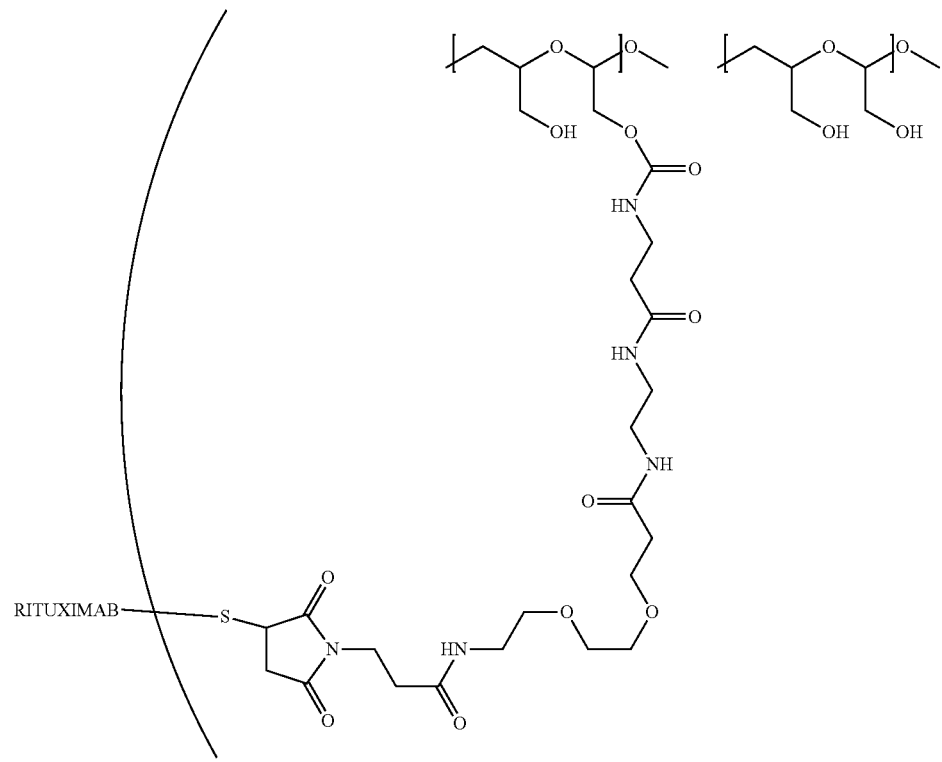

119
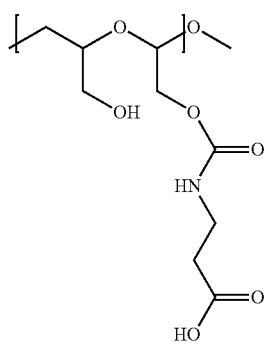
120
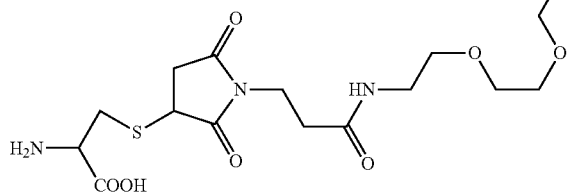
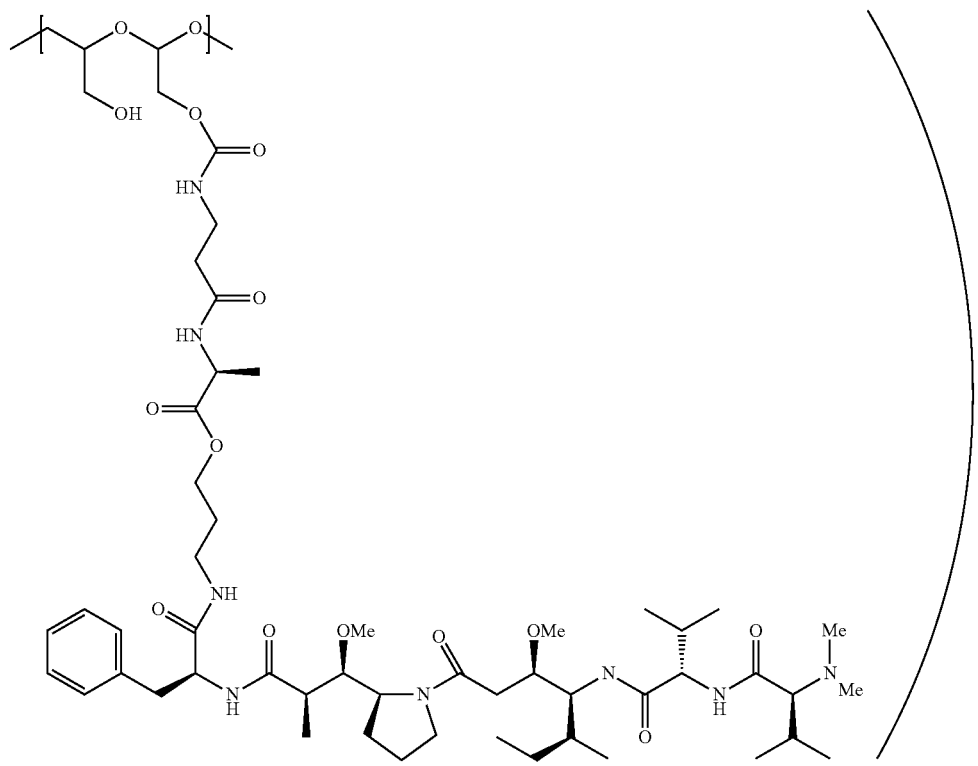

The rituximab-(EG2-MI-(10 kDa PHF-BA-(AF-HPA-Ala))) conjugates (non-binding control) were prepared using the procedure described in US Application Publication US-2015-0104407-A1. Table III gives the details of the antibody-polymer-drug conjugates.

TABLE III

| Example No. | DAR (Drug:Antibody ratio) |
|---|---|
| 3A | About 15:1 to about 21:1 |
| 3B | About 14:1 to about 19:1 |

The rituximab-(EG2-MI-(10 kDa PHF-BA-(AF-HPA-Ala))) conjugates had a peak molecular weight of about 170 kDa to about 230 kDa. The polymer and polymer conjugates synthesized/measured typically have a polydispersity ≤1.5. The polymer-drug conjugates (i.e., the drug-carrying polymer chain attached to antibody) contained about 25% mol to about 35% mol beta-alanine, about 7% mol to about 10% mol AF-HPA-Ala and about 1.5% mol to about 4% mol EG2-MI.

Example 4: Synthesis of (10H1.11.4B)-(MC-VC-PABA-MMAE)

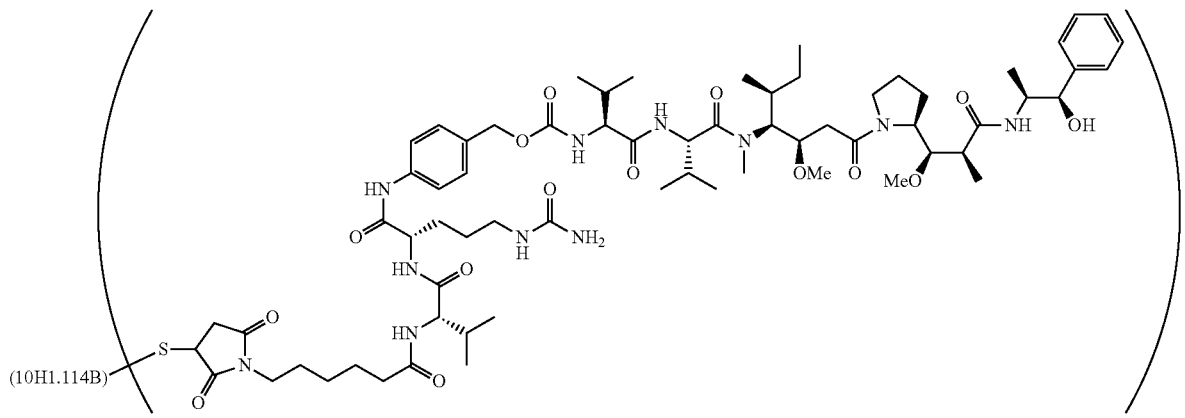

The (10H1.11.4B)-(maleimide-VC-PABA-MMAE) conjugates were prepared using the procedure described in Doronina et al., Nature biotechnology, 21: 778-784 (2003). Table IV gives the details of the antibody-drug conjugates.

TABLE IV

| Example No. | DAR (Drug:Antibody ratio) |
|---|---|
| 4A | 4:1 |
| 4B | 3:1 |

Example 5: Cytotoxicity Assays for NaPi2b-(EG2-MI-(10 kDa PHF-BA-(AF-HPA-Ala))) Conjugates Example 1A, XMT-1535-(EG2-MI-(10 kDa PHF-BA-(AF-HPA-Ala))); Example 2C, (10H1.11.4B)-(EG2-MI-(10 kDa PHF-BA-(AF-HPA-Ala))); Example 3A, Rituximab-(EG2-MI-(10 kDa PHF-BA-(AF-HPA-Ala))) and AF-HPA or Example 1C, XMT-1535-(EG2-MI-(10 kDa PHF-BA-(AF-HPA-Ala))); Example 2C, (10H1.11.4B)-(EG2-MI-(10 kDa PHF-BA-(AF-HPA-Ala))); Example 3B, Rituximab-(EG2-MI-(10 kDa PHF-BA-(AF-HPA-Ala))); and AF-HPA were evaluated for their antiproliferation properties in tumor cell lines in vitro using Cell Titer-Glo (Promega Corp). OVCAR3 (ovarian adenocarcinoma cell line, not amplified, ATCC, Cat.#HTB-161) was cultured in RPMI medium with 20% FBS. TOV-21G (human ovarian adenocarcinoma cell line, not amplified, ATCC, Cat.#CRL-11730) was cultured in 1:1 mixture of MCDB 105 medium containing a final concentration of 1.5 g/L sodium bicarbonate and Medium 199 containing a final concentration of 2.2 g/L sodium bicarbonate with 15% FBS. IGROV1 (ovarian adenocarcinoma cell line, not amplified) was cultured in RPMI medium with 10% FBS. HCC-4006 (human lung carcinoma cell line, not amplified, ATCC, Cat.#ATCC® CRL-2871™) was cultured in in RPMI medium with 10% FBS.

For the cytotoxicity assay, cells were seeded at a density of 5000 cells per well in 96 well plates and allowed to attach during overnight incubation at 37° C. in the presence of 5% $CO_2$. The media was then replaced with fresh media containing a range of the conjugates Examples 1A, 2C, 3A or AF-HPA (100 nM to 0.1 pM) or Examples 1C, 2C, 3B or AF-HPA (100 nM to 0.1 pM) and the cells were incubated for 72 hours or 6 days at 370 in the presence of 5% $CO_2$. Cell survival was measured using CellTiter-Glo® Luminescent Cell Viability Assay (Promega, Madison, Wis.) as described in the kit instructions. Cell viability was normalized to untreated control and expressed as a percentage. The values were plotted and $IC_{50}$ values calculated with GraphPad Prism software (San Diego, Calif.) using 4 parameter, variable slope, dose response curve fitting algorithm. Table VA and VB give illustrative results for the cytotoxicity of the conjugates and AF-HPA.

TABLE VA

| Tumor Cell Line | NaPi2b Receptor number/cell | Example 1A (nM) | Example 2C (nM) | Example 3A (nM) | AF-HPA[1] (nM) |
|---|---|---|---|---|---|
| OVCAR-3 | ~32,000 | 0.002 | 0.014 | 0.26 | 4.18 |
| IGROV1 | ~35,000 | ~5.0 | 10.62 | 53.04 | 28.61 |
| TOV-21G | ~10,000 | 0.04 | 2.03 | 2.76 | 2.07 |
| HCC-4006 | ~52,000 | 0.13 | 2.96 | 1.83 | 0.68 |

TABLE VB

| Tumor Cell Line | NaPi2b Receptor number/cell | Example 1C (nM) | Example 2C (nM) | Example 3B (nM) | AF-HPA[1] (nM) |
|---|---|---|---|---|---|
| OVCAR-3 | ~32,000 | 0.01 | 0.11 | 1.13 | 1.34 |
| IGROV1 | ~35,000 | 0.38 | 2.73 | 37.3 | 25.94 |
| TOV-21G | ~10,000 | 6.68 | 41.54 | 39.68 | 12.70 |
| HCC-4006 | ~52,000 | 0.35 | 3.17 | 5.29 | 7.83 |

[1]= payload equivalent

As shown in Tables VA and VB, the XMT-1535 antibody-polymer-drug conjugates are more potent than the (10H1.11.4B) antibody-polymer-drug conjugates or Rituximab antibody-polymer-drug conjugates in all the tested cell lines.

Example 6. Tumor Growth Response to Administration of NaPi2b Antibody-Polymer-Drug Conjugates Female CB-17 SCID mice were subcutaneously implanted with OVCAR-3 (n=10 for each group) or non-small cell lung cancer tumor fragments (n=10 for each group). Test compounds or vehicle were dosed IV as a single dose on day 1 or as indicated. Tumor size was measured at the times indicated in FIGS. 1 to 3 using digital calipers. Tumor volume was calculated and was used to determine the delay in tumor growth. Mice were sacrificed when tumors reached a size of 1000 mm$^3$. Tumor volumes are reported as the mean±SEM for each group.

FIG. 1 provides the results for the tumor response in mice subcutaneously implanted with OVCAR-3 tumor fragments (n=10 for each group) after IV administration of vehicle; XMT-1535; Example 3A, rituximab-(EG2-MI-(10 kDa PHF-BA-(AF-HPA-Ala))); Example 4A ((10H1.11.4B)-(MC-VC-PABA-MMAE)); Example 2C (10H1.11.4B)-(EG2-MI-(10 kDa PHF-BA-(AF-HPA-Ala))) or Example 1B, XMT 1535-(EG2-MI-(10 kDa PHF-BA-(AF-HPA-Ala))), each at 3 mg/kg (0.21 mg/kg auristatin payload equivalent dose) as a single dose at day 1. The vehicle, XMT-1535; conjugates Example 3A and Example 4A all showed an increase in tumor volume with none of the treatments showing any partial regressions. Conjugates Example 2C and Example 1B each showed a decrease of tumor volume. Conjugate Example 2C had a single partial regression response, while the conjugate Example 1B had 70% regressions consisting of 4 partial regressions and 3 complete regressions. The median time to endpoint (TTE) was 57 days, corresponding to 118% tumor growth delay (TGD) (30.9 days). On Day 23 the tumor growth inhibition (TGI) outcome was 95%. It was statistically different from control (P<0.001, Mann-Whitney test) and was above the 60% potential therapeutics activity threshold.

Figure 2:
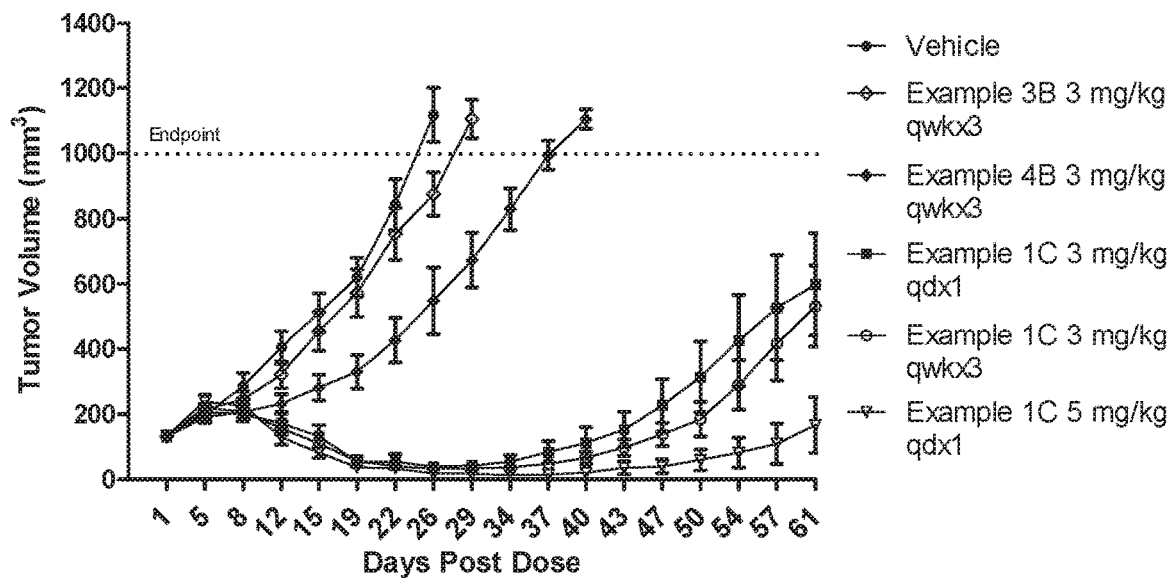
FIG. 2 illustrates the anti-tumor efficacy of Example 3B, rituximab-(EG2-MI-(10 kDa PHF-BA-(AF-HPA-Ala))); Example 4B ((10H1.11.4B)-(MC-VC-PABA-MMAE)); and Example 1C, XMT 1535-(EG2-MI-(10 kDa PHF-BA-(AF-HPA-Ala))) as measured in an OVCAR3 mouse tumor xenograft model.

FIG. 2 provides the results for the tumor response in mice subcutaneously implanted with OVCAR-3 tumor fragments (n=10 for each group) after IV administration of vehicle; Example 3B, rituximab-(EG2-MI-(10 kDa PHF-BA-(AF-HPA-Ala))) at 3 mg/kg dosed weekly for 3 weeks; Example 4B ((10H1.11.4B)-(MC-VC-PABA-MMAE)) at 3 mg/kg dosed weekly for 3 weeks; Example 1C, XMT 1535-(EG2-MI-(10 kDa PHF-BA-(AF-HPA-Ala))) at 3 mg/kg as a single dose at day 1 or at 3 mg/kg dosed weekly for 3 weeks; or Example 1C, XMT 1535-(EG2-MI-(10 kDa PHF-BA-(AF-HPA-Ala))) at 5 mg/kg (0.36 mg/kg auristatin payload equivalent dose) as a single dose at day 1. The vehicle and the conjugates Example 3B and Example 4B all showed an increase in tumor volume with none of the treatments showing any partial regressions. For the conjugate Example 4B the tumor growth inhibition (TGI) at day 22 differed statistically from controls (P<0.001, Mann-Whitney test) and was at 63%—slightly above the 60% potential therapeutic activity threshold. Conjugate Example 1B was most active in this study at all treatment doses producing 80-100% regression responses. For this conjugate the day 22 TGI outcome differed statistically from controls (P<0.001, Mann-Whitney test) and was at 96-97%.

Figure 3:
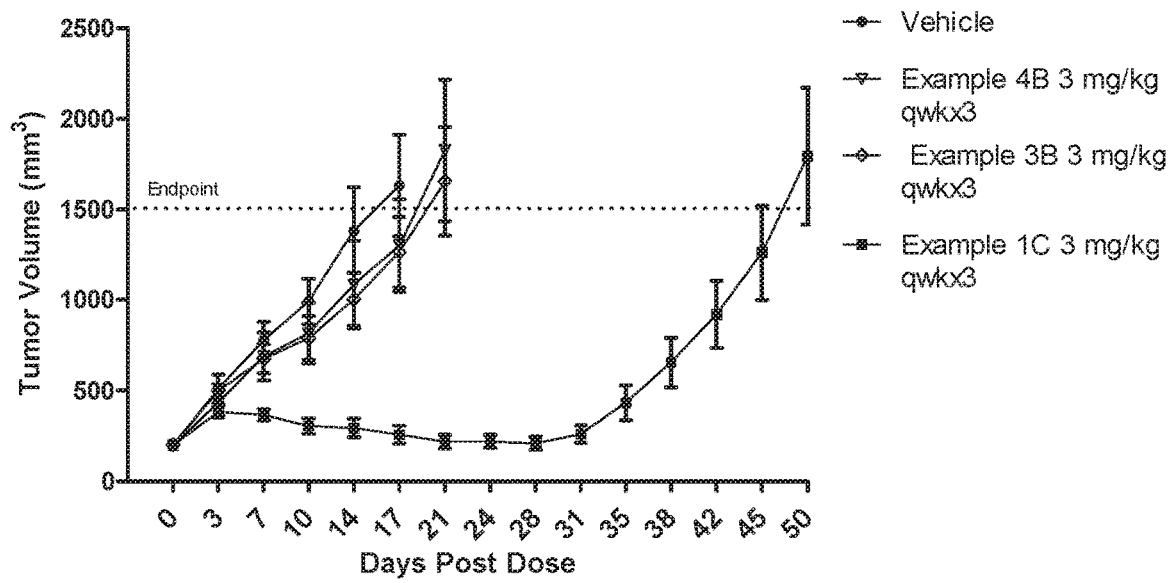
FIG. 3 illustrates the anti-tumor efficacy of Example 3B, rituximab-(EG2-MI-(10 kDa PHF-BA-(AF-HPA-Ala))); Example 4B ((10H1.11.4B)-(MC-VC-PABA-MMAE)); and Example 1C, XMT 1535-(EG2-MI-(10 kDa PHF-BA-(AF-HPA-Ala))), as measured in a KRAS mutant patient derived non-small cell lung cancer xenograft model.

FIG. 3 provides the results for the tumor response in patient derived xenograft KRAS mutant non-small cell lung cancer model (CTG-0860) (n=10 for each group) after IV administration of vehicle; Example 3B, rituximab-(EG2-MI-(10 kDa PHF-BA-(AF-HPA-Ala))); Example 4B ((10H1.11.4B)-(MC-VC-PABA-MMAE)); or Example 1C, XMT 1535-(EG2-MI-(10 kDa PHF-BA-(AF-HPA-Ala))), each at 3 mg/kg dosed weekly for 3 weeks. Vehicle; conjugates Example 3B and Example 4B each showed an increase in tumor volume. Comparison of Day 17 tumor volumes showed that tumor volume of the Example 1C was significantly lower than that of the Vehicle Control group (p≤0.05) Analysis of data from Day 0 to Day 17 showed that the Example 1C 3 mg/kg group had significantly lower tumor volume compared to that of the vehicle control group (p≤0.01). There were 2 PRs in the Example 1C 3 mg/kg group. There were no deaths in any of the groups during the study.

Figure 4:
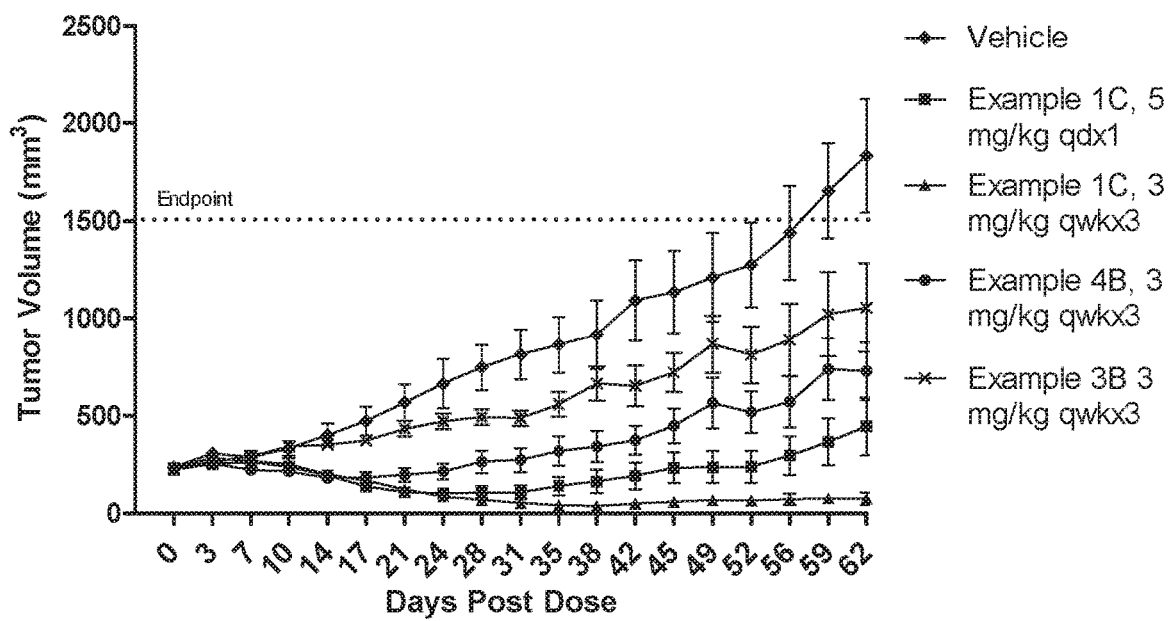
FIG. 4 illustrates the anti-tumor efficacy of Example 3B, rituximab-(EG2-MI-(10 kDa PHF-BA-(AF-HPA-Ala))); Example 4B ((10H1.11.4B)-(MC-VC-PABA-MMAE)); and Example 1C, XMT 1535-(EG2-MI-(10 kDa PHF-BA-(AF-HPA-Ala))), as measured in a patient derived non-small cell lung cancer xenograft model.

FIG. 4 provides the results for the tumor response in patient derived xenograft non-small cell lung cancer model (CTG-0852) (n=8 for each group) after IV administration of vehicle; Example 3B, rituximab-(EG2-MI-(10 kDa PHF-BA-(AF-HPA-Ala))); Example 4B ((10H1.11.4B)-(MC-VC-PABA-MMAE)); Example 1C, XMT 1535-(EG2-MI-(10 kDa PHF-BA-(AF-HPA-Ala))), each at 3 mg/kg dosed weekly for 3 weeks or Example 1C, XMT 1535-(EG2-MI-(10 kDa PHF-BA-(AF-HPA-Ala))), at 5 mg/kg as a single dose on day 1. Analysis of data from Day 0 to Day 62 showed that all of the groups had significantly lower tumor volume compared to that of the vehicle control group (p≤0.01 or p≤0.0001). There were 3 PRs in the Example 4B 3 mg/kg group. There were 7 PRs in the Example 1C 5 mg/kg group and 5 PRs, 1 CR, and 2 TFS in the Example 1C 3 mg/kg group. No PRs, CRs, or TFS in the Example 3B 3 mg/kg group. There were no deaths in any of the groups during the study.

Figure 5:
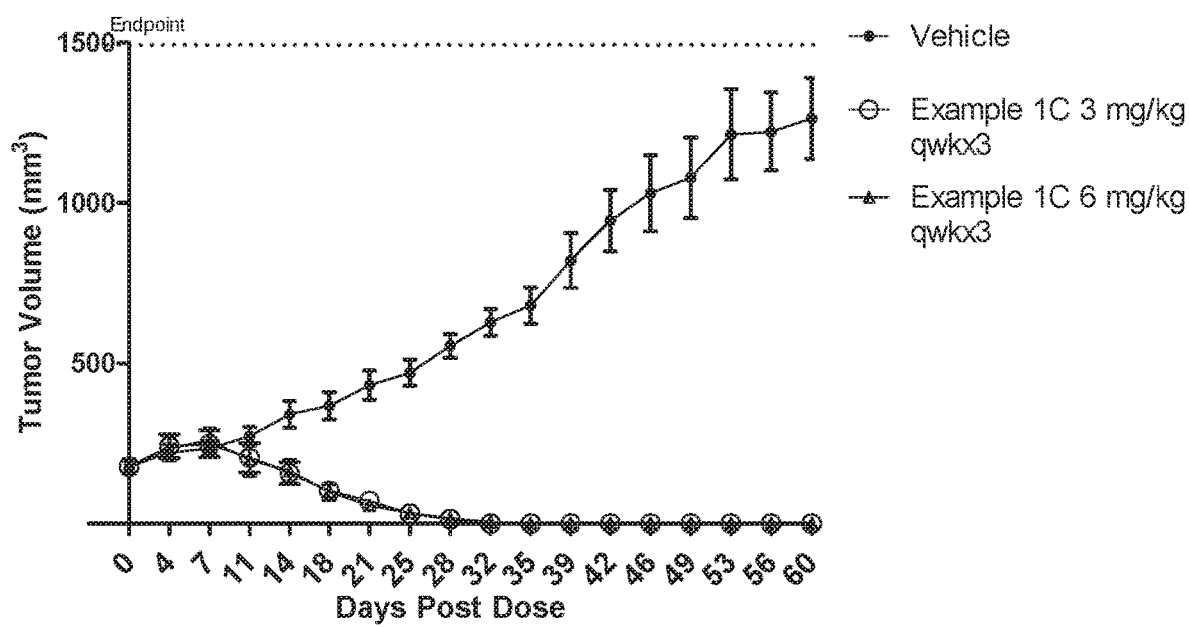
FIG. 5 illustrates the anti-tumor efficacy of Example 1C, XMT 1535-(EG2-MI-(10 kDa PHF-BA-(AF-HPA-Ala))), as measured in a patient derived non-small cell lung cancer xenograft model.

FIG. 5 provides the results for the tumor response in patient derived xenograft non-small cell lung cancer model (ST1906, BRAF K601E mutation) (n=6 for each group) after IV administration of vehicle; and Example 1C, XMT 1535-(EG2-MI-(10 kDa PHF-BA-(AF-HPA-Ala))), at 3 mg/kg or 6 mg/kg dosed weekly for 3 weeks. Vehicle showed an increase in tumor volume while the conjugate Example 1C showed robust anti-tumor activity. Six out of six exhibited TFS at day 60 after treatment with the conjugate Example 1C.

Figure 7:
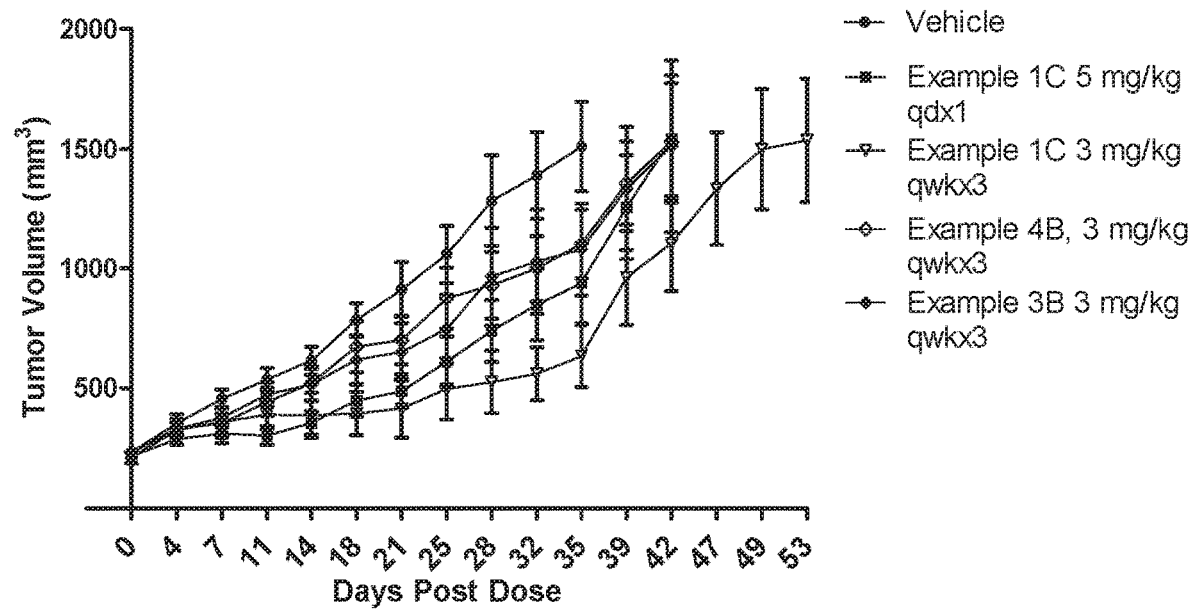
FIG. 7 illustrates the anti-tumor efficacy of Example 3B, rituximab-(EG2-MI-(10 kDa PHF-BA-(AF-HPA-Ala))); Example 4B ((10H1.11.4B)-(MC-VC-PABA-MMAE)); and Example 1C, XMT 1535-(EG2-MI-(10 kDa PHF-BA-(AF-HPA-Ala))), as measured in a patient derived non-small cell lung cancer xenograft model.

FIG. 7 provides the results for the tumor response in patient derived xenograft non-small cell lung cancer model (CTG-0178) (n=8 for each group) after IV administration of vehicle; Example 3B, rituximab-(EG2-MI-(10 kDa PHF-BA-(AF-HPA-Ala))); Example 4B ((10H1.11.4B)-(MC-VC-PABA-MMAE)); or Example 1C, XMT 1535-(EG2-MI-(10 kDa PHF-BA-(AF-HPA-Ala))), each at 3 mg/kg dosed weekly for 3 weeks or Example 1C, XMT 1535-(EG2-MI-(10 kDa PHF-BA-(AF-HPA-Ala))) at 5 mg/kg as a single dose. Vehicle; conjugates Example 3B and Example 4B each showed an increase in tumor volume. The conjugate Example 1C at 3 mg/kg and 5 mg/kg significantly lower tumor growth compared to that of the vehicle control group (p≤0.05). There were no deaths in any of the groups during the study.

Figure 8:
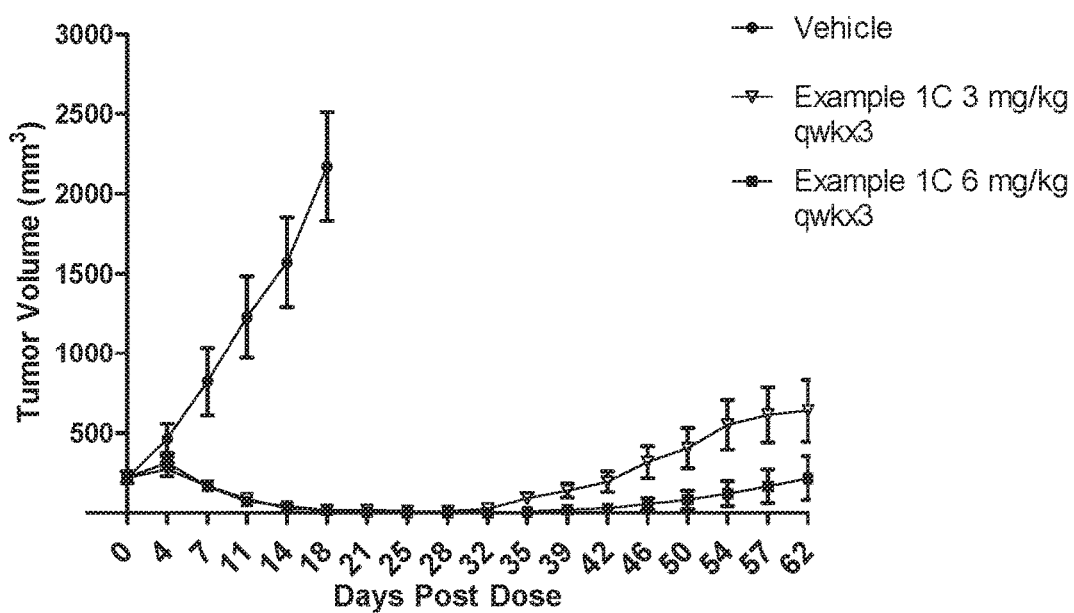
FIG. 8 illustrates the anti-tumor efficacy of Example 1C, XMT 1535-(EG2-MI-(10 kDa PHF-BA-(AF-HPA-Ala))), as measured in a patient derived non-small cell lung cancer xenograft model.

FIG. 8 provides the results for the tumor response in patient derived xenograft non-small cell lung cancer model (ST1437, EGFR wild type, Alk wild type mutation) (n=6 for each group) after IV administration of vehicle; and Example 1C, XMT 1535-(EG2-MI-(10 kDa PHF-BA-(AF-HPA-Ala))), at 3 mg/kg or 6 mg/kg dosed weekly for 3 weeks. Vehicle showed an increase in tumor volume while the conjugate Example 1C showed anti-tumor activity. One out of six exhibited TFS at day 60 after treatment with the conjugate Example 1C.

Figure 9:
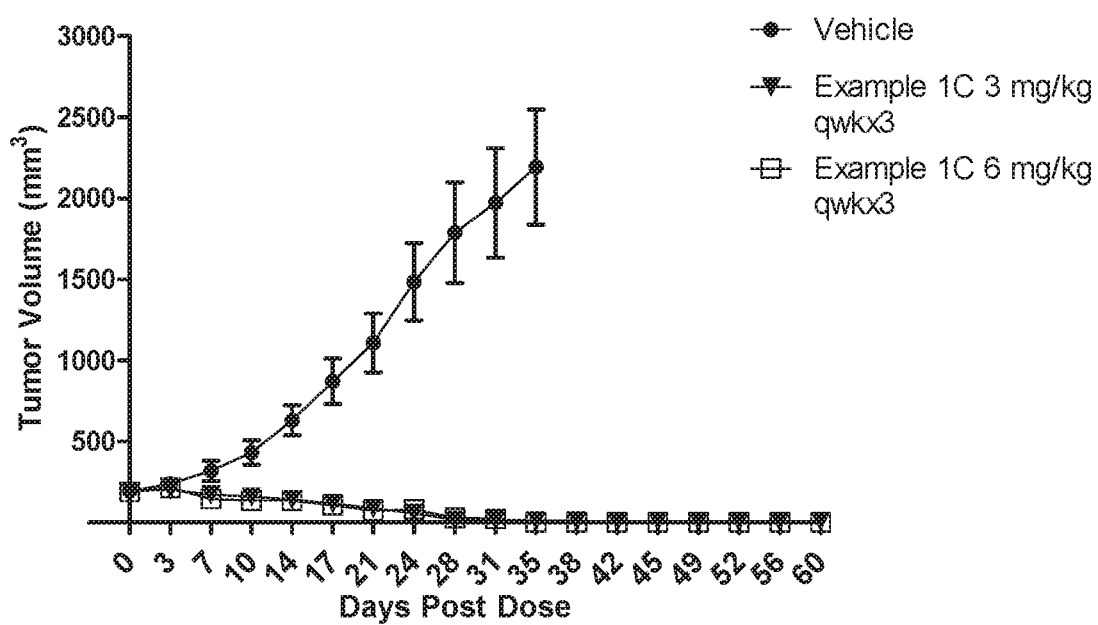
FIG. 9 illustrates the anti-tumor efficacy of Example 1C, XMT 1535-(EG2-MI-(10 kDa PHF-BA-(AF-HPA-Ala))), as measured in a patient derived non-small cell lung cancer xenograft model.

FIG. 9 provides the results for the tumor response in patient derived xenograft non-small cell lung cancer model (ST742, EMLK-Alk translocation) (n=6 for each group) after IV administration of vehicle; and Example 1C, XMT 1535-(EG2-MI-(10 kDa PHF-BA-(AF-HPA-Ala))), at 3 mg/kg or 6 mg/kg dosed weekly for 3 weeks. Vehicle showed an increase in tumor volume while the conjugate Example 1C showed anti-tumor activity. Five out of six exhibited TFS at day 60 after treatment with the conjugate Example 1C.

Figure 10:
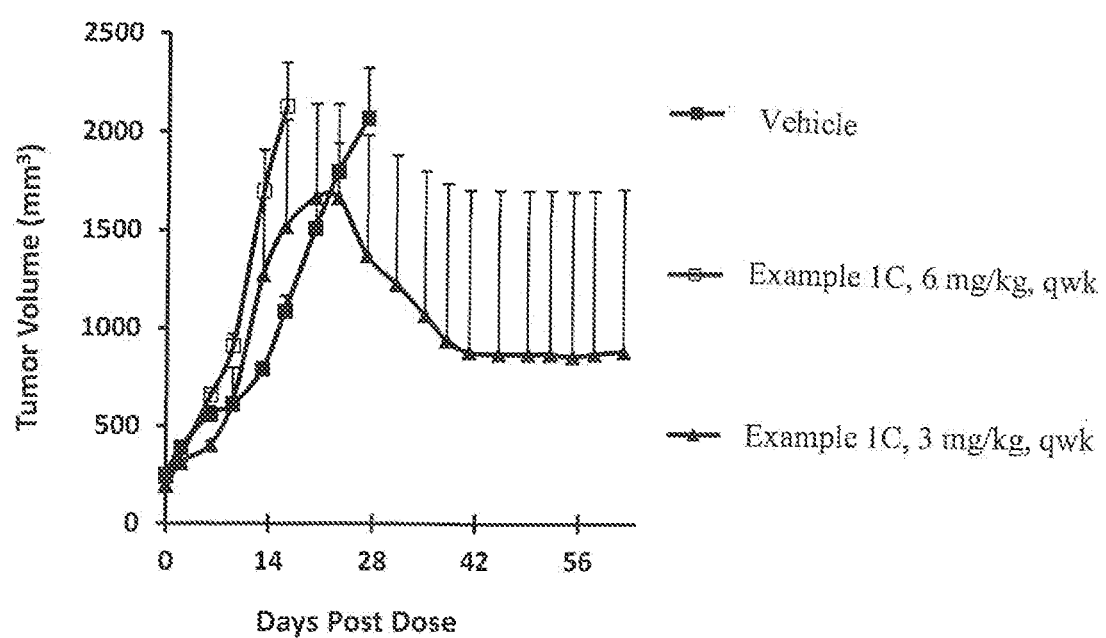
FIG. 10 illustrates the anti-tumor efficacy of Example 1C, XMT 1535-(EG2-MI-(10 kDa PHF-BA-(AF-HPA-Ala))), as measured in a patient derived non-small cell lung cancer xenograft model.

FIG. 10 provides the results for the tumor response in patient derived xenograft non-small cell lung cancer model (ST1243, EGFR amplification, KIT amplification, CDKN2A deletion) (n=6 for each group) after IV administration of vehicle; and Example 1C, XMT 1535-(EG2-MI-(10 kDa PHF-BA-(AF-HPA-Ala))), at 3 mg/kg or 6 mg/kg dosed weekly for 3 weeks. Vehicle showed an increase in tumor volume while the conjugate Example 1C showed anti-tumor activity.

Example 7: Cell Binding Affinity for XMT-1535 and NaPi2b-(EG2-MI-(10 kDa PHF-BA-(AF-HPA-Ala))) Conjugates Using Flow Cytometry The cell surface binding of the Example 1C, XMT 1535-(EG2-MI-(10 kDa PHF-BA-(AF-HPA-Ala))) and anti-NaPi2B antibody XMT 1535, to antigen expressing cells was evaluated by flow cytometry. TOV-21G or OVCAR3 cells were grown overnight to approximately 90% confluent cultures in media, then were released from the plate surface by treatment with Trypsin-EDTA (Gibco-Thermo Fisher Scientific, USA). The detached cells were washed once with ice cold media containing 6% goat serum and resuspended in the same media. 50,000 cells were aliquoted per well of a V-bottom, 96-well plate and incubated with a range of test articles concentrations (0.23-500 nM) in 100 µl Media (1:1 mixture MCDB105 (1.5 g/L sodium bicarbonate) and Medium 199 (2.2 g/L sodium bicarbonate plus 15% FBS)) with 6% goat serum on ice for 3 hours. The cells were then washed once with ice cold PBS and resuspended in 150 µl Media with 2% goat serum and 6 µg/ml of a secondary fluorescently labeled antibody, Alexa Fluor® 647-labelled goat anti-human IgG (Life Technologies, Cat #A-21445) for 1 hour on ice. The cells were washed once with ice cold PBS and suspended in 150 µl of ice cold PBS with 1% paraformaldehyde. The amount of fluorescence bound per cell was determined by running 5000 cells for each treatment on a MACSQuant flow cytometer (Miltenyi Biotec, Bergisch Gladbach, Germany). The median fluorescence value for each treatment was graphed, and the binding constant, $K_D$ was calculated for each test article with GraphPad Prism software by non-linear regression using the one site specific binding model.

TABLE VI

| Test Compound | $K_D$ (nM) TOV-21G | $K_D$ (nM) OVCAR3 |
|---|---|---|
| XMT 1535 | 2.46 | 6.59 |
| Example 1C | 3.97 | 3.84 |

As shown in Table VI, the naked antibody XMT-1535 and the XMT-1535-antibody-polymer-drug conjugate have similar binding affinities for the tested cell line.

Example 8: Non-Human Primate Toxicological and PK Study

A single-dose toxicity study was conducted in cynomolgus monkeys with Example 1C, XMT-1535-(EG2-MI-(10 kDa PHF-BA-(AF-HPA-Ala))). The conjugate was administered to groups of 2 animals/sex at 0 mg/kg (Group 1), 1.25 mg/kg (1074 µg/m² auristatin payload equivalents; Group 2), 2.5 mg/kg (2147 µg/m² auristatin payload equivalents; Group 3) or 5 mg/kg (or 4294 µg/m² auristatin payload equivalents; Group 4) as a single iv infusion. Blood was collected for hematology, coagulation, and serum chemistry analysis from all groups on days −7, 3, 8, 15, and 22. Blood samples were also collected at predose, 10 minutes, 1, 6, 24, 48, 72, 96, and 168 hours following the end of the IV infusions, and on days 15 and 22 for the PK determination.

The conjugate Example 1C was well tolerated in cynomolgus monkeys when administered up to 5 mg/kg (i.e., 4294 µg/m² auristatin payload equivalents), with no observed target-mediated toxicity and limited adverse findings. There was no evidence of bone marrow toxicity. There was no moribundity in Groups 2, 3, and 4. The test article related findings are shown in Table VII below.

TABLE VII

| | Terminal Necropsy | | | Recovery Necropsy | | |
|---|---|---|---|---|---|---|
| Organ | 1.25 mg/kg | 2.5 mg/kg | 5 mg/kg | 1.25 mg/kg | 2.5 mg/kg | 5 mg/kg |
| Bone Marrow | None | None | None | None | None | None |
| Liver* | None | None | Minimal hepatocyte apoptosis (1 female) | None | None | None |
| Testes | None | None | None | None | None | None |
| Lung | None | None | Minimal mixed inflammatory cell infiltrate (1 male) | None | None | Minimal mixed inflammatory cell infiltrate (1 male) |
| Urinary Bladder | None | None | Minimal mucosal apoptosis; occasional mitotic figures (1 male) | None | None | None |

TABLE VII-continued

| | Terminal Necropsy | | | Recovery Necropsy | | |
|---|---|---|---|---|---|---|
| Organ | 1.25 mg/kg | 2.5 mg/kg | 5 mg/kg | 1.25 mg/kg | 2.5 mg/kg | 5 mg/kg |
| Stomach | Minimal mucosal neutrophil infiltrate (1 female) | None | Mild focal ulceration (1 male) | None | None | None |
| Cecum | None | Mild focal ulceration (1 female) | None | None | None | None |

*Minimal Kupffer cell hypertrophy with occasional mitotic figures was seen in all test article treated animals at terminal and recovery necropsies (non-adverse finding).

One animal in all groups was affected by adverse changes involving the gastrointestinal tract at terminal necropsy. Recovery animals had test article related findings (one in each tissue) in the liver (Groups 2 to 4), spleen (Groups 3 and 4), and lung (Group 4) but none of these were considered adverse. There was transient increase in neutrophil counts and a monocytosis in conjunction with increased globulin concentrations, decreased albumin levels and decreased albumin to globulin ratios. Also, elevated creatine kinase (CK) and aspartate aminotransferase (AST) levels were observed. None of the alterations detected persisted through the recovery period. There was no myelosuppression and no neutropenia. In addition, there were no test article gross findings at necropsy or related body weight loss. Based on the efficacy and this non-human primate toxicological study therapeutic index for the conjugate Example 1C, XMT-1535-(EG2-MI-(10 kDa PHF-BA-(AF-HPA-Ala))) is about 6.

Figure 6A:
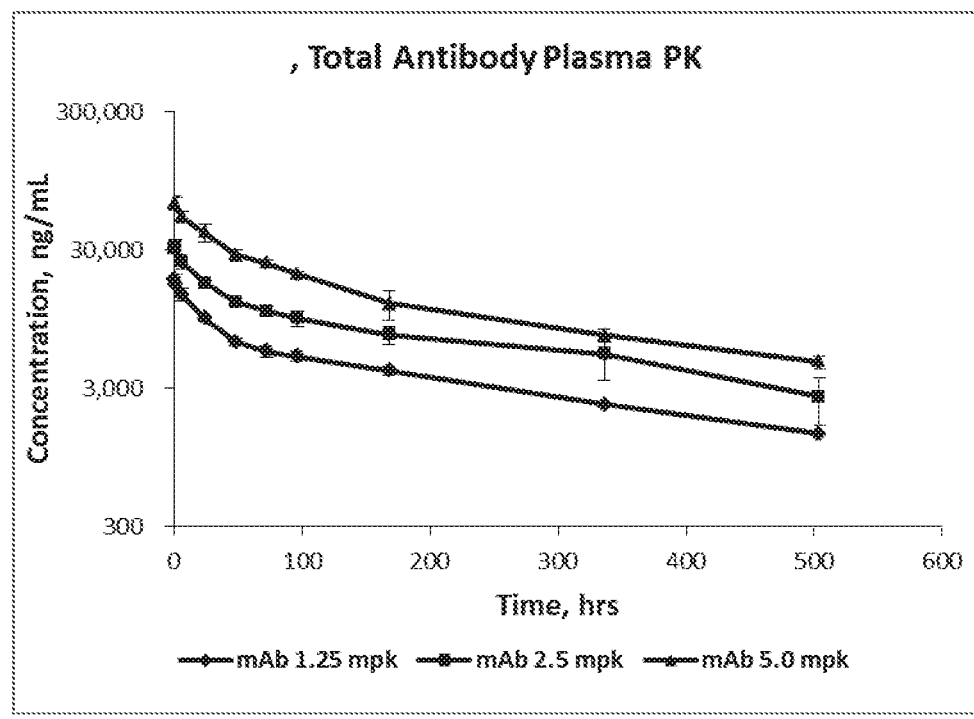
FIGS. 6A and 6B respectively show the plasma pharmacokinetics for the total antibody and the total drug after administration of Example 1C at 1.25 mg/kg (1074 µg/m$^2$ auristatin payload equivalents), 2.5 mg/kg (2147 µg/m$^2$ auristatin payload equivalents) or 5 mg/kg (or 4294 µg/m$^2$ auristatin payload equivalents) as a single IV infusion in cynomolgus monkeys.
Figure 6B:
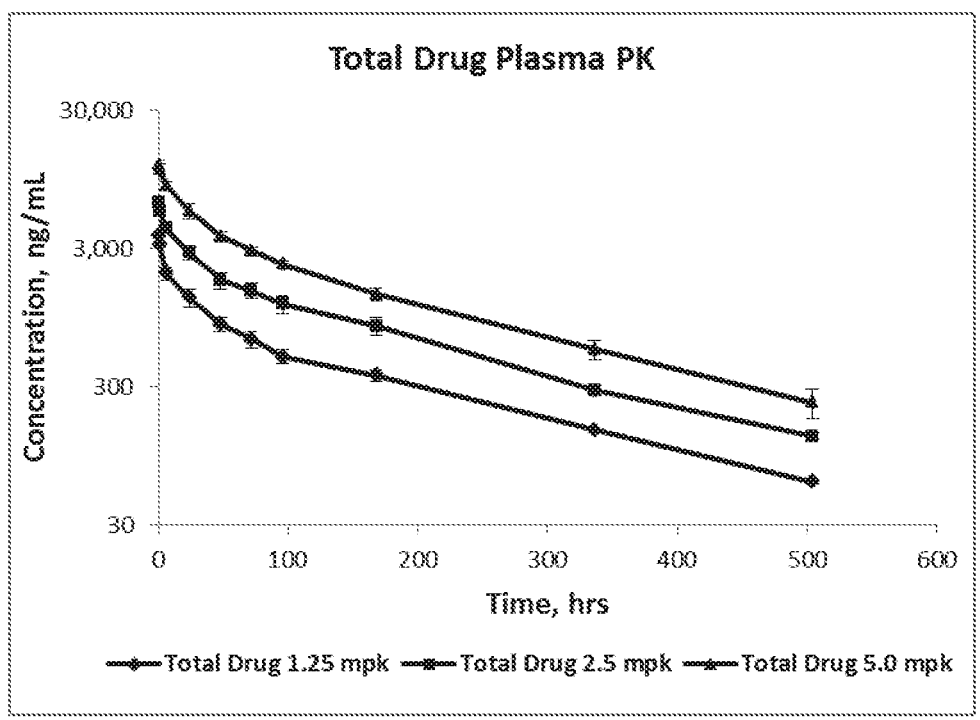

The blood samples were analyzed by LC-MS/MS to determine the concentration of total AF-HPA and by ELISA to determine the total antibody concentration at each time point. FIGS. 6A and 6B show the plasma pharmacokinetics for the total antibody and total drug respectively after administration of a single dose in cynomolgus monkeys with the conjugate Example 1C at 1.25 mg/kg (1074 µg/m$^2$ auristatin payload equivalents; Group 2), 2.5 mg/kg (2147 µg/m$^2$ auristatin payload equivalents; Group 3) or 5 mg/kg (or 4294 µg/m$^2$ auristatin payload equivalents; Group 4). Table VIII gives the calculated AUC$_{0\ to\ 504}$ hrs and half-lives for total antibody and the total AF-HPA. Free drugs (i.e., unconjugated AF and unconjugated AF-HPA) were not detected (LLOQ of the LC MS/MS method was 1 ng/mL).

TABLE VIII

| Plasma Exposure AUC$_{0\text{-}504\ hrs}$ Dose Normalized (µg · hrs/mL/mg/kg) | | Plasma Half-life T$_{1/2}$, Dose Range Average (Days) | | |
|---|---|---|---|---|
| Total Antibody | Total Drug | Total Antibody | Total Drug | Drug Release |
| 1,407 ± 99 | 157 ± 13 | 8.8 ± 0.7 | 5.2 ± 0.2 | 11.6 ± 0.9 |

The XMT-1535-polymer-drug conjugate had a half-life of ~9 days with an AUC$_{0\text{-}54}$ hrs of ~1.4 mg*hr/mL/mg/kg. The total AF-HPA had a half-life of ~5 days with an AUC$_{0\text{-}504}$ hrs of ~157 g*hr/mL/mg/kg. The conjugate demonstrated good stability in plasma with little or no detection of free drugs.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A conjugate having Formula:

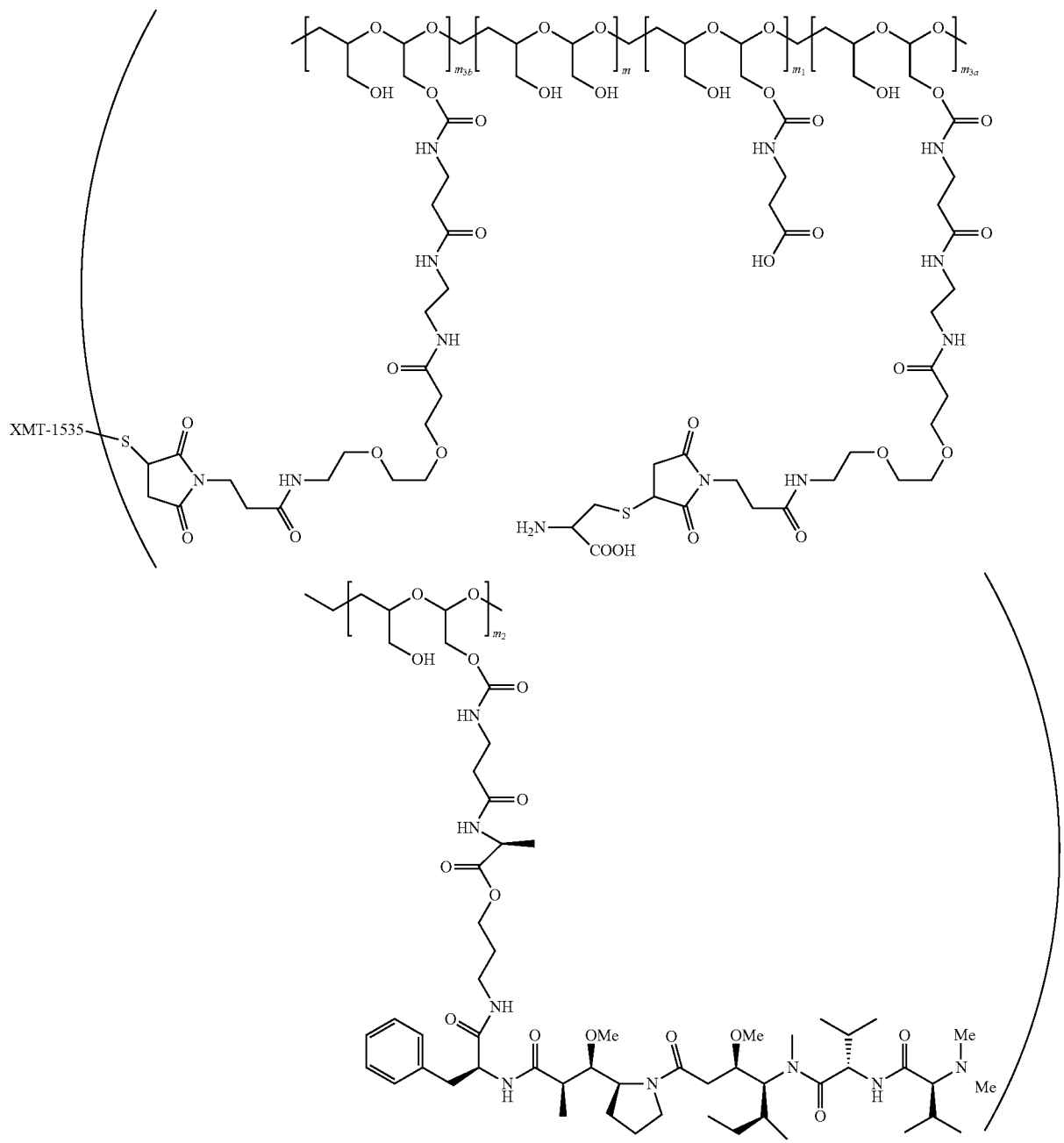

wherein:
the conjugate comprises a polymeric scaffold comprising poly(1-hydroxymethylethylene hydroxymethyl-formal) (PHF), wherein the PHF has a molecular weight ranging from 5 kDa to 10 kDa;
m is an integer from 1 to 75,
$m_1$ is an integer from about 2 to about 35,
$m_2$ is an integer from about 2 to about 10,
$m_{3a}$ is an integer from 0 to about 4,
$m_{3b}$ is an integer from 1 to about 5,
the sum of m, $m_1$, $m_2$, $m_{3a}$, and $m_{3b}$ ranges from about 40 to about 75,
XMT-1535 comprises a variable light chain complementarity determining region 1 (CDRL1) compris-ing the amino acid sequence SASQDIGNFLN (SEQ ID NO: 8); a variable light chain complementarity determining region 2 (CDRL2) comprising the amino acid sequence YTSSLYS (SEQ ID NO: 9); a variable light chain complementarity determining region 3 (CDRL3) comprising the amino acid sequence QQYSKLPLT (SEQ ID NO: 10); a variable heavy chain complementarity determining region 1 (CDRH1) comprising the amino acid sequence GYTFTGYNIH (SEQ ID NO: 5); a variable heavy chain complementarity determining region 2 (CDRH2) comprising the amino acid sequence AIYPGNGDTSYKQKFRG (SEQ ID NO:

6); and a variable heavy chain complementarity determining region 3 (CDRH3) comprising the amino acid sequence GETARATFAY (SEQ ID NO: 7); and wherein the ratio between the PHF and XMT-1535 is an integer from 2 to about 6.

2. The conjugate of claim 1, wherein the ratio between m2 and XMT-1535 is about 16:1 to 10:1.

3. The conjugate of claim 1, wherein the ratio between m2 and XMT-1535 is about 20:1 to 6:1.

4. The conjugate of claim 1, wherein the ratio between m2 and XMT-1535 is about 12:1 to 8:1.

5. The conjugate of claim 1, wherein XMT-1535 comprises a heavy chain comprising the amino acid sequence of SEQ ID NO: 1 and a light chain comprising the amino acid sequence of SEQ ID NO: 2.

6. A pharmaceutical composition comprising a conjugate of claim 1 and a pharmaceutically acceptable carrier.

7. A method of preparing a conjugate according to claim 1, comprising reacting XMT-1535 with the polymeric scaffold such that the conjugate is formed.

8. A method of treating a *NaPi*2B expressing cancer in a subject in need thereof, the method comprising administering a conjugate according to claim 1 to the subject in an amount sufficient to treat the cancer.

9. The method of claim 8, wherein the subject is human.

10. The method of claim 8, wherein the *NaPi*2B expressing cancer is selected from the group consisting of ovarian cancer, thyroid cancer, colorectal cancer, lung cancer, breast cancer, kidney cancer and salivary duct carcinoma.

11. The method of claim 8, wherein the lung cancer is non-small cell lung cancer (NSCLC).

12. The method of claim 11, wherein the non-small cell lung cancer is non-squamous non-small cell lung cancer.

13. The method of claim 10, wherein the ovarian cancer is epithelial ovarian cancer.

14. The method of claim 8, further comprising administration of a therapeutic agent to the subject.

15. The method of claim 8, wherein the subject has one or more ovarian cancers selected from recurrent ovarian cancer, platinum-sensitive ovarian cancer, platinum-refractory ovarian cancer, and platinum-resistant ovarian cancer; or the subject has advanced ovarian cancer and has not received any prior chemotherapy for treating cancer.

* * * * *